(12) United States Patent
Brown et al.

(10) Patent No.: US 7,772,432 B2
(45) Date of Patent: Aug. 10, 2010

(54) AMIDOBENZAMIDE DERIVATIVES WHICH ARE USEFUL AS CYTOKINE INHIBITORS

(75) Inventors: Dearg Sutherland Brown, Macclesfield (GB); George Robert Brown, Macclesfield (GB)

(73) Assignee: AstraZeneca AB (SE)

( * ) Notice: Subject to any disclaimer, the term of this patent is extended or adjusted under 35 U.S.C. 154(b) by 1524 days.

(21) Appl. No.: 10/947,463

(22) Filed: Sep. 23, 2004

(65) Prior Publication Data
US 2005/0038081 A1 Feb. 17, 2005

Related U.S. Application Data

(62) Division of application No. 09/762,106, filed as application No. PCT/GB99/02494 on Jul. 29, 1999, now Pat. No. 6,821,965.

(30) Foreign Application Priority Data

Aug. 4, 1998 (GB) ................................. 9816837.0

(51) Int. Cl.
C07C 381/00 (2006.01)
C07C 233/00 (2006.01)
A01N 43/00 (2006.01)

(52) U.S. Cl. .................... 564/158; 564/200; 514/217.05

(58) Field of Classification Search .................. 564/158
See application file for complete search history.

(56) References Cited

U.S. PATENT DOCUMENTS

| | | | |
|---|---|---|---|
| 1,903,899 A | 4/1933 | Laska et al. |
| 1,909,960 A | 5/1933 | Hitch |
| 3,211,555 A | 10/1965 | Mory et al. |
| 3,328,410 A | 6/1967 | Inman et al. |
| 3,755,332 A | 8/1973 | Wasley et al. |
| 4,367,328 A | 1/1983 | Bertram et al. |
| 4,524,168 A | 6/1985 | Wick |
| 4,749,729 A | 6/1988 | Kohli et al. |
| 5,710,158 A | 1/1998 | Myers et al. |
| 6,127,374 A | 10/2000 | Bridges |
| 6,432,949 B1 | 8/2002 | Brown et al. |
| 6,455,520 B1 | 9/2002 | Brown et al. |
| 6,465,455 B1 | 10/2002 | Brown et al. |
| 6,498,274 B1 | 12/2002 | Brown et al. |
| 6,548,514 B1 | 4/2003 | Brown et al. |
| 6,579,872 B1 | 6/2003 | Brown et al. |
| 6,593,333 B1 | 7/2003 | Cumming |
| 6,686,467 B2 | 2/2004 | Brown et al. |
| 6,716,847 B2 | 4/2004 | Cumming |
| 6,784,174 B1 | 8/2004 | Cumming |
| 6,794,380 B2 | 9/2004 | Brown |
| 2002/0169165 A1 | 11/2002 | Kath et al. |
| 2003/0018029 A1 | 1/2003 | Barker et al. |
| 2003/0105142 A1 | 6/2003 | Brown et al. |
| 2003/0212068 A1 | 11/2003 | Brown et al. |

FOREIGN PATENT DOCUMENTS

| | | |
|---|---|---|
| DE | 522 788 | 3/1931 |
| DE | 28 12 252 | 10/1979 |
| EP | 0 447 891 A1 | 9/1991 |
| EP | 0 566 226 | 10/1993 |
| EP | 0 635 507 | 1/1995 |
| EP | 0 849 256 | 6/1998 |
| EP | 0849256 | 6/1998 |
| EP | 0 945 443 | 9/1999 |
| JP | 61-204221 | 9/1986 |
| JP | 4-177350 A2 | 6/1992 |
| WO | 93/04170 | 3/1993 |
| WO | 95/19774 | 7/1995 |
| WO | 95/35304 | 12/1995 |
| WO | WO 96/01825 | 1/1996 |
| WO | 96/40706 | 12/1996 |
| WO | 97/05878 | 2/1997 |
| WO | WO 97/03967 | 2/1997 |

(Continued)

OTHER PUBLICATIONS

Beilstein Reg. No. 2164595, 1989.

(Continued)

*Primary Examiner*—Sreeni Padmanabhan
*Assistant Examiner*—Timothy E Betton
(74) *Attorney, Agent, or Firm*—Connolly Bove Lodge & Hutz, LLP

(57) ABSTRACT

The invention concerns amide derivatives of the Formula (I) wherein $R^3$ is (1-6C)alkyl or halogeno; Q is aryl or heteroaryl which optionally bears 1, 2, 3 or 4 substituents such as hydroxy, halogeno, trifluoromethyl, cyano, (1-6C)alkyl, (1-6C)alkoxy, halogeno-(1-6C)alkyl, hydroxyl-(1-6C)alkyl, di-[(1-6C)akly]amino-(1-6C)alkyl, hydroxy-(2-6C)alkoxy, (1-6C)alkoxy-(2-6C)alkoxy, di-[(1-6C)alkyl]amino-(2-6C)alkoxy, amino(2-6C)alkylamino, N-(1-6C)alkyl-(1-6C)alkylamino-(2-6C)alkylamino, aryl, aryl-(1-6C)alkoxy, heteroaryl, heteroaryl-(1-6C)alkoxy, heterocyclyl, heterocyclyl-(1-6C)alkyl, heterocyclyloxy and heterocyclyl-(1-6C)alkoxy; p is 0-2 and $R^2$ is a substituent such as hydroxy and halogeno; q is 0-4; and $R^4$ includes optionally substituted aryl, cycloalkyl, heteroaryl and heterocyclyl; or pharmaceutically-acceptable salts or in-vivo-cleavable esters thereof; processes for their preparation, pharmaceutical compositions containing them and their use in the treatment of diseases or medical conditions mediated by cytokines.

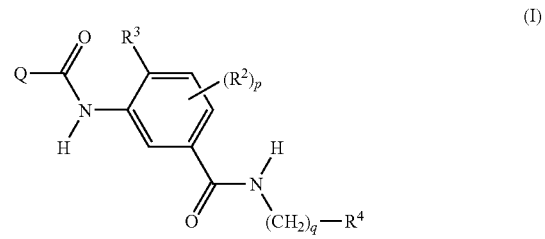

(I)

8 Claims, No Drawings

FOREIGN PATENT DOCUMENTS

| WO | 97/13771 | 4/1997 |
|---|---|---|
| WO | 97/32853 | 9/1997 |
| WO | 97/33883 | 9/1997 |
| WO | 98/06715 | 2/1998 |
| WO | 98/22103 | 5/1998 |
| WO | 99/01439 | 1/1999 |
| WO | 99/15164 | 4/1999 |
| WO | 99/59959 | 11/1999 |
| WO | 99/59960 | 11/1999 |
| WO | 00/07980 | 2/2000 |
| WO | 00/07991 | 2/2000 |
| WO | 00/12485 | 3/2000 |
| WO | 00/12486 | 3/2000 |
| WO | 00/12487 | 3/2000 |
| WO | 00/18738 | 4/2000 |
| WO | 00/20402 | 4/2000 |
| WO | 00/55120 | 9/2000 |
| WO | 00/55153 | 9/2000 |
| WO | 99/56738 | 9/2000 |
| WO | 01/27089 | 4/2001 |

OTHER PUBLICATIONS

Beilstein Reg. No. 3166971, 1990.
Beilstein Reg. No. 3451759, 1990.
Beilstein Reg. No. 3480574, 1990.
Beilstein Reg. No. 3483669, 1990.
Beilstein Reg. No. 3534091, 1990.
Chemical Abstract No. 12076g, vol. 65, 1966.
Chemical Abstract No. 12932a, vol. 51, 1957.
Denny et al., "Potential Antitumour Agents. 29. Quantitative Structure-Activity Relationships for the Antileukemic Bisquaternary Ammonium Heterocycles", Journal of Medicinal Chemistry, Feb. 1979, vol. 22, No. 2, pp. 134-150.
Hamuro et al., "Novel Folding Patterns in a Family of Oligoanthranilamides: . . . Secondary Structures", J. Amer. Chem. Soc., 1997, pp. 10587-10593.
Kelley et al., "Antirhinovirus Activity of 6-Anilino-9-benxyl-2-chloro-9H-purines", J. Med. Chem., 1990, vol. 33, pp. 1360-1363, XP-002140324.
Kozhevnikov, "Synthesis of nitro and amino derivatives of 2-methyl-3-aryl-4-quinazoline", Chemical Abstracts, Abstract No. 19599, vol. 077, No. 3, Jul. 17, 1972, XXP002138275.
Kuboto et al.; Abstract No. 84:45269, Japan 50105558, Aug. 1975.
Myers et al., "The Preparation of SAR of 4-(Anilino), 4-(Phenoxy), and 4-(Thiophenoxy)-Quinazoline: Inhibitors of P56lck and EGF-R Tyrosine Kinase Activity", Bioorganic & Medicinal Chemistry Letters, vol. 7, No. 4, 1997, pp. 417-420.
Parmer et al., "Synthesis of substituted quinazoline hydrazides: the relation between chemical structure and monoamine oxidase inhibitory activity", Chemical Abstract No. 59182, vol. 069, No. 15, Oct. 7, 1968, XP002138276.
Petrova et al., "Determination of the Structure of the Oxidative . . . by Spectroscopic Methods", Journal of Molecular Structure, vol. 142, 1986, pp. 459-462.
Thompson et al., "Tyrosine Kinase Inhibitors. 7.7-Amino-4-(phenylamino- and 7- Amino-4-[(phenylmethyl)amino]purido[4,3-d]pyrimidines: A New Class of Inhibitors of the Tyrosine Kinase Activity of the Epidermal Growth Factor Receptor"; Journal of Medicinal Chemistry, US, American Chemical Society, vol. 39, No. 19, 1995, pp. 3780-3788, XP002140323.
Barton, Clin Immunol Immunopathol. Oct. 1997; 85(1):16-20, PMID: 9325064 [PubMed-indexed for MEDLINE].
Fogarasi et al, Orv. Hetil. Sep. 18, 1994; 135(38):2075-82, PMID: 7936613 [PubMed-Indexed for MEDLINE].
Patent Abstracts of Japan vol. 1997, No. 09, Sep. 30, 1997 & JP 09 124571 A (Japan Tabacco Inc.), May 13, 1997 examples (from p. 56 onwards) in the original document; abstract.
Adams et al., "Search for trypanocides. III. Analogs of suramin.", Chemical Abstracts, vol. 51, 1957, columns 5067 and 5068.
Ando et al., "Producing azo lake pigments"; Chemical Abstract, vol. 106, Abstract No. 215574, Aug. 1988.
Ando et al., Magn. Reson.Chem. 639-45, 1995, Chemical Abstract: 123: 227514, 1995.
Ashton et al., "New Low-Density Lipoprotein Receptor Upregulators Acting via a Novel Mechanism", J. Med. Chem., 1996, vol. 39, pp. 3343-3356.
English et al., Trends Pharmac. Sci., 23, 2002, pp. 40-45.
Boehm et al., Exp. Opin. Ther. Patents, 10(1), 2000, pp. 25-37.
Black et al., Ann Reports, Med. Chem., 32, 1997, pp. 241-250.
Chemical Abstracts, vol. 51, columns 5067 and 5068.
Hanson, "Review—Pulmonary-Allergy, Dermatological, Gastrointestinal & Arthritis—Inhibitors of p38 kinase", Exp. Opin. Ther. Patents, 1997, XP-002086152, pp. 729-733.
Ito et al., Photosensitive material containing microencapsulated hydrazine derivatives; Chemical Abstract, vol. 118, Abstract No. 70021, Jun. 1992.
Lesiak, "New amides of pyrrole-N- and indole-N-caboxylic acids", Chemical Abstracts, No. 126704v, XP-002121335, 1971.
Mühlbach, "Pyrazoles—A Novel Class of Blocking Agents for Isocyanates", Journal of Polymer Science: Part A: Polymer Chemistry, vol. 32, Mar. 1994, pp. 753-765.
Mühlbach, "Pyrazoles—A Novel Class of Blocking Agents for Isocyanates", Journal of Polymer Science: Part A: Polymer Chemistry, vol. 32, Mar. 1994, pp. 753-765.
Sugawara et al., Kogyo Kaguku Zasshi 72(11) 2425-2429, 1969, Chemical Abstract: 72:66514, 1970.
Wang et al., "Low-valent Titanium-induced Reactions of Substituted Nitrobenzenes", J. Chem. Research, 1998, pp. 182-183.
Brown et al., U.S. Appl. No. 09/508,055, filed Mar. 7, 2000, PCT Publication No. WO 99/15164, published Apr. 1, 1999.
Brown et al., U.S. Appl. No. 10/265,736, filed Oct. 8, 2002, PCT Publication No. WO 99/15164, published Apr. 1, 1999.
Brown et al., U.S. Appl. No. 09/674,560, filed Nov. 2, 2000, PCT Publication No. WO 99/59959, published Nov. 25, 1999.
Brown et al., U.S. Appl. No. 10/424,127, filed Nov. 13, 2003, PCT Publication No. WO 99/59959, published Nov. 25, 1999.
Brown, U.S. Appl. No. 09/674,428, filed Nov. 1, 2000, PCT Publication No. WO 99/59960, published Nov. 25, 1999.
Brown et al., U.S. Appl. No. 09/762,107, filed Feb. 2, 2001, PCT Publication No. WO 00/07991, published Feb. 17, 2000.
Brown et al., U.S. Appl. No. 10/192,495, filed Jul. 11, 2002, PCT Publication No. WO 00/07991, published Feb. 17, 2000.
Brown et al., U.S. Appl. No. 09/787,882, filed Mar. 23, 2001, PCT Publication No. WO 00/18738, published Apr. 6, 2000.
Cumming, U.S. Appl. No. 09/787,883, filed Mar. 23, 2001, PCT Publication No. WO 00/20402, published Apr. 13, 2000.
Cumming, U.S. Appl. No. 10/441,084, filed May 20, 2003, PCT Publication No. WO 00/20402, published Apr. 13, 2000.
Brown et al., U.S. Appl. No. 09/936,698, filed Sep. 17, 2001, PCT Publication No. WO 00/55120, published Sep. 21, 2000.
Brown et al., U.S. Appl. No. 10/353,127, filed Jan. 29, 2003, PCT Publication No. WO 00/55120, published Sep. 21, 2000.
Brown et al., U.S. Appl. No. 09/936,758, filed Sep. 17, 2001, PCT Publication No. WO 00/55153, published Sep. 21, 2000.
Cumming, U.S. Appl. No. 09/937,018, filed Sep. 20, 2001, PCT Publication No. WO 00/56738, published Sep. 28, 2000.
Cumming, U.S. Appl. No. 10/070,360, filed Mar. 5, 2002, PCT Publication No. WO 01/27089, published Apr. 19, 2001.

US 7,772,432 B2

AMIDOBENZAMIDE DERIVATIVES WHICH ARE USEFUL AS CYTOKINE INHIBITORS

This is a Divisional of application Ser. No. 09/762,106, filed Feb. 2, 2001 (now U.S. Pat. No. 6,821,965), which is a PCT National Stage of PCT/GB99/02494 filed Jul. 29, 1999, which claims priority to Great Britain Application No. 9816837.0 filed Aug. 4, 1998.

This invention concerns certain amide derivatives which are useful as inhibitors of cytokine mediated disease. The invention also concerns processes for the manufacture of the amide derivatives of the invention, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis and adult respiratory distress syndrome), and in the production and development of various cardiovascular and cerebrovascular disorders such as congestive heart disease, myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. P38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents*, 1997, 7, 729-733. p38 kinase is known to exist in isoforms identified as p38α and p38β.

It is known from *J. Med. Chem.*, 1996, 39, 3343-3356, that certain benzamide derivatives can upregulate the expression of the low density lipoprotein (LDL) receptor in human hepatocyte cells. The disclosed compounds include N-(2-cyclohexylethyl)-3-(4-hydroxybenzamido)-4-methylbenzamide.

It is known from Chemical Abstracts, volume 51, columns 5068 and 5069 that certain compounds are useful as intermediates in the synthesis of compounds with putative trypanocidal activity. The disclosed intermediates include:

3-(4-aminobenzamido)-N-(4-carboxy-3-hydroxyphenyl)-4-methylbenzamide,
N-(4-carboxy-3-hydroxyphenyl)-4-methyl-3-(4-nitrobenzamido)benzamide,
3-(4-aminobenzamido)-4-methyl-N-(2-pyridyl)benzamide,
4-methyl-3-(4-nitrobenzamido)-N-(2-pyridyl)benzamide,
3-(4-aminobenzamido)-4-methyl-N-(2-thiazolyl)benzamide and
4-methyl-3-(4-nitrobenzamido)-N-(2-thiazolyl)benzamide.

The following compounds are also known as chemical intermediates:

3-benzamido-4-chloro-N-(2-fluoroanilino)benzamide (Chemical Abstracts, volume 118, abstract 70021),
3-(2-hydroxy-4-methylbenzamido)-N-4-hydroxyphenyl)-4-methylbenzamide (U.S. Pat. No. 1,903,899),
3-(3-hydroxy-2-naphthoylamino)-4-methyl-N-phenylbenzamide (U.S. Pat. No. 1,909,960)

and 4-chloro-3-(3-hydroxy-2-naphthoylamino)-2-methyl-N-phenylbenzamide (Chemical Abstracts, volume 106, abstract 215574).

The compounds disclosed in the present invention are inhibitors of the production of cytokines such as TNF, in particular of TNFα, and various interleukins, in particular IL-1.

According to one aspect of the present invention there is provided an amide derivative of the Formula I

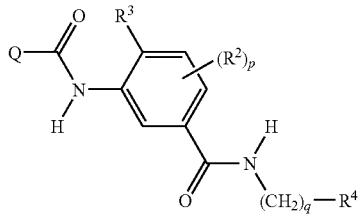

I wherein $R^3$ is (1-6C)alkyl or halogeno;

Q is aryl or heteroaryl which optionally bears 1, 2, 3 or 4 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-3C)alkylenedioxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxyl-1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkylamino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl and heterocyclyl-(2-6C)alkanoylamino, and wherein any of the substituents on Q defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl;

and wherein any aryl, heteroaryl or heterocyclyl group in a substituent on Q may optionally bear 1 or 2 substituents selected from hydroxy, halogeno, (1-6C)alkyl, (1-6C)alkoxy, carboxy, (1-6C)alkoxycarbonyl, N-(1-6C)alkyl-carbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl;

$R^2$ is hydroxy, halogeno, trifluoromethyl, cyano, mercapto, nitro, amino, carboxy, (1-6C)alkoxycarbonyl, (1-6C)alkyl, (2-6C)alkenyl, (2-6C)alkynyl, (1-6C)alkoxy, (1-6C)alkylamino or di-[(1-6C)alkyl]amino;

p is 0, 1 or 2;

q is 0, 1, 2, 3 or 4; and $R^4$ is aryl, aryl-(1-6C)alkoxy, aryloxy, arylamino, N-(1-6C)alkyl-arylamino, aryl-(1-6C)alkylamino, N-(1-6C)alkylaryl-(1-6C)alkylamino, aroylamino, arylsulphonylamino, N-arylsulphamoyl, aryl-(2-6C)alkanoylamino, cycloalkyl, heteroaryl, heteroaryloxy, heteroaryl-(1-6C)alkoxy, heteroarylamino, N-(1-6C)alkylheteroarylamino, heteroaryl-(1-6C)alkylamino, N-(1-6C)alkylheteroaryl-(1-6C)alkylamino, heteroarylcarbonylamino, heteroarylsulphonylamino, N-heteroarylsulphamoyl, heteroaryl-(2-6C)alkanoylamino, heterocyclyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl or heterocyclyl-(2-6C)alkanoylamino and $R^4$ optionally bears 1, 2, 3 or 4 substituents selected from hydroxy, halogeno, tifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-3 C)alkylenedioxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, 1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alklyamino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl and heterocyclyl-(2-6C)alkanoylamino, and wherein any of the substituents on $R^4$ defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl;

and wherein any aryl, heteroaryl or heterocyclyl group in a substituent on $R^4$ may optionally bear 1 or 2 substituents selected from hydroxy, halogeno, (1-6C)alkyl, (1-6C)alkoxy, carboxy, (1-6C)alkoxycabonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl;

or a pharmaceutically-acceptable salt or in-vivo-cleavable ester thereof;

except that the compounds
N-(2-cyclohexylethyl)-3-(4-hydroxybenzamido)-4-methylbenzamide,
3-(4-aminobenzamido)-N-4-carboxy-3-hydroxyphenyl)-4-methylbenzamide,
N-(4-carboxy-3-hydroxyphenyl)-4-methyl-3-(4-nitrobenzamido)benzamide,
3-(4-aminobenzamido)-4-methyl-N-(2-pyridyl)benzamide,
4-methyl-3-(4-nitrobenzamido)-N-(2-pyridyl)benzamide,
3-(4-aminobenzamido)-4-methyl-N-(2-thiazolyl)benzamide,
4-methyl-3-(4-nitrobenzamido)-N-(2-thiazolyl)benzamide,
3-benzamido-4-chloro-N-(2-fluoroanilino)benzamide,
3-(2-hydroxy-4-methylbenzamido)-N-(4-hydroxyphenyl)-4-methylbenzamide,
3-(3-hydroxy-2-naphthoylamino)-4-methyl-N-phenylbenzamide and
4-chloro-3-(3-hydroxy-2-naphthoylamino)-2-methyl-N-phenylbenzamide are excluded.

According to a further aspect of the invention there is provided an amide derivative of the Formula I
wherein $R^3$ is (1-6C)alkyl or halogeno;
Q is aryl or heteroaryl which optionally bears 1, 2, 3 or 4 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-3C)alkylenedioxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)

alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alklyamino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl and heterocyclyl-(2-6C)alkanoylamino, and wherein any aryl, heteroaryl or heterocyclyl group in a substituent on Q may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-4-[(1-6C)alkyl]carbamoyl, (2-6C)alkanoyl, amino, (1-6C)alkylamino and di-[(1-6C)alkyl]amino;

$R^2$ is hydroxy, halogeno, trifluoromethyl, cyano, mercapto, nitro, amino, carboxy, (1-6C)alkoxycarbonyl, (1-6C)alkyl, (2-6C)alkenyl, (2-6C)alkynyl, (1-6C)alkoxy, (1-6C)alkylamino or di-[(1-6C)alkyl]amino;

p is 0, 1 or 2;

q is 0, 1, 2, 3 or 4; and $R^4$ is aryl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, cycloalkyl, heteroaryl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heterocyclyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl or heterocyclyl-(2-6C)alkanoylamino and $R^4$ optionally bears 1, 2, 3 or 4 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-3C)alkylenedioxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alklyamino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-,6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl and heterocyclyl-(2-6C)alkanoylamino, and wherein any aryl, heteroaryl or heterocyclyl group in a substituent on $R^4$ may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino and di-[(1-6C)alkyl]amino;

or a pharmaceutically-acceptable salt or in-vivo-cleavable ester thereof;

except that the compounds:

N-(2-cyclohexylethyl)-3-(4-hydroxybenzamido)-4-methylbenzamide, 3-(4-aminobenzamido)-N-4-carboxy-3-hydroxyphenyl)-4-methylbenzamide, N-(4-carboxy-3-hydroxyphenyl)-4-methyl-3-(4-nitrobenzamido)benzamide, 3-(4-aminobenzamido)-4-methyl-N-(2-pyridyl)benzamide, 4-methyl-3-(4-nitrobenzamido)-N-(2-pyridyl)benzamide, 3-(4-aminobenzamido)-4-methyl-N-(2-thiazolyl)benzamide, 4-methyl-3-(4-nitrobenzamido)-N-(2-thiazolyl)benzamide, 3-benzamido-4-chloro-N-(2-fluoroanilino)benzamide, 3-(2-hydroxy-4-methylbenzamido)-N-(4-hydroxyphenyl)-4-methylbenzamide, 3-(3-hydroxy-2-naphthoylamino)-4-methyl-N-phenylbenzamide and 4-chloro-3-(3-hydroxy-2-naphthoylamino)-2-methyl-N-phenylbenzamide are excluded.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

A suitable value for Q or $R^4$ or for a substituent on Q or $R^4$ when it is aryl or for the aryl group within a substituent on Q or $R^4$ is, for example, phenyl or naphthyl, preferably phenyl.

A suitable value for Q or $R^4$ or for a substituent on Q or $R^4$ when it is heteroaryl or for the heteroaryl group within a substituent on Q or $R^4$ is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofuranyl, quinolyl, isoquinolyl, quinazolinyl, quinoxalinyl, cinnolinyl or naphthyridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl, more preferably isoxazolyl, pyridyl, benzothiazolyl, quinolyl, quinazolinyl, quinoxalinyl or naphthyridinyl.

A suitable value for $R^4$ or for a substituent on Q or $R^4$ when it is heterocyclyl or for the heterocyclyl group within a substituent on Q or $R^4$ is, for example, a non-aromatic saturated or partially saturated 5 to 10 membered monocyclic or bicyclic ring with up to five heteroatoms selected from oxygen, nitrogen and sulphur, for example pyrrolinyl, pyrrolidinyl, morpholinyl, piperidinyl, homopiperidinyl, piperazinyl, homopiperazinyl, dihydropyridinyl, tetrahydropyridinyl, dihydropyrimidinyl or tetrahydropyrimidinyl, preferably pyrrolidin-1-yl, morpholino, piperidino, piperazin-1-yl or homopiperazin-1-yl.

Suitable values for various $R^3$ or $R^2$ groups, or for various substituents on Q or $R^4$ or on an aryl, heteroaryl or heterocyclyl group in a substituent on Q or $R^4$ include:

for halogeno: fluoro, chloro, bromo and iodo;

for (1-6C)alkyl: methyl, ethyl, propyl, isopropyl and tert-butyl;

for (2-6C)alkenyl: vinyl and allyl;

for (2-6C)alkynyl: ethynyl and 2-propynyl;

for (1-6C)alkoxy: methoxy, ethoxy, propoxy, isopropoxy and butoxy;

for (1-6C)alkoxycarbonyl: methoxycarbonyl, ethoxycarbonyl, propoxycarbonyl and tert-butoxycarbonyl;

for N-(1-6C)alkylcarbamoyl: N-methylcarbamoyl, N-ethylcarbamoyl and N-propylcarbamoyl;

for N,N-di-[(1-6C)alkyl]carbamoyl: N,N-dimethylcarbamoyl, N-ethyl-N-methylcarbamoyl and N,N-diethylcarbamoyl;

for (2-6C)alkanoyl: acetyl and propionyl;

for (1-6C)alkylamino: methylamino, ethylamino and propylamino;

for di-[(1-6C)alkyl]amino: dimethylamino, diethylamino and N-ethyl-N-methylamino;

for halogeno-(1-6C)alkyl: fluoromethyl, chloromethyl, bromomethyl, difluoromethyl, dichloromethyl, dibromomethyl, 2-fluoroethyl, 2-chloroethyl and 2-bromoethyl;

for hydroxy-(1-6C)alkyl: hydroxymethyl, 2-hydroxyethyl, 1-hydroxyethyl and 3-hydroxypropyl;

for (1-4C)alkoxy-(1-6C)alkyl: methoxymethyl, ethoxymethyl, 1-methoxyethyl, 2-methoxyethyl, 2-ethoxyethyl and 3-methoxypropyl;

for cyano-(1-6C)alkyl: cyanomethyl, 2-cyanoethyl, 1-cyanoethyl and 3-cyanopropyl;

for amino-(1-6C)alkyl: aminomethyl, 2-aminoethyl, 1-aminoethyl and 3-aminopropyl;

for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;

for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl.

A suitable value for $R^4$ when it is cycloalkyl is, for example, a non-aromatic mono- or bicyclic 4- to 10-membered carbon ring such as cyclobutyl, cyclopentyl, cyclohexyl, cycloheptyl, bicyclo[2.2.1]heptyl and bicyclo[4.4.0]decyl, preferably cyclobutyl, cyclopentyl, cyclohexyl or cycloheptyl.

Suitable values for $R^4$ and suitable values for a substituent on Q or $R^4$ include:

for aryl-(1-6C)alkyl: benzyl, 2-phenylethyl, 2-phenylpropyl and 3-phenylpropyl;

for aryl-(1-6C)alkoxy: benzyloxy and 2-phenylethoxy;
for aryloxy: phenoxy and 2-naphthyloxy;
for arylamino: anilino;
for N-(1-6C)alkyl-arylamino: N-methylanilino and N-ethylanilino;
for aryl-(1-6C)alkylamino: benzylamino, 2-phenethylamino, 2-phenylpropylamino and 3-phenylpropylamino;
for N-(1-6C)alkyl-aryl-(1-6C)alkylamino: N-benzyl-N-methylamino;
for aroylamino: benzamido and 2-naphthoylamino; arylsulphonylamino: benzenesulphonylamido;
for N-arylsulphamoyl: N-phenylsulphamoyl;
for aryl-(2-6C)alkanoylamino: phenylacetamido and 3-phenylpropionamido;
for heteroaryl-(1-6C)alkyl: heteroarylmethyl, 2-heteroarylethyl, 2-heteroarylpropyl and 3-heteroarylpropyl;
for heteroaryl-(1-6C)alkoxy: heteroarylmethoxy and 2-heteroarylethoxy;
for N-(1-6C)alkyl-heteroarylamino: N-methylheteroarylamino;
for heteroaryl-(1-6C)alkylamino: heteroarylmethylamino, 2-heteroarylethylamino and 3-heteroarylpropylamino;
for N-(1-6C)alkyl-heteroaryl-(1-6C)alkylamino: N-methylheteroarylmethylamino and N-methyl-2-heteroarylethylamino;
for heteroaryl-(2-6C)alkanoylamino: heteroarylacetamido and 3-heteroarylpropionamido;
for heterocyclyl-(1-6C)alkyl: heterocyclylmethyl and 2-heterocyclylethyl;
for heterocyclyl-(1-6C)alkoxy: heterocyclylmethoxy and 2-heterocyclylethoxy;
for N-(1-6C)alkyl-heterocyclylamino: N-methylheterocyclylamino;
for heterocyclyl-(1-6C)alkylamino: heterocyclylmethylamino, 2-heterocyclylethylamino and 3-heterocyclylpropylamino;
for N-(1-6C)alkyl-heterocyclyl-(1-6C)alkylamino: N-methylheterocyclylmethylamino and N-methyl-2-heterocyclylethylamino;
for heterocyclyl-(2-6C)alkanoylamino: heterocyclylacetamido and 3-heterocyclylpropionamido;
for (1-3C)alkylenedioxy: methylenedioxy, ethylenedioxy and propylenedioxy;
for (1-6C)alkylthio: methylthio, ethylthio and propylthio;
for (1-6C)alkylsulphinyl: methylsulphinyl, ethylsulphinyl and propylsulphinyl;
for (1-6C)alkylsulphonyl: methylsulphonyl, ethylsulphonyl and propylsulphonyl;
for (2-6C)alkanoyloxy: acetoxy and propionyloxy;
for (1-6C)alkanoylamino: formamido, acetamido and propionamido;
for N-(1-6C)alkylsulphamoyl: N-methylsulphamoyl and N-ethylsulphamoyl;
for N,N-di-[(1-6C)alkyl]sulphamoyl: N,N-dimethylsulphamoyl;
for (1-6C)alkanesulphonylamino: methanesulphonylamino and ethanesulphonylamino;
for N-(1-6C)alkyl-(1-6C)alkanesulphonylamino: N-methylmethanesulphonylamino and N-methylethanesulphonylamino;
for carboxy-(1-6C)alkyl: carboxymethyl, 1-carboxyethyl, 2-carboxyethyl, 3-carboxypropyl and 4-carboxybutyl;
for (1-6C)alkoxycarbonyl-(1-6C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;
for carbamoyl-(1-6C)alkyl: carbamoylmethyl, 1-carbamoylethyl, 2-carbamoylethyl and 3-carbamoylpropyl;
for N-(1-6C)alkylcarbamoyl-(1-6C)alkyl: N-methylcarbamoylmethyl, N-ethylcarbamoylmethyl, N-propylcarbarnoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;
for N,N-di-[(1-6C)alkyl]carbamoyl-(1-6C)alkyl: N,N-dimethylcarbamoylmethyl, N-ethyl-N-methylcarbamoylmethyl, N,N-diethylcarbainoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 3-(N,N-dimethylcarbamoyl)propyl and 4(N,N-dimethylcarbamoyl)butyl;
for halogeno-(2-6C)alkoxy: 2-chloroethoxy, 2-bromoethoxy and 3-chloropropoxy;
for hydroxy-(2-6C)alkoxy: 2-hydroxyethoxy, 2-hydroxy-1-methylethoxy, 3-hydroxypropoxy, 2-hydroxypropoxy and 4hydroxybutoxy;
for (1-6C)alkoxy-(2-6C)alkoxy: 2-methoxyethoxy, 2-ethoxyethoxy, 3-methoxypropoxy, 2-methoxy-1-methylethoxy and 4-ethoxybutoxy;
for cyano-(1-6C)alkoxy: cyanomethoxy, 2-cyanoethoxy and 3-cyanopropoxy;
for carboxy-(1-6C)alkoxy: carboxymethoxy, 1-carboxyethoxy, 2-carboxyethoxy and 3-carboxypropoxy;
for (1-6C)alkoxycarbonyl-(1-6C)alkoxy: methoxycarbonylmethoxy, ethoxycarbonylmethoxy, tert-butoxycarbonylmethoxy, 2-methoxycarbonylethoxy and 3-ethoxycarbonylpropoxy;
for carbamoyl-(1-6C)alkoxy: carbamoylmethoxy and 2-carbamoylethoxy;
for N-(1-6C)alkylcarbamoyl-(1-6C)alkoxy: N-methylcarbamoylmethoxy, 2-(N-ethylcarbamoyl)ethoxy and 3-(N-methylcarbamoyl)propoxy;
for (N,N-di-[(1-6C)alkyl]carbamoyl-(1-6C)alkoxy: N,N-dimethylcarbamoylmethoxy, 2-(N,N-dimethylcarbamoyl)ethoxy and 3-(N,N-diethylcarbamoyl)propoxy;
for amino-(2-6C)alkoxy: 2-aminoethoxy, 2-amino-1-methylethoxy, 3-aminopropoxy, 2-amino-2-methylpropoxy and 4-aminobutoxy;
for (1-6C)alkylamino-(2-6C)alkoxy: 2-methylaminoethoxy, 2-methylamino-1-methylethoxy and 3-ethylaminopropoxy;
for di-[(1-6C)alkyl]amino-(2-6C)alkoxy: 2-dimethylaminoethoxy, 2-diethylaminoethoxy, 2-dimethylaminopropoxy, 2-dimethylamino-2-methylpropoxy, 3-dimethylaminopropoxy and 4-dimethylaminobutoxy;
for halogeno-(2-6C)alkylamino: 2-fluoroethylamino, 2-chloroethylamino, 2-bromoethylamino, 3-fluoropropylamino and 3-chloropropylamino;
for hydroxy-(2-6C)alkylamino: 2-hydroxyethylamino, 3-hydroxypropylamino, 2-hydroxy-2-methylpropylamino and 4-hydroxybutylamino;
for (1-6C)alkoxy-(2-6C)alkylamino: 2-methoxyethylamino, 2-ethoxyethylamino, 3-methoxypropylamino and 3-ethoxypropylamino;
for cyano-(1-6C)alkylamino: cyanomethylamino, 2-cyanoethylamino and 3-cyanopropylamino;
for carboxy-(1-6C)alkylamino: carboxymethylamino, 1-carboxyethylamino, 2-carboxyethylamino and 3-carboxypropylamino;
for (1-6C)alkoxycarbonyl-(1-6C)alkylamino: methoxycarbonylmethylamino, 2-(ethoxycarbonyl)ethylamino and 3-(tert-butoxycarbonyl)propylamino;
for carbamoyl-(1-6C)alkylamino: carbamoylmethylamino and 2-carbamoylethylamino;

for N-(1-6C)alkylcarbamoyl-(1-6C)alkylamino: N-methylcarbamoylmethylamino, N-ethylcarbamoylmethylamino and 2-(N-methylcarbamoyl)ethylamino;

for N N-di-[(1-6C)alkyl]carbamoyl-(1-6C)alkylamino: N,N-dimethylcarbamoyl-methylamino, N,N-diethylcarbamoylmethylamino and 2-(N,N-dimethylcarbamoyl)ethylamino;

for amino-(2-6C)alkylamino: 2-aminoethylamino, 3-aminopropylamino, 2-amino-2-methylpropylamino and 4-aminobutylamino;

for (1-6C)alkylamino-(2-6C)alkylamino: 2-methylaminoethylamino, 2-ethylaminoethylamino, 2-propylaminoethylamino, 3-methylaminopropylamino, 3-ethylaminopropylamino, 2-methylamino-2-methylpropylamino and 4-methylaminobutylamino;

for di-[(1-6C)alkyl]amino-(2-6C)alkylamino: 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino, 2-dimethylamino-2-methylpropylamino and 4-dimethylaminobutylamino;

for N-(1-6C)alkyl-halogeno-(2-6C)alkylamino: N-(2-chloroethyl)-N-methylamino, N-(2-bromoethyl)-N-methylamino and N-(2-bromoethyl)-N-ethylamino;

for N-(1-6C)alkyl-hydroxy-(2-6C)alkylamino: N-(2-hydroxyethyl)N-methylamino, N-(3-hydroxypropyl)-N-methylamino and N-ethyl-N-(2-hydroxyethyl)amino;

for N-(1-6C)alkyl-(1-6C)alkoxy-(2-6C)alkylamino: N-methyl-N-(2-methoxyethyl)amino, N-methyl-N-(3-methoxypropyl)amino and N-ethyl-N-(2-methoxyethyl)amino;

for N-(1-6C)alkyl-cyano-(1-6C)alkylamino: N-(cyanomethyl)-N-methylamino;

for N-(1-6C)alkyl-carboxy-(1-6C)alkylamino: N-carboxymethyl-N-methylamino and N-(2-carboxyethyl)-N-methylamino;

for N-(1-6C)alkyl-(1-6C)alkoxycarbonyl-(1-6C)alkylamino: N-methoxycarbonylmethyl-N-methylamino, N-(2-ethoxycarbonylethyl)-N-ethylamino and N-(2-tert-butoxycarbonylethyl)-N-methylamino;

for N-(1-6C)alkyl-carbamoyl-(1-6C)alkylamino: N-carbamoylmethyl-N-methylamino and N-(2-carbamoylethyl)-N-methylamino;

for N-(1-6C)alkyl-N-(1-6C)alkylcarbamoyl-(1-6C)alkylamino: N-(N-methylcarbamoylmethyl)-N-methylamino, N-(N-ethylcarbamoylmethyl)-N-methylamino and N-[2-N-methylcarbamoyl)ethyl]-N-methylamino;

for N-(1-6C)alkyl-N,N-di-[(1-6C)alkyl]carbamoyl-(1-6C)alkylamino: N,N-dimethylcarbamoylmethyl)-N-methylamino and N-[2-(N,N-dimethylcarbamoyl)ethyl]-N-methylamino;

for N-(1-6C)akyl-amino-(2-6C)alkylamino: N-(2-aminoethyl)-N-methylamino, N-(3-aminopropyl)-N-methylamino and N-(4-aminobutyl)-N-methylamino;

for N-(1-6C)alkyl-(1-6C)alkylamino-(2-6C)alkylamino: N-(2-methylaminoethyl)-N-methylamino, N-(2-ethylaminoethyl)-N-methylamino, N-(3-methylaminopropyl)-N-methylamino, N-(3-ethylaminopropyl)-N-ethylamino and N-(4-methylaminobutyl)-N-methylamino;

for N-(1-6C)alkyl-di-[(1-6C)alkyl]amino-(2-6C)alkylamino: N-(2-dimethylaminoethyl)-N-methylamino, N-(2-diethylaminoethyl)-N-methylamino, N-(3-dimethylaminopropyl)-N-methylamino and N-(4-dimethylaminobutyl)-N-methylamino;

for halogeno-(2-6C)alkanoylamino: 2-chloroacetamido and 3-chloropropionamido;

for hydroxy-(2-6C)alkanoylamino: 2-hydroxyacetamido and 3-hydroxypropionamido;

for (1-6C)alkoxy-(2-6C)alkanoylamino: 2-methoxyacetamido and 3-methoxypropionamido;

for cyano-(2-6C)alkanoylamino: 2-cyanoacetamido and 3-cyanopropionamido;

for carboxy-(2-6C)alkanoylamino: 2-carboxyacetamido and 3-carboxypropionamido;

for (1-6C)alkoxycarbonyl-(2-6C)alkanoylamino: 2-methoxycarbonylacetamido, 2-(tert-butoxycarbonyl)acetamido and 3-methoxycarbonylpropionamido;

for carbamoyl-(2-6C)alkanoylamino: 2-carbamoylacetamido, 3-carbamoylpropionamido and 4-carbamoylbutyramido;

for N-(1-6C)alkylcarbamoyl-(2-6C)alkanoylamino: 2-(N-methylcarbamoyl)acetamido and 3-(N-ethylcarbamoyl)propionamido;

for N,N-di-[(1-6C)alkyl]carbamoyl-(2-6C)alkanoylamino: 2-(N,N-dimethylcarbamoyl)acetamido, 2-(N,N-diethylcarbamoyl)acetamido and 3-(N,N-dimethylcarbamoyl)propionamido;

for amino-(2-6C)alkanoylamino: 2-aminoacetamido, 2-aminopropionamido and 3-aminopropionamido;

for (1-6C)alkylamino-(2-6C)alkanoylamino: 2-methylaminoacetamido, 2-ethylaminoacetamido, 2-methylaminopropionamido and 3-methylaminopropionamido;

for di-[(1-6C)alkyl]amino-(2-6C)alkanoylamino: 2-dimethylaminoacetamido, 2-diethylaminoacetamido, 2-dimethylaminopropionamido and 3-dimethylaminopropionamido.

When, as defined hereinbefore, any of the substituents on Q or $R^4$ which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl, suitable substituents so formed include, for example, substituted heterocyclyl-(1-6C)alkoxy groups such as 2-hydroxy-3-piperidinopropoxy and 2-hydroxy-3-morpholinopropoxy, substituted amino-(2-6C)alkoxy groups such as 3-amino-2-hydroxypropoxy, substituted (1-6C)alkylamino-(2-6C)alkoxy groups such as 2-hydroxy-3-methylaminopropoxy, substituted di-[(1-6C)alkyl]amino-(2-6C)alkoxy groups such as 3-dimethylamino-2-hydroxypropoxy, 3-[N-(3-dimethylaminopropyl)-N-methylamino]propoxy and 3-[N-(3-dimethylaminopropyl)-N-methylamino]-2-hydroxypropoxy, substituted heterocyclyl-(1-6C)alkylamino groups such as 2-hydroxy-3-piperidinopropylamino and 2-hydroxy-3-morpholinopropylamino, substituted amino-(2-6C)alkylamino groups such as 3-amino-2-hydroxypropylamino, substituted (1-6C)alkylamino-(2-6C)alkylamino groups such as 2-hydroxy-3-methylaminopropylamino, substituted di-[(1-6C)alkyl]amino-(2-6C)alkylamino groups such as 3-dimethylamino-2-hydroxypropylamino, 3-[N-(3-dimethylaminopropyl)-N-methylamino]propylamino and 3-[N-(3-dimethylaminopropyl)N-methylamino]-2-hydroxypropylamino, substituted (1-6C)alkylamino-(1-6C)alkyl groups such as 2-methoxyethylaminomethyl, 3-dimethylaminopropylaminomethyl, 2-morpholinoethylaminomethyl, 2-piperazin-1-ylethylaminomethyl and 3-morpholinopropylaminomethyl, and substituted di-[(1-6C)alkyl]amino-(1-6C)alkyl groups such as N-(3-dimethylaminopropyl)-N-methylaminomethyl.

A suitable pharmaceutically-acceptable salt of a compound of the Formula I is, for example, an acid-addition salt of a compound of the Formula I which is sufficiently basic, for example an acid-addition salt with an inorganic or organic acid such as hydrochloric, hydrobromic, sulphuric, trifluoroacetic, citric or maleic acid; or, for example a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl) amine.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, *Advanced Drug Delivery Reviews*, 8, 1-38 (1992);
d) H. Bundgaard, et al., *Journal of Pharmaceutical Sciences*, 77, 285 (1988); and
e) N. Kakeya, et al., *Chem. Pharm. Bull.*, 32, 692 (1984).

Examples of such pro-drugs may be used to form in-vivo-cleavable esters of a compound of the Formula I. An in-vivo-cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolan-2-ylmethyl esters, for example 5-methyl-1,3-dioxolan-2-ylmethyl; and (1-6C)alkoxycarbonyloxyethyl esters, for example 1-methoxycarbonyloxyethyl; and may be formed at any carboxy group in the compounds of this invention.

Particular novel compounds of the invention include, for example, amide derivatives of the Formula I, or pharmaceutically-acceptable salts thereof, wherein:
(a) $R^3$ is (1-6C)alkyl such as methyl, ethyl, propyl and isopropyl, preferably methyl and ethyl, more preferably methyl; and Q, $R^2$, $R^4$, p and q have any of the meanings defined hereinbefore or in this section relating to particular novel compounds of the invention;
(b) $R^3$ is halogeno such as fluoro, bromo and chloro, preferably chloro and bromo, more preferably chloro; and Q, $R^2$, $R^4$, p and q have any of the meanings defined hereinbefore or in this section relating to particular novel compounds of the invention;
(c) Q is phenyl which bears 1, 2 or 3 substituents selected from hydroxy, halogeno, trifluoromethyl, cyano, nitro, amino, carboxy, (1-6C)alkyl, (1-6C)alkoxy, (1-3 C)alkylenedioxy, (1-6C)alkylamino, di-[(1-6C)alkyl]amino, (1-6C)alkoxycarbonyl, (2-6C)akanoyl, halogeno-(1-6C)alkyl, (1-6C)alkoxy-(1-6C)alkyl, amino-(1-6C)alkyl, (1-6C)alkylamino-(1-6C)alkyl, di-[(1-6C)alkyl]amino-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, amino-(2-6C)alkoxy, (1-6C)alkylamino-(2-6C)alkoxy, di-[(1-6C)alkyl]amino-(2-6C)alkoxy, pyridyl-(1-6C)alkyl, imidazolyl-(1-6C)alkyl, pyridyl-(1-6C)alkoxy, imidazolyl-(1-6C)alkoxy, pyrrolidinyl, piperidinyl, morpholinyl, piperazinyl, 4-(1-6C)alkylpiperazinyl, 4-(2-6C)alkanoylpiperazinyl, pyrrolidinyl-(1-6C)alkyl, piperidinyl-(1-6C)alkyl, morpholinyl-(1-6C)alkyl, piperazinyl-(1-6C)alkyl, 4-(1-6C)alkylpiperazinyl-(1-6C)alkyl, 4-(2-6C)alkanoylpiperazinyl-(1-6C)alkyl, pyrrolidinyloxy, piperidinyloxy, 1-(1-6C)alkylpiperidinyloxy, pyrrolidinyl-(2-6C)alkoxy, piperidinyl-(2-6C)alkoxy, morpholinyl-(2-6C)alkoxy, piperazinyl-(2-6C)alkoxy, 4-(1-6C)alkylpiperazinyl-(2-6C)alkoxy and 4-(2-6C)alkanoylpiperazinyl-(2-6C)alkoxy; and $R^2$, $R^3$, $R^4$, p and q have any of the meanings defined hereinbefore or in this section relating to particular novel compounds of the invention;
(d) Q is a heteroaromatic 5- or 6-membered monocyclic ring or a 9- or 10-membered bicyclic ring with up to five ring heteroatoms selected from oxygen, nitrogen and sulphur which optionally bears 1 or 2 substituents selected from hydroxy, halogeno, trifluoromethyl, cyano, nitro, amino, carboxy, (1-6C)alkyl, (1-6C)alkoxy, (1-6C)alkylamino, di-[(1-6C)alkyl]amino and (1-6C)alkoxycarbonyl; and $R^2$, $R^3$, $R^4$, p and q have any of the meanings defined hereinbefore or in this section relating to particular novel compounds of the invention;
(e) Q is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, halogeno, trifluoromethyl, cyano, nitro, amino, carboxy, (1-6C)alkyl, (1-6C)alkoxy, (1-6C)alkylamino, di-[(1-6C)alkyl]amino and (1-6C)alkoxycarbonyl; and $R^2$, $R^3$, $R^4$, p and q have any of the meanings defined hereinbefore or in this section relating to particular novel compounds of the invention;
(f) Q is 2- or 3-furyl, 2- or 3-thienyl, 2-, 4- or 5-oxazolyl, 3-, 4- or 5-isoxazolyl, 2-, 4- or 5-imidazolyl, 3- or 4-pyrazolyl, 2-, 4- or 5-thiazolyl, 3-, 4- or 5-isothiazolyl, 2-, 3- or 4-pyridyl, 3- or 4-pyridazinyl, 2-, 4- or 5-pyrimidinyl, 2-pyrazinyl, 2-, 3-, 5- or 6-benzofuranyl, 2-, 3-, 5- or 6-indolyl, 2-, 3-, 5- or 6-benzothienyl, 2-, 5- or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6- or 7-quinolyl, 3-, 6- or 7-isoquinolyl, 2-, 6- or 7-quinazolinyl, 2-, 6- or 7-quinoxalinyl, or 1,8-naphthyridin-2-yl or 1,8-naphthyridin-3-yl which optionally bears 1 or 2 substituents selected from hydroxy, halogeno, trifluoromethyl, cyano, nitro, amino, carboxy, (1-6C)alkyl, (1-6C)alkoxy, (1-6C)alkylamino, di-[(1-6C)alkyl]amino and (1-6C)alkoxycarbonyl; and $R^2$, $R^3$, $R^4$, p and q have any of the meanings defined hereinbefore or in this section relating to particular novel compounds of the invention;
(g) q is 0, and $R^4$ is phenyl which bears 1, 2 or 3 substituents selected from hydroxy, halogeno, trifluoromethyl, cyano, amino, (1-6C)alkyl, (1-6C)alkoxy, (1-3C)alkylenedioxy, (1-6C)alkylamino, di-[(1-6C)alkyl]amino, (2-6C)alkanoyl, halogeno-(1-6C)alkyl, (1-6C)alkoxy-(1-6C)alkyl, (1-6C)alkylamino-(1-6C)alkyl, di-[(1-6C)alkyl]amino-(1-6C)alkyl, halogeno-(2-6C)alkoxy, hydroxy-(2-6C)alkoxy, (1-6C)alkoxy-(2-6C)alkoxy, cyano-(2-6C)alkoxy, carboxy-(2-6C)alkoxy, (1-6C)alkoxycarbonyl-(1-6C)alkoxy, amino-(2-6C)alkoxy, (1-6C)alkylamino-(2-6C)alkoxy, di-[(1-6)alkyl]amino-(2-6C)alkoxy, halogeno-(2-6C)alkylamino, hydroxy-(2-6C)alkylamino, (1-6C)alkoxy-(2-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(2-6C)alkylamino, N-(1-6C)alkyl-hydroxy-(2-6C)alkylamino, N-(1-6C)alkyl-(1-6C)alkoxy-(2-6C)alkylamino, N-(1-6C)alkylamino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, phenyl, benzyl, benzyloxy, pyridyl, imidazolyl, pyridyl-(1-6C)alkyl, imidazolyl-(1-6C)alkyl, pyridyl-(1-6C)alkoxy, imidazolyl-(1-6C)alkoxy, pyrrolidinyl, piperidinyl, morpholinyl, piperazinyl, 4-(1-6C)alkylpiperazinyl, 4-(2-6C)alkanoylpiperazinyl, pyrrolidinyl-(1-6C)alkyl, piperidinyl-(1-6C)alkyl, morpholinyl-(1-6C)alkyl, piperazinyl-(1-6C)alkyl, 4-(1-6C)alkylpiperazinyl-(1-6C)alkyl, 4-(2-6C)alkanoylpiperazinyl-(1-6C)alkyl, pyrrolidinyloxy, piperidinyloxy, 1-(1-6C)alkylpiperidinyloxy, pyrrolidinyl-(2-6C)alkoxy, piperidinyl-(2-6C)alkoxy, morpholinyl-(2-6C)alkoxy, piperazinyl-(2-6C)alkoxy, 4-(1-6C)alkylpiperazinyl-(2-6C)alkoxy and 4(2-6C)alkanoylpiperazinyl-(2-6C)alkoxy; and $R^2$, $R^3$, $R^4$, p and q have any of the meanings defined hereinbefore or in this section relating to particular novel compounds of the invention;

(h) p is 0; and Q, $R^3$, $R^4$ and q have any of the meanings defined hereinbefore or in this section relating to particular novel compounds of the invention;

(i) q is 0, and $R^4$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, halogeno, trifluoromethyl, cyano, nitro, amino, carboxy, (1-6C)alkyl, (1-6C)alkoxy, (1-6C)alkylamino, di-[(1-6C)alkyl]amino and (1-6C)alkoxycarbonyl; and Q, $R^2$, $R^3$ and p have any of the meanings defined hereinbefore or in this section relating to particular novel compounds of the invention;

(j) q is 0, and $R^4$ is 2- or 3-furyl, 2- or 3-thienyl, 2- , 4- or 5-oxazolyl, 3- , 4- or 5-isoxazolyl, 2-, 4- or 5-imidazolyl, 3- or 4-pyrazolyl, 2-, 4- or 5-thiazolyl, 3-, 4- or 5-isothiazolyl, 2-, 3- or 4-pyridyl, 3- or 4-pyridazinyl, 2- , 4- or 5-pyrimidinyl, 2-pyrazinyl, 2-, 3-, 5- or 6-benzofuranyl, 2-, 3-, 5- or 6-indolyl, 2-, 3-, 5- or 6-benzothienyl, 2-, 5- or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6- or 7-quinolyl, 3-, 6- or 7-isoquinolyl, 2-, 6- or 7-quinazolinyl, 2-, 6- or 7-quinoxalinyl, or 1,8-naphthyridin-2-yl or 1,8-naphthyridin-3-yl which optionally bears 1 or 2 substituents selected from hydroxy, halogeno, trifluoromethyl, cyano, nitro, amino, carboxy, (1-6C)alkyl, (1-6C)alkoxy, (1-6C)alkylamino, di-[(1-6C)alkyl]amino and (1-6C)alkoxycarbonyl; and Q, $R^2$, $R^3$ and p have any of the meanings defined hereinbefore or in this section relating to particular novel compounds of the invention;

(k) q is 0, and $R^4$ is 4- or 5-oxazolyl, 4- or 5-isoxazolyl, 4- or 5-thiazolyl, 4- or 5-isothiazolyl, 2-, 3- or 4-pyridyl, 5- or 6-benzofuranyl, 5- or 6-benzothienyl, 5- or 6-benzothiazolyl, 2-, 3-, 6- or 7-quinolyl, 2-, 6- or 7-quinazolinyl, 2-, 6- or 7-quinoxalinyl, 1,8-naphthyridin-2-yl or 1,8-naphthyridin-3-yl which optionally bears 1, 2 or 3 substituents selected from hydroxy, fluoro, chloro, trifluoromethyl, cyano, methyl, ethyl, methoxy and ethoxy; and Q, $R^2$, $R^3$ and p have any of the meanings defined hereinbefore or in this section relating to particular novel compounds of the invention;

(l) q is 1, 2, 3 or 4, and $R^4$ is cycloalkyl; and Q, $R^2$, $R^3$ and p have any of the meanings defined hereinbefore or in this section relating to particular novel compounds of the invention; and (m) q is 0 and $R^4$ is phenyl which is optionally substituted as defined hereinbefore; and Q, $R^2$, $R^3$ and p have any of the meanings defined hereinbefore or in this section relating to particular novel compounds of the invention.

In a further aspect of the present invention there is provided a group of novel compounds of the Formula I wherein Q is substituted by a basic substituent selected from the substituents for Q defined hereinbefore and $R^4$ is a phenyl or heteroaryl group as defined hereinbefore which also bears a basic substituent selected from the substituents for $R^4$ defined hereinbefore. This group of compounds possesses improved TNFα inhibitory potency in one or both of the PBMC and Human Whole Blood (HWB) tests described hereinafter.

Suitable basic substituents include, for example, amine derivatives such as amino, (1-6C)alkylamino, di-[(1-6C)alkyl]amino-(1-6C)alkyl, di-[(1-6C)alkyl]amino-(2-6C)alkoxy, di-[(1-6C)alkyl]amino-(2-6C)alkylamino, a heteroaryl group such as a nitrogen-containing heteroaryl group, for example imidazolyl and pyridyl and a heterocyclyl group such as a nitrogen-containing heterocyclyl group, for example morpholinyl or piperidinyl.

A preferred compound of the invention is an amide derivative of the Formula I wherein $R^3$ is methyl, ethyl, chloro or bromo;

Q is phenyl which bears 1, 2 or 3 substituents selected from hydroxy, fluoro, chloro, trifluoromethyl, cyano, carboxy, methyl, ethyl, propyl, methoxy, ethoxy, methylenedioxy, methoxycarbonyl, ethoxycarbonyl, tert-butoxycarbonyl, acetyl, propionyl, chloromethyl, methoxymethyl, methylaminomethyl, ethylaminomethyl, dimethylaminomethyl, diethylaminomethyl, 2-chloroethoxy, 3-chloropropoxy, 2-hydroxyethoxy, 3-hydroxypropoxy, 2-methoxyethoxy, 2-ethoxyethoxy, 3-methoxypropoxy, 3-ethoxypropoxy, cyanomethoxy, carboxymethoxy, methoxycarbonylmethoxy, ethoxycarbonylmethoxy, tert-butoxycarbonylmethoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridylmethoxy, 2-(imidazol-1-yl)ethoxy, 3-(imidazol-1-yl)propoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy, or Q is furyl, thienyl, oxazolyl, isoxazolyl, imidazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, quinolyl, isoquinolyl, quinazolinyl, quinoxalinyl or naphthyridinyl which optionally bears 1 or 2 substituents selected from hydroxy, fluoro, 5 chloro, trifluoromethyl, cyano, methyl, ethyl, methoxy and ethoxy;

p is 0;

q is 0; and $R^4$ is phenyl which bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, acetyl, propionyl, chloromethyl, methoxymethyl, 2-methoxyethyl, methylaminomethyl, ethylaminomethyl, dimethylaminomethyl, diethylaminomethyl, 2-chloroethoxy, 3-chloropropoxy, 2-hydroxyethoxy, 3-hydroxypropoxy, 2-methoxyethoxy, 2-ethoxyethoxy, 3-methoxypropoxy, 3-ethoxypropoxy, cyanomethoxy, carboxymethoxy, methoxycarbonylmethoxy, ethoxycarbonylmethoxy, tert-butoxycarbonylmethoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-chloroethylamino, 2-hydroxyethylamino, 2-methoxyethylamino, 2-ethoxyethylamino, 2-aminoethylamino, 2-methylaminoethylamino, 2-ethylaminoethylamino, 2-dimethylaminoethylamino, 2-diethylaminoethylamino, N-(2-chloroethyl)-N-methylamino, N-(2-hydroxyethyl)-N-methylamino, N-(2-methoxyethyl)-N-methylamino, N-(2-methoxyethyl)-N-methylamino, N-(2-aminoethyl)-N-methylamino, N-(2-methylaminoethyl)-N-methylamino, N-(2-dimethylaminoethyl)-N-methylamino, N-(3-aminopropyl)-N-methylamino, N-(3-methylaminopropyl)-N-methylamino, N-(3-ethylaminopropyl) N-methylamino, N-(3-dimethylaminopropyl)-N-methylamino, N-(3-diethylaminopropyl)-N-methylamino, phenyl, benzyl, benzyloxy, 2-pyridylmethoxy, 2imidazol-1-yl)ethoxy, 3-(imidazol-1-yl)propoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

A further preferred compound of the invention is an amide derivative of the Formula I wherein $R^3$ is methyl or chloro;

Q is phenyl which bears 1, 2 or 3 substituents selected from hydroxy, fluoro, chloro, cyano, o carboxy, methyl, ethyl, propyl, methoxy, ethoxy, methylenedioxy, methoxycarbonyl, ethoxycarbonyl, tert-butoxycarbonyl, acetyl, propionyl, chloromethyl, dimethylaminomethyl, diethylaminomethyl, 2-methoxyethoxy, 2-ethoxyethoxy, 3-methoxypropoxy, 3-ethoxypropoxy, methoxycarbonylmethoxy, ethoxycarbonylmethoxy, tert-butoxycarbonylmethoxy, 2-dimethylaminoethoxy, 2-diethylaminoethoxy, 3-dimethylaminopropoxy, 3-diethylaminopropoxy, 2-pyridylmethoxy, 2-(imidazol-1-yl)ethoxy, 3-(imidazol-1-yl)propoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy, or Q is 2-furyl, 2-thienyl, 2-oxazolyl, 3-isoxazolyl, 2-imidazolyl, 2-thiazolyl, 3-isothiazolyl, 2-, 3- or 4-pyridyl, 3-pyridazinyl, 2- or 4-pyrimidinyl, 2-pyrazinyl, 5- or 6-benzofuranyl, 5- or 6-indolyl, 5- or 6-benzothienyl, 5- or 6-benzoxazolyl, 5- or 6-benzimidazolyl, 5- or 6-benzothiazolyl, 5- or 6-indazolyl, 2-, 6- or 7-quinolyl, 6- or 7-isoquinolyl, 2-, 6- or 7-quinazolinyl, 2-, 6- or 7-quinoxalinyl or 1,8-naphthyridin-3-yl which optionally bears 1 or 2 substituents selected from hydroxy, chloro, methyl and ethyl;

p is 0;

q is 0; and $R^4$ is phenyl which bears 1 or 2 substituents selected from hydroxy, fluoro, chloro, cyano, amino, methyl, methoxy, methylamino, dimethylamino, 2-chloroethoxy, 3-chloropropoxy, 2-hydroxyethoxy, 3-hydroxypropoxy, 2-methoxyethoxy, 3-methoxypropoxy, carboxymethoxy, methoxycarbonylmethoxy, ethoxycarbonylmethoxy, tert-butoxycarbonylmethoxy, 2-dimethylaminoethoxy, 2-diethylaminoethoxy, 3-dimethylaminopropoxy, 3-diethylaminopropoxy, 2-pyridylmethoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-I -ylmethyl, 4-methylpiperazin-1-ylmethyl, 4-acetylpiperazin-1-ylmethyl, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-I -yl)ethoxy and 3-(4-acetylpiperazin-1-yl)propoxy;

or a pharmaceutically-acceptable salt thereof

A further preferred compound of the invention is an amide derivative of the Formula I wherein $R^3$ is methyl or chloro;

Q is phenyl which bears 1, 2 or 3 substituents selected from hydroxy, fluoro, chloro, cyano, carboxy, methyl, ethyl, propyl, methoxy, ethoxy, methylenedioxy, methoxycarbonyl, ethoxycarbonyl, tert-butoxycarbonyl, acetyl, propionyl, chloromethyl, dimethylaminomethyl, diethylaminomethyl, 2-methoxyethoxy, 2-ethoxyethoxy, 3-methoxypropoxy, 3-ethoxypropoxy, methoxycarbonylmethoxy, ethoxycarbonylmethoxy, tert-butoxycarbonylmethoxy, 2-dimethylaminoethoxy, 2-diethylaminoethoxy, 3-dimethylaminopropoxy, 3-diethylaminopropoxy, 2-pyridylmethoxy, 2-(imidazol-1-yl)ethoxy, 3-(imidazol-1-yl)propoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

p is 0;

q is 1 or 2; and $R^4$ is cyclobutyl, cyclopentyl or cyclohexyl;

or a pharmaceutically-acceptable salt thereof.

A more preferred compound of the invention is an amide derivative of the Formula I wherein $R^3$ is methyl or chloro;

Q is phenyl which bears 1, 2 or 3 substituents selected from hydroxy, cyano, carboxy, methyl, ethyl, propyl, methoxy, ethoxy, acetyl and 2-methoxyethoxy;

p is 0;

q is 0; and $R^4$ is phenyl which bears 1 or 2 substituents selected from chloro, cyano and dimethylamino;
or a pharmaceutically-acceptable salt thereof.

A further more preferred compound of the invention is an amide derivative of the Formula I
wherein $R^3$ is methyl or chloro;
Q is 3-isoxazolyl, 3-pyridyl or 6-quinolyl which optionally bears a substituent selected from chloro and methyl;
p is 0;
q is 0; and
$R^4$ is phenyl which bears a dimethylamino substituent;
or a pharmaceutically-acceptable salt thereof A further more preferred compound of this aspect of the invention is an amide derivative of the Formula I
wherein $R^3$ is methyl or chloro;
Q is phenyl which bears a substituent selected from dimethylaminomethyl, diethylaminomethyl, N-butyl-N-methylaminomethyl, 2-methylaminoethoxy, 2-diethylaminoethoxy, 2-diisopropylaminoethoxy, 3-dimethylaminopropoxy, 3-diethylaminopropoxy, 3-diisopropylaminopropoxy, pyrrolidin-1-ylmethyl, 3-hydroxypyrrolidin-1-ylmethyl, morpholinomethyl, piperidinomethyl, homopiperidinomethyl, piperazin-1-ylmethyl, homopiperazin-1-ylmethyl, 4-methylpiperazin-1-ylmethyl, 4-methylhomopiperazin-1-ylmethyl, 4-ethylpiperazin-1-ylmethyl, 4-ethylhomopiperazin-1-ylmethyl, 4-isopropylpiperazin-1-ylmethyl, 4-(2-hydroxyethyl)piperazin-1-ylmethyl, 2-pyridylmethoxy, pyrrolidin-3-yloxy, 1-methylpyrrolidin-3-yloxy, piperidin-3-yloxy, 1-methylpiperidin-3-yloxy, homopiperidin-3-yloxy, 1-methylhomopiperidin-3-yloxy, piperidin-4-yloxy, 1-methylpiperidin-4-yloxy, homopiperidin-4-yloxy, 1-methylhomopiperidin-4-yloxy, pyrrolidin-3-ylmethoxy, 1-methylpyrrolidin-3-ylmethoxy, piperidin-3-ylmethoxy, 1-methylpiperidin-3-ylmethoxy, homopiperidin-3-ylmethoxy, 1-methylhomopiperidin-3-ylmethoxy, piperidin-4-ylmethoxy, 1-methylpiperidin-4-ylmethoxy, homopiperidin-4-ylmethoxy, 1-methylhomopiperidin-4-ylmethoxy, 2-(pyrrolidin-1-yl)ethoxy, 3-(pyrrolidin-1-yl)propoxy, 2-(N-methylpyrrolidin-2-yl)ethoxy, 3-(N-methylpyrrolidin-2-yl)propoxy, 2-piperidinoethoxy, 3-piperidinopropoxy, 2-morpholinoethoxy, 3-morpholinopropoxy, 2-piperazin-1-ylethoxy, 2-homopiperazin-1-ylethoxy, 3-piperazin-1-ylpropoxy, 3-homopiperazin-1-ylpropoxy, 2-(4-methylpiperazin-1-yl)ethoxy, 2-(4-methylhomopiperazin-1-yl)ethoxy, 3-(4-methylpiperazin-1-yl)propoxy, 3-(4-methylhomopiperazin-1-yl)propoxy, 2-(4-acetylpiperazin-1-yl)ethoxy, 3-(4-acetylpiperazin-1-yl)propoxy, 2-methoxyethylaminomethyl, 3-methoxypropylaminomethyl, 2-aminoethylaminomethyl, 3-aminopropylaminomethyl, 3-dimethylamino-2,2-dimethylpropylaminomethyl, 2-methylaminoethylaminomethyl, 3-methylaminopropylaminomethyl, 2-dimethylaminoethylaminomethyl, 3-dimethylaminopropylaminomethyl, N-(2-methylaminoethyl)-N-methylaminomethyl, N-(3-methylaminopropyl)-N-methylaminomethyl, N-(2-dimethylaminoethyl)-N-methylaminomethyl, N-(3-dimethylaminopropyl)-N-methylaminomethyl and 3-morpholinopropylaminomethyl, and Q is optionally substituted with a further substituent selected from methyl and methoxy;
p is 0;
q is 0; and
$R^4$ is phenyl which is substituted at the 3-position with a substituent selected from dimethylamino, diethylamino, pyrrolidin-1-yl, piperidino, morpholino, piperazin-1-yl, homopiperazin-1-yl, 4-methylpiperazin-1-yl and 4-methylhomopiperazin-1-yl and $R^4$ is optionally substituted with a further substituent selected from fluoro, chloro, cyano, methyl and trifluoromethyl;
or a pharmaceutically-acceptable salt thereof A further more preferred compound of this aspect of the invention is an amide derivative of the Formula I
wherein $R^3$ is methyl or chloro;
Q is 3-pyridyl or 4-pyridyl which bears a substituent selected from 2-aminoethylamino, 3-aminopropylamino, 2-amino-2-methylpropylamino, 4-aminobutylamino, 2-methylaminoethylamino, 2-ethylaminoethylamino, 3-methylaminopropylamino, 4-methylaminobutylamino, 2-dimethylaminoethylamino, 2-diethylaminoethylamino, 3-dimethylaminopropylamino, 4-dimethylaminobutylamino, N-(2-methylaminoethyl)-N-methylamino, N-(3-methylaminopropyl)-N-methylamino, N-(4-methylaminobutyl)-N-methylamino, N-(2-dimethylaminoethyl)-N-methylamino, N-(3-dimethylaminopropyl)-N-methylamino, N-(4-dimethylaminobutyl)-N-methylamino, pyrrolidin-1-yl, 3-hydroxypyrrolidin-1-yl, morpholino, piperidino, homopiperidino, piperazin-1-yl, homopiperazin-1-yl, 4-methylpiperazin-1-yl, 4-ethylpiperazin-1-yl, 4-(2-hydroxyethyl)piperazin-1-yl, 4-methylhomopiperazin-1-yl, 3-morpholinopropylamino or 2-(1-methylpyrrolidin-2-yl)ethylamino;
p is 0;
q is 0; and
$R^4$ is phenyl which is substituted at the 3-position with a substituent selected from dimethylamino, diethylamino, pyrrolidin-1-yl, piperidino, morpholino, piperazin-1-yl, homopiperazin-1-yl, 4-methylpiperazin-1-yl and 4-methylhomopiperazin-1-yl and $R^4$ is optionally substituted with a further substituent selected from fluoro, chloro, cyano, methyl and trifluoromethyl;
or a pharmaceutically-acceptable salt thereof A particular preferred compound of the invention is, for example:
N-(3-dimethylaminophenyl)-4-methyl-3-(4-propylbenzamido)benzamide,
3-(3,4-dimethoxybenzamido)-N-(3-dimethylaminophenyl)-4-methylbenzamide,
3-(4-butoxybenzamido)-N-(3-dimethylamino-6phenyl)-4-methylbenzamide,
4-chloro-N-(3-dimethylaminophenyl)-3-(4-propylbenzamido)benzamide,
3-(4-carboxybenzamido)-N-(3-dimethylaminophenyl)-4-methylbenzamide,
N-(3,4-dichlorobenzyl)-3-(3,4,5-trimethoxybenzamido)-4-methylbenzamide,
N-(2-cyclohexylethyl)-3-(3,4-dimethoxybenzamido)-4-methylbenzamide,
N-(3-dimethylaminophenyl)-4-methyl-3-(6-quinolylcarbonylamino)benzamide or
4-chloro-N-(3-dimethylaminophenyl)-3-(6-quinolylcarbonylamino)benzamide;
or a pharmaceutically-acceptable salt thereof.

A further particular preferred compound of the invention is, for example:
4-methyl-N-(3-morpholinophenyl)-3-(3-piperidin-4-yloxy)benzamido)benzamide,
4-chloro-N-(3-fluoro-5-morpholinophenyl)-3-[3-(1-methylhomopiperidin-4-yloxy)benzamido]benzamide,
3-(2-diisopropylaminoethoxybenzamido)-4-methyl-N-(3-morpholinophenyl)benzamide,
3-(4-diethylaminomethylbenzamido)-4-methyl-N-(3-morpholinophenyl)benzamide, 4-methyl-3-[3-(4-methylhomopiperazin-1-ylmethyl)benzamido]-N-3-morpholinophenyl)-benzamide, 4-methyl-3-[3-(4-methylpiperazin-1-ylmethyl)benzamido]-N-(3-morpholinophenyl)-benzamide and 3-[6-(2-amino-2-methylpropylamino)pyrid-3-ylcarbonylamino]-4-chloro-N-(3-fluoro-5-morpholinophenyl)benzamide;

or a pharmaceutically-acceptable salt thereof.

An amide derivative of the Formula I, or a pharmaceutically-acceptable salt or in-vivo-cleavable ester thereof, may be prepared by any process known to be applicable to the preparation of chemically-related compounds. Such processes, when used to prepare a novel amide derivative of the Formula I are provided as a further feature of the invention and are illustrated by the following representative process variants in which, unless otherwise stated, Q, $R^2$, $R^3$, p, q and $R^4$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt or in-vivo-cleavable ester thereof, may be prepared by reacting a benzoic acid of the Formula II, or a reactive derivative thereof,

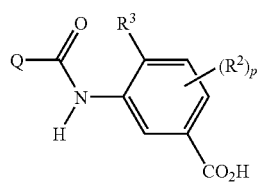

II with an amine of the Formula III

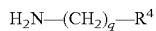

III under standard amide bond forming conditions, wherein variable groups are as defined hereinbefore and wherein any functional group is protected if necessary, and:

(i) removing any protecting groups; and (ii) optionally forming a pharmaceutically-acceptable salt or in-vivo-cleavable ester.

A suitable activated derivative of an acid of the Formula II is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, −78 to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, 1-methoxybenzyl, o-nitrobenzyl, 1-nitrobenzyl, benzhydryl and phthalidyl); tri(lower alkyl)silyl groups (for example trimethylsilyl and tert-butyldimethylsilyl);

tri(lower alkyl)silyl lower alkyl groups (for example trimethylsilylethyl); and (2-6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, R-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, R-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, R-methoxybenzyloxycarbonyl, o-nitrobenzyloxycarbonyl, nitrobenzyloxycarbonyl; trialkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The benzoic acid of Formula II may be prepared by the cleavage of the corresponding ester thereof which, in turn, may be prepared by reaction of an acid of Formula IV, or an activated derivative thereof as defined hereinbefore,

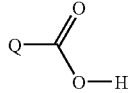

IV with an aniline of Formula V

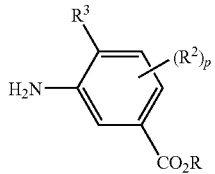

V wherein R is, for example, lower alkyl or benzyl, under suitable amide bond forming conditions as defined hereinbefore.

Typical conditions include activating the carboxy group of the compound of Formula IV, for example by treatment with a halo reagent (for example oxalyl chloride) to form an acyl halide in an organic solvent at ambient temperature and then reacting the activated compound with the aniline of Formula V. Any functional groups are protected and deprotected as necessary.

(b) A compound of the Formula I, or a pharmaceutically-acceptable salt or in-vivo-cleavable ester thereof, may be prepared by reacting an acid of the Formula IV, or an activated derivative thereof as defined hereinbefore,

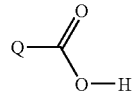

IV with an aniline of the Formula VI

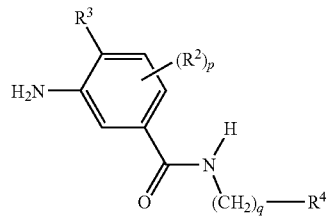

VI under standard amide bond forming conditions as defined hereinbefore, wherein variable groups are as defined hereinbefore and wherein any functional group is protected, if necessary, and:
  (i) removing any protecting groups;
  (ii) optionally forming a pharmaceutically-acceptable salt or in-vivo-cleavable ester.

The aniline of Formula VI may be prepared by reduction of the corresponding nitro compound using convention procedures such as those illustrated in the Examples. Typical reaction conditions include the use of ammonium formate in the presence of a catalyst (for example palladium-on-carbon) in the presence of an organic solvent (preferably a polar protic solvent), preferably with heating, for example to about 60° C. Any functional groups are protected and deprotected as necessary.

(c) A compound of the Formula I wherein a substituent on Q or $R^4$ is (1-6C)alkoxy or substituted (1-6C)alkoxy, (1-6C)alkylthio, (1-6C)alkylamino, di-[(1-6C)alkyl]amino or substituted (1-6C)alkylamino or heterocyclyloxy, may be prepared by the alkylation, conveniently in the presence of a suitable base as defined hereinbefore, of an amide derivative of the Formula I wherein a substituent on Q or $R^4$ is hydroxy, mercapto or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, or for the alkylation of hydroxy to heterocyclyloxy, for example an alkyl or substituted alkyl halide, for example a (1-6C)alkyl chloride, bromide or iodide or a substituted (1-6C)alkyl chloride, bromide or iodide or a heterocyclyl chloride, bromide or iodide, in the presence of a suitable base as defined hereinbefore.

(d) A compound of the Formula I wherein a substituent on Q or $R^4$ is (1-6C)alkanoylamino or substituted (2-6C)alkanoylamino may be prepared by the acylation of a compound of the Formula I wherein a substituent on Q or $R^4$ is amino.

A suitable acylating agent is, for example, any agent known in the art for the acylation of amino to acyl amino, for example an acyl halide, for example a (1-6C)alkanoyl chloride or bromide, conveniently in the presence of a suitable base, as defined hereinbefore, an alkanoic acid anhydride or mixed anhydride, for example a (1-6C)alkanoic acid anhydride such as acetic anhydride or the mixed anhydride formed by the reaction of an alkanoic acid and a (1-6C)alkoxycarbonyl halide, for example a (1-6C)alkoxycarbonyl chloride, in the presence of a suitable base as defined hereinbefore. In general the acylation is carried out in a suitable inert solvent or diluent as defined hereinbefore and at a temperature, in the range, for example, −30 to 120° C., conveniently at or near ambient temperature.

(e) A compound of the Formula I wherein a substituent on Q or $R^4$ is (1-6C)alkanesulphonylamino may be prepared by the reaction of a compound of the Formula I wherein a substituent on Q or $R^4$ is amino with a (1-6C)alkanesulphonic acid, or an activated derivative thereof.

A suitable activated derivative of a (1-6C)alkanesulphonic acid is, for example, an alkanesulphonyl halide, for example an alkanesulphonyl chloride formed by the reaction of the sulphonic acid and an inorganic acid chloride, for example thionyl chloride. The reaction is preferably carried out in the presence of a suitable base as defined hereinbefore, particularly pyridine, and in a suitable inert solvent or diluent as defined hereinbefore, particularly methylene chloride.

(f) A compound of the Formula I wherein a substituent on Q or $R^4$ is carboxy, carboxy-(1-6C)alkyl, carboxy-(1-6C)alkoxy, carboxy-(1-6C)alkylamino, N-(1-6C)alkyl-carboxy-(1-6C)alkylamino or carboxy-(2-6C)alkanoylamino may be prepared by the cleavage of a compound of the Formula I wherein a substituent on Q or $R^4$ is (1-6C)alkoxycarbonyl, (1-6C)alkoxycarbonyl-(1-6C)alkyl, (1-6C)alkoxycarbonyl-(1-6C)alkoxy, (1-6C)alkoxycarbonyl-(1-6C)alkylamino, N-(1-6C)alkyl-(1-6C)alkoxycarbonyl-(1-6C)alkylamino or (1-6C)alkoxycarbonyl-(2-6C)alkanoylamino as appropriate.

The cleavage reaction may conveniently be carried out by any of the many procedures known in the art for such a transformation. The reaction may be carried out, for example, by hydrolysis under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction is preferably carried out in the presence of water and a suitable solvent or diluent such as methanol or ethanol. The reaction is conveniently carried out at a temperature in the range 10 to 150° C., preferably at or near ambient temperature.

(g) A compound of the Formula I wherein a substituent on Q or $R^4$ is amino-(1-6C)alkyl, heterocyclyl-(1-6C)alkyl, (1-6C)alkylamino-(1-6C)alkyl, di-[(1-6C)alkyl]amino-(1-6C)alkyl, substituted (2-6C)alkylamino-(1-6C)alkyl or substituted N-(1-6C)alkyl-(2-6C)alkylamino-(1-6C)alkyl may be prepared by the reaction of a compound of the Formula I wherein a substituent on Q or $R^4$ is a group of the formula -(1-6C)alkylene-Z wherein Z is a displaceable group with an appropriate amine or heterocyclyl compound.

A suitable displaceable group Z is, for example, a halogeno group such as fluoro, chloro or bromo, a (1-6C)alkanesulphonyloxy group such as methanesulphonyloxy or an arylsulphonyloxy group such as 4-toluenesulphonyloxy.

The reaction is conveniently carried out in the presence of a suitable base as defined hereinbefore and in the presence of a suitable inert diluent or carrier as defined hereinbefore. The reaction is conveniently carried out at a temperature in the range 10 to 150° C., preferably at or near 50° C.

(h) A compound of the Formula I wherein a substituent on Q or $R^4$ is amino, heterocyclyl, (1-6C)alkylamino, di-[(1-6C)alkyl]amino, substituted (1-6C)alkylamino, substituted N-(1-6C)alkyl-(1-6C)alkylamino, substituted (2-6C)alkylamino or substituted N-(1-6C)alkyl-(2-6C)alkylamino may be prepared by the reaction of a compound of the Formula I wherein a substituent on Q or $R^4$ is a displaceable group Z as defined hereinbefore with an appropriate amine or heterocyclyl compound.

The reaction is conveniently carried out in the presence of a suitable base as defined hereinbefore and in the presence of a suitable inert diluent or carrier as defined hereinbefore. The reaction is conveniently carried out at a temperature in the range 25 to 250° C., preferably at or near 150° C.

(i) A compound of the Formula I wherein a substituent on Q or $R^4$ is N-(1-6C)alkyl-(1-6C)alkanesulphonylamino may be prepared by the alkylation, conveniently in the presence of a suitable base as defined hereinbefore, of an amide derivative of the Formula I wherein a substituent on Q or $R^4$ is (1-6C)alkanesulphonylamino.

The reaction is conveniently carried out in the presence of a suitable inert diluent or carrier as defined hereinbefore and at a temperature in the range 10 to 150° C., preferably at or near ambient temperature.

(j) A compound of the Formula I wherein a substituent on Q or $R^4$ is a hydroxy-heterocyclyl-(1-6C)alkoxy group (such as 2-hydroxy-3-piperidinopropoxy), a hydroxy-(1-6C)alkylamino-(2-6C)alkoxy group (such as 2-hydroxy-3-methylaminopropoxy) or a hydroxy-di-[(1-6C)alkyl]amino-(2-6C)alkoxy group (such as 3-dimethylamino-2-hydroxypropoxy or 3-[N-(3-dimethylaminopropyl)-N-methylamino]-2-hydroxypropoxy) may be prepared by the reaction of a compound of the Formula I wherein a substituent on Q or $R^4$ is a epoxy-substituted (1-6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(k) A compound of the Formula I wherein $R^2$ or a substituent on Q or $R^4$ is an amino group may be prepared by the reduction of a compound of the Formula I wherein $R^2$ or a substituent on Q or $R^4$ is a nitro group.

Typical reaction conditions include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating, for example to about 60° C. Any functional groups are protected and deprotected as necessary.

The following biological assays and Examples serve to illustrate the present invention.

Biological Assays

The following assays can be used to measure the p38 kinase-inhibitory, the TNF-inhibitory and anti-arthritic effects of the compounds of the present invention:

In Vitro Enzyme Assay

The ability of compounds of the invention to inhibit the enzyme p38 kinase was assessed. Activity of test compounds against each of the p38α and p38β isoforms of the enzyme was determined.

Human recombinant MKK6 (GenBank Accession Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271, 2886-2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta* 1995, 1265, 224-227 and Y. Jiang et al., *Journal of Biological Chemistry*. 1996, 271, 17920-17926.

Both p38 protein isoforms were expressed in e coli in PET vectors. Human recombinant p38α and p38β isoforms were produced as 5'c-myc, 6His tagged proteins. Both MKK6 and the p38 proteins were purified using standard protocols: the GST MKK6 was purified using a glutathione sepharose column, and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforms of p38. The activation incubate comprised p38α (10 of 10 mg/ml) or p38β (10 μl of 5 mg/nl) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (3011 of 50 mM Mg(OCOCH$_3$)$_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM. 'Kinase Assay Mix' [30 μl; comprising Myelin Basic Protein (Gibco BRL cat. no. 1322B-010; 1 ml of a 3.33mg/ml solution in water), activated p38 enzyme (50 μl) and 'Kinase Buffer' (2 ml)] was then added followed by 'Labelled ATP' [10 μl; comprising 50 μM ATP, 0.8 μCi $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow IC$_{50}$ values to be determined.

In Vitro Cell-Based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphopreph™; Nycomed). Mononuclear cells were resuspended in culture medium [RPMI 1640 medium (Gibco) supplemented with 50 units/ml penicillin, 50 μg/ml streptomycin, 2 mM glutamine and 1% heat-inactivated human AB serum (Sigma H-1513)]. Compounds were solubilised in DMSO at a concentration of 50 mM, diluted 1:100 in culture medium and subsequently serial dilutions were made in culture medium containing 1% DMSO. PBMCs (2.4×10$^5$ cells in 160 μl culture medium) were incubated with 20 μl of varying concentrations of test compound (triplicate cultures) or 20 μl culture medium containing 1% DMSO (control wells) for 30 minutes at 37° C. in a humidified (5%CO$_2$/95% air) incubator (Falcon 3072; 96 well flat-bottom tissue culture plates). 20μl lipopolysaccharide [LPS *E. Coli* 0111:B4 (Sigma L-4130), final concentration 10 μg/ml] solubilised in culture medium was added to appropriate wells. 20 μl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., *Int. J. Immunopharmac.* (1993), 15(3), 409-413) or an inhibitor of proTNFα convertase (for example, see McGeehan, G. M. et al. *Nature* (1994) 370, 558-561). Plates were incubated for 7 hours at 37° C. (humidified incubator) after which 100 μl of the supernatant was removed from each well and stored at –70° C. (96 well round-bottom plates; Corning 25850). TNFα levels were determined in each sample using a human TNFα ELISA (see WO92/10190 and *Current Protocols in Molecular Biology*, vol 2 by Frederick M. Ausubel et al., John Wiley and Sons Inc.).

% inhibition=(LPS alone–medium alone)–(test concentration–Medium alone)/(LPS alone–medium alone)×100

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 μl whole blood were added to 96 well round-bottom plates (Corning 25850). Compounds were solubilised and serially diluted in RPMI 1640 medium (Gibco) supplemented with 50 units/ml penicillin, 50 μg/ml streptomycin and 2 mM glutamine, as detailed above. 20 μl of each test concentration was added to appropriate wells (triplicate cultures). 20 μl of RPMI 1640 medium supplemented with antibiotics and glutamine was added to control wells. Plates were incubated for 30 minutes at 37° C. (humidified incubator), prior to addition of 20 μl LPS (final concentration 10 μg/ml). RPMI 1640 medium was added to control wells. Six "LPS alone" and four "medium alone" controls were included on each plate. A known TNFα synthesis/secretion inhibitor was included in each test. Plates were incubated for 6 hours at 37°

C. (humidified incubator). Plates were centrifuged (2000 rpm for 10 minutes) and 100 μl plasma removed and stored at −70° C. (Corning 25850 plates). TNFα levels were measured by ELISA (see WO92/10190 and *Current Protocols in Molecular Biology* vol 2 by Frederick M. Ausubel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex Vivo/In Vivo Assessment

The ability of the compounds of this invention as ex vivo TNFα inhibitors were assessed in the rat or mouse. Briefly, groups of male Wistar Alderley Park (AP) rats (180-210 g) were dosed with compound (6 rats) or drug vehicle (10 rats) by the appropriate route, for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 μl of each sample was added to a set format pattern in a 96 well round bottom plate (Corning 25850). 50 μl of heparinized human blood was then added to each well, mixed and the plate was incubated for 30 min at 37° C. (humidified incubator). LPS (25 μl; final concentration 10 μg/ml) was added to the wells and incubation continued for a further 5.5 hours. Control wells were incubated with 25 μl of medium alone. Plates were then centrifuged for 10 min at 2000 rpm and 200 μl of the supernatants were transferred to a 96 well plate and frozen at −20° C. for subsequent analysis of TNF concentration by ELISA.

Data analysis by dedicated software calculates for each compound/dose:

$$\% \text{ inhibition of TNF}\alpha = \frac{\text{Mean TNF}\alpha(\text{Controls}) - \text{Mean TNF}\alpha(\text{Treated})}{\text{Mean TNF}\alpha(\text{Controls})} \times 100$$

Alternatively, mice could be used instead of rats in the above procedure.

Test as Anti-Arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.*, 146, 857.
2. Williams, R. O. et al., (1992) *Proc. Natl. Acad. Sci.*, 89, 9784.
3. Williams, R. O. et al., (1995) *Immunology*, 84, 433.
4. Badger, M. B. et al., (1996) *The Journal of Pharmacology and Experimental Therapeutics*, 279, 1453-1461.

Although the pharmacological properties of the compounds of the Formula I vary with structural change as expected, in general a compound of the Formula I gives over 30% inhibition of p38α and/or p38β at concentrations up to 10 μM and over 30% inhibition in the PBMC test at concentrations up to 50 μM. No physiologically unacceptable toxicity was observed at the effective dose for compounds tested of the present invention.

By way of example, the compound N-(3-dimethylaminophenyl)-4-methyl-3,4-propylbenzamido)benzamide [Example 3, Compound No. 1] has an $IC_{50}$ of approximately 0.3cm against p38α and an $IC_{50}$ of approximately 6 μM in the PBMC test; the compound N-(2-cyclohexylethyl)-3-(3,4-diethoxybenzamido)-4-methylbenzamide [Example 11] has an $IC_{50}$ of approximately 1 μM against p38α and an $IC_{50}$ of approximately 8 μM in the PBMC test and the compound N-(3-dimethylaminophenyl)-4-methyl-3,6-quinolylcarbonylamino)benzamide [Example 12] has an $IC_{50}$ of approximately 0.7 μM against p38α and an $IC_{50}$ of approximately 22 μM in the PBMC test.

As disclosed hereinbefore, an aspect of the present invention concerns compounds of the Formula I wherein Q is substituted by a basic substituent selected from the substituents for Q defined hereinbefore and $R^4$ is, for example, a phenyl group which also bears a basic substituent selected from the substituents for $R^4$ defined hereinbefore, which compounds possess improved TNFα inhibitory potency in one or both of the PBMC and HWB tests. By way of example, 4-methyl-N-(3-morpholinophenyl)-3-(3-piperidin-4-yloxybenzamido)benzamide [Example 20] has an $IC_{50}$ of approximately 0.05 μM against p38α and an $IC_{50}$ of approximately 2 μM in the HWB test; 4-methyl-3-[3-(4-methylpiperazin-1-ylmethyl)benzamido]-N-(3-morpholinophenyl)benzamide [Example 30] has an $IC_{50}$ of approximately 0.05 μM against p38α and an $IC_{50}$ of approximately 5 μM in the HWB test; and 4-methyl-3-(4-diethylaminomethylbenzamido)-N-(3-morpholinophenyl)benzamide [Example 31(4)] has an $IC_{50}$ of approximately 0.3 μM against p38α and an $IC_{50}$ of approximately 15 μM in the HWB test.

According to a further aspect of the invention there is provided a pharmaceutical composition which comprises an amide derivative of the Formula I, or a pharmaceutically-acceptable or in-vivo-cleavable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided an amide derivative of the Formula I, or a pharmaceutically-acceptable salt or in-vivo-cleavable ester thereof, as defined hereinbefore for use in a method of treatment of the human or animal body by therapy.

According to a further aspect of the invention there is provided the use of an amide derivative of the Formula I, or a pharmaceutically-acceptable salt or in-vivo-cleavable ester thereof, as defined hereinbefore in the manufacture of a medicament for use in the treatment or medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt or in vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula 1, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of rheumatoid arthritis, asthma, irritable bowel disease, multiple sclerosis, AIDS, septic shock, congestive heart failure, ischaemic heart disease or psoriasis.

In a further aspect the present invention provides a method of treating rheumatoid arthritis, asthma, irritable bowel disease, multiple sclerosis, AIDS, septic shock, congestive heart failure, ischaemic heart disease or psoriasis which comprises administering to a warm-blooded animal an effective amount of a compound of the Formula I, or a pharmaceutically-acceptable salt or in-vivo-cleavable ester thereof.

The compounds of this invention may be used in combination with other drugs and therapies used in the treatment of disease states which would benefit from the inhibition of cytokines, in particular TNF and IL-1. For example, the compounds of the Formula I could be used in combination with drugs and therapies used in the treatment of rheumatoid arthritis, asthma, irritable bowel disease, multiple sclerosis, AIDS, septic shock, congestive heart failure, ischaemic heart disease, psoriasis and the other disease states mentioned earlier in this specification.

For example, by virtue of their ability to inhibit cytokines, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt or in-vivo-cleavable ester thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:

| DMF | N,N-dimethylformamide |
| DMSO | dimethylsulphoxide |
| THF | tetrahydrofuran |

EXAMPLE 1

N-(3-dimethylaminophenyl)-3-(3-methoxybenzamido)-4-methylbenzamide

Triethylamine (0.101 g) was added to a stirred mixture of 3-amino-N-(3-dimethylaminophenyl)-4-methylbenzamide (0.135 g), 3-methoxybenzoyl chloride (0.13 g) and methylene chloride (5 ml) and the resultant mixture was stirred at ambient temperature for 16 hours. The mixture was evaporated and the residue was partitioned between ethyl acetate and a saturated aqueous sodium bicarbonate solution. The organic phase was evaporated and the residue was triturated under a mixture of ethyl acetate and isohexane. There was thus obtained the title compound as a solid (0.156 g); Mass Spectrum: M+H$^+$ 404.

The 3-amino-N-(3-dimethylaminophenyl)-4-methylbenzamide used as a starting material was prepared as follows:

Oxalyl chloride (1.73 ml) and DMF (a few drops) were added in turn to a solution of 4-methyl-3-nitrobenzoic acid (3.0 g) in methylene chloride (30 ml) which had been cooled to 0° C. and the resultant mixture was stirred at ambient temperature for 3 hours. The mixture was evaporated and the residue was dissolved in methylene chloride (30 ml). 3-Dimethylaminoaniline hydrochloride (2.89 g), 4-dimethylaminopyridine (0.169 g) and triethylamine (7.7 ml) were added in turn and the reaction mixture was stirred at ambient temperature for 16 hours. The reaction mixture was partitioned between methylene chloride and a saturated aqueous sodium chloride solution. The organic phase was dried over magnesium sulphate and evaporated. The residue was purified by column chromatography using increasingly polar mixtures of methylene chloride and methanol as eluent. There was thus obtained N-(3dimethylaminophenyl)-4-methyl-3-nitrobenzamide as a yellow solid (3.75 g); NMR Spectrum: (CDCl$_3$) 2.69 (s, 3H), 3.0 (s, 6H), 6.57 (d, 1H), 6.87 (d, 1H), 7.2 (m, 2H), 7.49 (d, 1H), 7.75 (broad s, 1H), 8.05 (d, 1H), 8.45 (s, 1H).

10% Palladium-on-carbon (0.369 g) was added to a solution of the material so obtained (3.69 g) in methanol (150 ml). Ammonium formate (7.8 g) was added and the resultant mixture was stirred and heated to reflux for 1.25 hours. The mixture was cooled to ambient temperature and filtered through diatomaceous earth. The filtrate was evaporated and the residue was triturated under water. The resultant solid was dried under vacuum at 55° C. to give 3-amino-N-(3-dimethylaminophenyl)-4-methylbenzamide as a white solid (3.04 g); NMR Spectrum: (CDCl$_3$) 2.22 (s, 3H), 2.98 (s, 6H), 3.75 (broad s, 2H), 6.52 (m, 1H), 6.83 (d, 1H), 7.13 (s, 2H), 7.21 (m, 3H), 7.68 (broad s, 1H).

EXAMPLE 2

N-(3-dimethylaminophenyl)-4-methyl-3-(5-methyl-isoxazol-3-ylcarbonylamino)benzamide Triethylamine (0.129 ml) was added to a stirred mixture of 3-amino-N-(3-dimethylaminophenyl)-4-methylbenzamide (0.1 g), 4-dimethylaminopyridine (5 mg), 5-methylisoxazol-3-ylcarbonyl chloride (0.081 g) and methylene chloride (3 ml) and the resultant mixture was stirred at ambient temperature for 16 hours. The mixture was diluted with methylene chloride (10 ml), washed with a saturated aqueous sodium bicarbonate solution and dried over magnesium sulphate. The organic solution was evaporated and the residue was triturated under isohexane. The resultant solid was dried at 55° C. under vacuum to give the title compound as a solid (0.1 g); NMR Spectrum: (CDCl$_3$) 2.42 (s, 3H), 2.55 (s, 3H), 2.97 (s, 6H), 6.55 (m, 2H), 6.89 (d, 1H), 7.23 (m, 2H), 7.36 (d, 1H), 7.72 (d, 1H), 7.84 (broad s, 1H), 8.55 (broad s, 2H); Mass Spectrum: M+H$^+$ 379.

EXAMPLE 3

Using an analogous procedure to that described in Example 1 or 2, the appropriate benzoyl chloride (prepared by reaction of the corresponding benzoic acid with oxalyl chloride using an analogous procedure to that described in the first part of the portion of Example 1 which is concerned with the preparation of starting materials) was reacted with the appropriate aniline to give the compounds described in Table I.

TABLE I

| No. | (R$^1$)$_m$ | R | Method | Note |
|---|---|---|---|---|
| 1 | 4-propyl | 3-dimethylamino | Ex. 2 | (a) |
| 2 | 4-ethyl | 3-dimethylamino | Ex. 1 | (b) |
| 3 | 3,4-dimethyl | 3-dimethylamino | Ex. 1 | (c) |
| 4 | 4-acetyl | 3-dimethylamino | Ex. 2 | (d) |
| 5 | 4-methoxy | 3-dimethylamino | Ex. 1 | (e) |
| 6 | 4-ethoxy | 3-dimethylamino | Ex. 1 | (f) |
| 7 | 3,4-dimethoxy | 3-dimethylamino | Ex. 2 | (g) |
| 8 | 3,4,5-trimethoxy | 3-dimethylamino | Ex. 2 | (h) |
| 9 | 4-butoxy | 3-dimethylamino | Ex. 1 | (i) |
| 10 | 3-cyano | 3-dimethylamino | Ex. 1 | (j) |
| 11 | 3,4-methylenedioxy | 3-dimethylamino | Ex. 1 | (k) |

Notes
(a) The product gave the following data: NMR Spectrum: (CDCl$_3$) 0.97(t, 3H), 1.69(m, 2H), 2.08(s, 3H), 2.67(t, 2H), 2.96(s, 6H), 6.53(d, 1H), 6.92(d, 1H), 7.1(d, 1H), 7.2(t, 2H), 7.34(d, 2H), 7.66(m, 2H), 7.82(d, 2H), 7.94(broad s, 1H), 8.4(broad s, 1H); Mass Spectrum: M + H$^+$ 416.
(b) The product gave the following data: Mass Spectrum: M + H$^+$ 402.
(c) The product gave the following data: Mass Spectrum: M + H$^+$ 402.
(d) The product gave the following data: NMR Spectrum: (CDCl$_3$) 2.42(s, 3H), 2.67(s, 3H), 2.99(s, 6H), 6.57(d, 1H), 6.91(d, 1H), 7.21(m, 2H), 7.37(d, 1H), 7.71(d, 1H), 7.9(m, 2H), 8.02(d, 2H), 8.11(d, 2H), 8.37(s, 1H); Mass Spectrum: M + H$^+$ 416.
The 4-acetylbenzoyl chloride was prepared as follows:-
Oxalyl chloride (0.058 ml) was added to a solution of 4-acetylbenzoic acid (0.091 g) in a mixture of methylene chloride (3 ml) and DMF (a few drops) and the mixture was stirred at ambient temperature for 6 h. The mixture was evaporated to give the desired compound which was used without further purification.
(e) The product gave the following data: Mass Spectrum: M + H$^+$ 404.
(f) The product gave the following data: Mass Spectrum: M + H$^+$ 418.
(g) The product gave the following data: NMR Spectrum: (DMSOd$_6$) 2.29(s, 3H), 2.86(s, 6H), 3.83(s, 6H), 6.46(d, 1H), 7.12(m, 4H), 7.4(d, 1H), 7.58(broad s, 1H), 7.64(d, 1H), 7.79(d, 1H), 7.92(s, 1H), 9.88(s, 1H), 9.96(s, 1H); Mass Spectrum: M + H$^+$ 434.
(h) The product was purified by column chromatography using increasingly polar mixtures of methylene chloride and methanol as eluent. The resultant product gave the following data: NMR Spectrum: (CDCl$_3$)2.24(s, 3H), 2.93(s, 6H), 3.89(s, 9H), 6.5(d, 1H), 6.92(d, 1H), 7.15(m, 5H), 7.54(d, 1H), 7.84(broad s, 1H), 8.11(broad s, 1H), 8.32(broad s, 1H); Mass Spectrum: M + H$^+$ 465.
(i) The product gave the following data: Mass Spectrum: M + H$^+$ 446.
(j) The product gave the following data: Mass Spectrum: M + H$^+$ 399.
(k) The product gave the following data: Mass Spectrum: M + H$^+$ 418.

EXAMPLE 4

N-(3-dimethylaminophenyl)-3-(4-hydroxybenzamido)-4-methylbenzamide

Using an analogous procedure to that described in the last paragraph of the portion of Example 1 which is concerned with the preparation of starting materials, a mixture of 3-(4-benzyloxybenzamido)-N-(3-dimethylaminophenyl)-4-methylbenzamide (0.227 g), 10% palladium-on-carbon (0.028 g), ammonium formate (0.37 g) and methanol (20 ml) was stirred and heated to reflux for 1.5 hours. The mixture was cooled to ambient temperature and filtered through diatomaceous earth. The filtrate was evaporated and the residue was triturated under water. The resultant solid was washed with a 100:1:0.12 mixture of methylene chloride, methanol and a saturated aqueous ammonium hydroxide solution and dried under vacuum at 55° C. There was thus obtained the title compound as a solid (0.104 g); NMR Spectrum: (DMSOd$_6$) 2.26 (s, 3H), 2.84 (s, 6H), 6.44 (d, 1H), 6.84 (d, 2H), 7.13 (m, 3H), 7.39 (d, 1H), 7.76 (d, 1H), 7.86 (d, 2H), 7.92 (s, 1H), 9.73 (s, 1H), 9.91 (s, 1H); Mass Spectrum: M+H$^+$ 391.

The 3-(4-benzyloxybenzamido)-N-(3-dimethylaminophenyl)-4-methylbenzamide used as a starting material was prepared as follows:

Oxalyl chloride (0.12 ml) was added to a solution of 4-benzyloxybenzoic acid (0.254 g) in a mixture of methylene chloride (5 ml) and DMF (a few drops) which had been cooled to 0° C. The resultant mixture was stirred at ambient temperature for 4 hours. The reaction mixture was evaporated and the residue was dissolved in methylene chloride (6 ml). 3-Amino-N-(3-dimethylaminophenyl)-4-methylbenzamide (0.3 g), 4-dimethylaminopyridine (0.014 g) and diisopropylethylamine (0.485 ml) were added in turn and the resultant solution was stirred at ambient temperature for 16 hours. The reaction mixture was partitioned between methylene chloride and a saturated aqueous sodium chloride solution, dried over magnesium sulphate and evaporated. The residue was purified by column chromatography using a 1:1 mixture of isohexane and ethyl acetate as eluent. There was thus obtained the required starting material as a solid (0.358 g); NMR Spectrum: (CDCl$_3$) 2.39 (s, 3H), 2.98 (s, 6H), 5.15 (s, 2H), 6.53 (d, 1H), 6.93 (d, 1H), 7.07 (d, 2H), 7.21 (m, 2H), 7.40 (m, 6H), 7.72 (m, 2H), 7.9 (m, 3H), 8.40 (s, 1H).

EXAMPLE 5

N-(3-dimethylaminophenyl)-3-[4-(2-methoxyethoxy)benzamido]-4-methylbenzamide

2-Bromoethyl methyl ether (0.033 ml) was added to a stirred suspension of N-(3-dimethylaminophenyl)-3-(4-hydroxybenzamido)-4-methylbenzamide (0.9 g) and anhydrous potassium carbonate (0.064 g) in DMF (10 ml) and the resultant mixture was stirred at 80° C. for 5 hours. The mixture was cooled to ambient temperature and partitioned between ethyl acetate and water. The organic phase was washed with a saturated aqueous sodium bicarbonate solution and with a saturated aqueous sodium chloride solution, dried over magnesium sulphate and evaporated. The residue was triturated under diethyl ether. There was thus obtained the title compound as a solid (0.073 g); NMR Spectrum: (DMSOd$_6$) 2.28 (s, 3H), 2.87 (s, 6H), 3.31 (s, 3H), 3.67 (m, 2H), 4.18 (m, 2H), 6.43 (d, 1H) 7.12 (m, 5H), 7.37 (d, 1H), 7.78 (d, 1H), 7.97 (m, 3H), 9.87 (s, 1H), 9.96 (s, 1H); Mass Spectrum: M+H$^+$ 448.

EXAMPLE 6

4-chloro-N-(3-dimethylaminophenyl)-3-(4-propylbenzamido)benzamide

Using an analogous procedure to that described in Example 1, 4-chloro-3-(4-propylbenzamido)benzoyl chloride was reacted with 3-dimethylamino aniline dihydrochloride to give the title compound; NMR Spectrum: DMSOd$_6$) 0.9 (t, 3H), 1.18 (t, 2H), 1.69 (m, 2H), 2.99 (s, 6H), 7.0 (d, 1H), 7.2-7.5 (m, 4H) 7.64-7.8 (m, 3H), 7.84 (d, 1H), 8.0 (m, 2H), 8.19 (s, 1H); Mass Spectrum: M+H$^+$ 436 and 438.

The 4-chloro-3-(4-propylbenzamido)benzoyl chloride used as starting material was prepared as follows:

Acetyl chloride (1.67 ml) was added to a suspension of 3-amino-4-chlorobenzoic acid (2.0 g) in methanol (100 ml) and the mixture was stirred and heated to reflux for 16 hours. The mixture was allowed to cool and was evaporated. The residue was partitioned between methylene chloride and a saturated aqueous sodium bicarbonate solution. The organic phase was washed with a saturated aqueous sodium chloride solution and evaporated. There was thus obtained methyl 3-amino-4-chlorobenzoate as a solid (2.13 g) NMR Spectrum: (DMSOd$_6$) 3.79 (s, 3H), 5.62 (s, 2H), 7.06 (d, 1H), 7.29 (d, 1H), 7.4 (s, 2H).

Triethylamine (1.5 ml) was added to a stirred suspension of methyl 3-amino-4-chlorobenzoate (1.0 g) and 4-propylbenzoyl chloride (1.34 ml) in methylene chloride (50 ml) and the mixture was stirred at ambient temperature for 16 hours. The mixture was washed with a saturated aqueous sodium bicarbonate solution and evaporated. The residue was triturated under a mixture of ethyl acetate, diethyl ether and isohexane. There was thus obtained methyl 4-chloro-3-(4-propylbenzamido)-benzoate as a solid (1.05 g); NMR Spectrum: (DMSOd$_6$) 0.89 (t, 3H), 1.58-1.66 (m, 2H), 2.63 (t, 2H), 3.86 (s, 3H), 7.34 (d, 2H), 7.7 (d, 1H), 7.81 (d, 1H), 7.9 (d, 2H), 8.2 (s, 1H), 10.07 (s, 1H).

A 2N aqueous sodium hydroxide solution (3.02 ml) was added to a mixture of a portion (0.5 g) of the material so obtained, methanol (20 ml) and water (5 ml) and the resultant mixture was stirred at ambient temperature for 16 hours. The mixture was evaporated and the residue was dissolved in water and extracted with ethyl acetate. The aqueous phase was acidified to pH2 and the resulting precipitate was isolated and washed with ethyl acetate and diethyl ether. There was thus obtained 4-chloro-3-(4-propylbenzamido)benzoic acid as a solid (0.175 g); NMR Spectrum: (DMSOd$_6$) 0.89 (t, 3H), 1.58-1.66(m, 2H), 2.62 (t, 2H), 7.36 (d, 2H), 7.67 (d, 1H), 7.81 (d, 1H), 7.9 (d, 2H), 8.15 (s, 1H), 10.07 (s, 1H), 13.2 (broad s, 1H).

Oxalyl chloride (0.048 ml) was added dropwise to a stirred solution of a portion (0.16 g) of the material so obtained in a mixture of methylene chloride (20 ml) and DMF (a few drops) which had been cooled to 0° C. The mixture was allowed to warm to ambient temperature and was stirred for 4 hours. The mixture was evaporated to give 4-chloro-3-(4-propylbenzamido)benzoyl chloride which was used without further purification.

EXAMPLE 7

3-(4-carboxybenzamido)-N-(3-dimethylaminophenyl)-4-methylbenzamide

A mixture of 3-(4-methoxycarbonylbenzamido)-N-(3-dimethylaminophenyl)-4-methylbenzamide (0.15 g), 2N aqueous sodium hydroxide solution (5 ml), methanol (2 ml) and THF (4 ml) was stirred at ambient temperature for 16 hours. The mixture was evaporated and the residue was acidified with 2N aqueous hydrochloric acid. The resultant precipitate was isolated and dried under vacuum at 55° C. to yield the title compound as a white solid (0.095 g); NMR Spectrum: (DMSOd$_6$) 2.32 (s, 3H), 3.06 (s, 6H), 7.28 (broad s, 1H), 7.43 (m, 2H), 7.7 (d, 1H), 7.84 (d, 1H), 8.0 (d, 2H), 8.1 (m, 4H), 10.26 (s, 1H), 10.46 (s, 1H); Mass Spectrum: M+H$^+$ 418.

The 3-(4-methoxycarbonylbenzamido)-N-(3-dimethylaminophenyl)-4-methylbenzamide used as a starting material was obtained as follows:

Triethylamine (0.26 ml) was added to a stirred mixture of 4-methoxycarbonylbenzoyl chloride (0.221 g), 4-dimethylaminopyridine (0.01 g), 3-amino-N-(3-dimethylaminophenyl)-4-methylbenzamide (0.2 g) and methylene chloride (10 ml) and the resultant mixture was stirred at ambient temperature for 16 hours. The mixture was diluted with methylene chloride and washed with a saturated aqueous sodium bicarbonate solution and with a saturated aqueous sodium chloride solution. The organic solution was dried over magnesium sulphate and evaporated. The residue was triturated under isohexane. The resultant solid was isolated and dried under vacuum at 55° C. to give the required starting material as a solid (0.286 g); NMR Spectrum: (CDCl$_3$) 2.4 (s, 3H), 2.98 (s, 6H), 3.98 (s, 3H), 6.54 (m, 1H), 6.92 (d, 1H), 7.2 (m, 3H), 7.35 (d, 1H), 7.71 (d, 1H), 7.92 (s, 1H), 7.98 (d, 2H), 8.18 (d, 2H), 8.35 (s, 1H).

EXAMPLE 8

N-[2-(4-chlorophenoxy)ethyl]-3-(3,4-dimethoxybenzamido)-4-methylbenzamide

A solution of 1-(3-dimethylaminopropyl)-3-ethylcarbodiimide hydrochloride (0.095 g) in methylene chloride (5 ml) was added to a stirred mixture of 3-(3,4-dimethoxybenzamido)-4-methylbenzoic acid (0.157 g), 2-(4-chlorophenoxy) ethylamine (*C. Chim. Ther.,* 1973, 8, 259; 0.086 g), 4-dimethylaminopyridine (0.007 g), 1-hydroxybenzotriazole (0.074 g) and methylene chloride (5 ml). The resultant mixture was stirred at ambient temperature for 16 hours. The mixture was evaporated and the residue was partitioned between ethyl acetate and a saturated aqueous sodium bicarbonate solution. The organic phase was washed with an aqueous citric acid solution, dried over magnesium sulphate and evaporated. There was thus obtained the title compound as a solid (0.158 g); Mass Spectrum: M+H$^+$ 469.

The 3-(3,4-dimethoxybenzamido)-4-methylbenzoic acid used as a starting material was obtained as follows:

Oxalyl chloride (10.5 ml) was added to a solution of 3,4-dimethoxybenzoic acid (18.2 g) in a mixture of methylene chloride (250 ml) and DMF (0.5 ml) which had been cooled to 0° C. The reaction mixture was allowed to warm to ambient temperature and was stirred for 4.5 hours. The mixture was evaporated and the residue was dissolved in methylene chloride (250 ml) and cooled to 0° C. Methyl 3-amino-4-methylbenzoate (11.0 g), 4-dimethylaminopyridine (0.81 g) and triethylamine (23.2 ml) were added and the reaction mixture was stirred at ambient temperature for 65 hours. The reaction mixture was washed in turn with 2N aqueous hydrochloric acid and with a saturated aqueous solution of sodium bicarbonate, dried over magnesium sulfate, and evaporated. There was thus obtained methyl 3-(3,4-dimethoxybenzamido)-4-methylbenzoate as a solid (28.6 g); NMR Spectrum: (CDCl$_3$) 2.4 (s, 3H), 3.85 (m, 6H), 3.96 (s, 3H), 6.76 (d, 1H), 7.2-8.5 (m, 6H).

A solution of the material so obtained in a mixture of 2N aqueous sodium hydroxide solution (300 ml) and methanol (200 ml) was stirred at ambient temperature for 16 hours. The mixture was evaporated and the reaction mixture was partitioned between isohexane and water. The aqueous layer was acidified with aqueous hydrochloric acid and the resultant precipitate was isolated and dried under vacuum at 55° C. to give 3-(3,4-dimethoxybenzamido)-4-methylbenzoic acid as a solid (25.05 g); NMR Spectrum: (DMSOd$_6$) 2.28 (s, 3H), 3.8 (m, 6H), 7.0-7.8 (m, 6H), 7.89 (s, 1H), 9.95 (s, 1H).

EXAMPLE 9

N-cyclobutyl-3-(3,4-dimethoxybenzamido)-4-methylbenzamide

Using an analogous procedure to that described in Example 8, 3-(3,4-dimethoxybenzamido)-4-methylbenzoic acid was reacted with cyclobutylamine to give the title compound; Mass Spectrum: M+H$^+$ 369.

EXAMPLE 10

N-(3,4-dichlorobenzyl)-3-(3,4,5-trimethoxybenzamido)-4-methylbenzamide

Using an analogous procedure to that described in Example 2, 3,4,5-trimethoxybenzoyl chloride was reacted with 3-amino-N-(3,4-dichlorobenzyl)-4-methylbenzamide to give the title compound which was purified by column chromatography using increasingly polar mixtures of methylene chloride and methanol as eluent; NMR Spectrum: (CDCl$_3$) 2.28 (s, 3H), 3.87 (m, 9H), 4.48 (d, 2H), 7.13 (m, 5H), 7.36 (m, 2H), 7.52 (d, 1H), 8.01 (s, 1H), 8.13 (s, 1H); Mass Spectrum: M−H$^-$503.

The 3-amino-N-(3,4-dichlorobenzyl)-4-methylbenzamide used as a starting material was obtained as follows:

Oxalyl chloride (4.8 ml) was added to a solution of 3-nitro-4-methylbenzoic acid (9.06 g) in methylene chloride (100 ml) and DMF (a few drops) and the reaction stirred at ambient temperature for 16 hours. The reaction mixture was evaporated and the residue was dissolved in methylene chloride (100 ml). 3,4-Dichlorobenzylamine (7.04 g), 4-dimethylaminopyridine (0.31 g) and triethylamine (13.9 ml) were added and the reaction mixture was stirred at ambient temperature for 16 hours. The mixture was washed with a saturated aqueous sodium bicarbonate solution, dried over magnesium sulphate and evaporated The residue was purified by column chromatography using a 250:8:1 mixture of methylene chloride, methanol and a saturated aqueous ammonium chloride solution as eluent to give N-(3,4-dichlorobenzyl)-4-methyl-3-nitrobenzamide as a solid (9.95 g); NMR Spectrum: (DMSOd$_6$) 2.57 (s, 3H), 4.47 (d, 2H), 7.31 (m, 1H), 7.56 (m, 2H), 7.61 (d, 1H), 8.1 (m, 1H), 8.47 (d, 1H), 9.3 (t, 1H).

A solution of stannous chloride dihydrate (17.5 g) in concentrated hydrochloric acid (40 ml) was added to a solution of N-(3,4-dichlorobenzyl)-4-methyl-3-nitrobenzamide (5.85 g) in ethanol (40 ml) and concentrated hydrochloric acid (40 ml). The reaction mixture was stirred and heated to reflux for 4 hours. The mixture was cooled and diluted with 2N aqueous hydrochloric acid. The reaction mixture was extracted several times with ethyl acetate, and the combined organic extracts were washed with a saturated solution of sodium bicarbonate, dried over magnesium sulphate and evaporated to give the required starting material as a solid (3.9 g); NMR Spectrum: (CDCl$_3$) 2.2 (s, 3H), 3.74 (broad s, 2H), 4.58 (d, 2H), 6.4 (broad s, 1H), 7.02 (d, 1H), 7.1 (d, 1H), 7.19 (m, 2H), 7.42 (m, 2H).

EXAMPLE 11

N-(2-cyclohexylethyl)-3-(3,4-dimethoxybenzamido)-4-methylbenzamide

Ammonium formate (0.224 g) was added to a stirred mixture of 10% palladium-on-carbon (0.015 g), N-(2-cyclohexen-1-ylethyl)-3-(3,4-dimethoxybenzamido)-4-methylbenzamide (0.15 g) and methanol (15 ml) and the reaction mixture was heated to reflux for 1.25 hours. The reaction mixture was allowed to cool and was filtered through diatomaceous earth. The filtrate was evaporated and the residue was triturated under water. The solid so obtained was dried under vacuum at 55° C. to give the title compound as a powder (0.136 g); NMR Spectrum: (CDCl$_3$) 0.8-2.3 (m, 13H), 2.37 (s, 3H), 3.45 (m, 2H), 3.96 (m, 6H), 6.12 (m, 1H), 6.93 (d, 1H), 7.26 (m, 1H), 7.46 (d, 1H), 7.56 (m, 2H), 7.92 (s, 1H), 8.16 (s, 1H); Mass Spectrum: M+H$^+$ 425.

The N-(2-cyclohexen-1-ylethyl)-3-(3,4-dimethoxybenzamido)-4-methylbenzamide used as a starting material was obtained as follows:

2-Cyclohexen-1-ylethylamine (0.146 ml) was added to a stirred mixture of 3-(3,4-dimethoxybenzamido)-4-methylbenzoic acid (0.3 g), 1-(3-dimethylaminopropyl)-3-ethylcarbodiimide hydrochloride (0.274 g), 4-dimethylaminopyridine (0.012 g) and methylene chloride (5 ml) and the reaction mixture was stirred at ambient temperature for 16 hours. The mixture was partitioned between methylene chloride and 2N aqueous hydrochloric acid. The organic phase was washed with a. saturated aqueous sodium bicarbonate solution, dried over magnesium sulphate and evaporated. There was thus obtained the required starting material as a solid (0.28 g); NMR Spectrum: (CDCl$_3$) 1.6 (m, 4H), 2.0 (m, 4H), 2.23 (m, 2H), 2.37 (s, 3H), 3.51 (m, 2H), 3.96 (m, 6H), 5.54 (bs, 1H), 6.21 (broad s, 1H), 6.94 (d, 1H), 7.21 (m, 1H), 7.43 (m, 1H), 7.55 (m, 2H), 7.81 (broad s, 1H), 8.2 (broad s, 1H).

EXAMPLE 12

N-(3-dimethylaminophenyl)-4-methyl-3-(6-quinolyl-carbonylamino)benzamide

Using an analogous procedure to that described in Example 2, 6-quinolylcarbonyl chloride was reacted with 3-amino-N-(3-dimethylaminophenyl)-4-methylbenzamide to give the title compound; NMR Spectrum: (DMSOd$_6$) 2.35 (s, 3H), 2.91 (s, 6H), 6.58 (m, 1H), 7.2 (m, 2H), 7.43 (d, 1H), 7.65 (m, 11H), 7.82 (d, 1H), 8.01 (s, 11H), 8.17 (m, 2H), 8.32 (d, 1H), 8.59 (d, 1H), 8.7 (d, 1H), 9.02 (s, 1H), 10.05 (s, 1H), 10.32 (s, 1H); Mass Spectrum: M+H$^+$425.

The 6-quinolylcarbonyl chloride used as a starting material was prepared as follows:

Oxalyl chloride (0.058 ml) was added to a solution of 6quinolinecarboxylic acid (0.096 g) in a mixture of methylene chloride (4 ml) and DMF (a few drops) and the reaction mixture was stirred at ambient temperature for 6 hours. The mixture was evaporated to give the required starting material which was used without further purification.

EXAMPLE 13

4-chloro-N-(3-dimethylaminophenyl)-3-(6-quinolyl-carbonylamino)benzamide

Using an analogous procedure to that described in Example 1, 4-chloro-3-(6-quinolylcarbonylamino)benzoyl chloride was reacted with 3-dimethylaminoaniline dihydrochloride to give the title compound; NMR Spectrum: (DMSOd$_6$) 3.04 (s, 6H), 6.5 (d, 1H), 7.08-7.20(m, 3H), 7.61-7.64 (m, 1H), 7.74 (d, 1H), 7.92 (d, 1H) 8.1-8.2 (m, 2H), 7.31 (d, 1H), 8.58 (d, 1H), 8.72 (s, 1H), 9.02 (s, 1H) 10.13 (s, 1H), 10.5 (s, 1H); Mass Spectrum: Mass Spectrum: M+H$^+$ 445 and 447.

The 4-chloro-3-(6-quinolylcarbonylamino)benzoyl chloride used as starting material was prepared as follows:

Triethylamine (4.18 ml) was added to a stirred suspension of methyl (3-amino-4-chloro)benzoate (1.85 g) and 6-quinolylcarbonyl chloride (2.88 g) in methylene chloride (80 ml) and the resultant mixture was stirred at ambient temperature for 16 hours. The mixture was washed with a saturated aqueous sodium bicarbonate solution, dried over magnesium sulphate and evaporated. The residue was triturated under a mixture of ethyl acetate and diethyl ether. There was thus obtained methyl 4-chloro-3-(6-quinolylcarbonylamino)benzoate as a solid (1.1 g); NMR Spectrum: (DMSOd$_6$) 3.87 (s, 3H), 7.62-7.65 (m, 1H), 7.4 (d, 1H), 7.85 (d, 1H), 8.14 (d, 1H), 8.23-8.32 (m, 2H), 8.54 (d, 1H) 8.68 (s, 1H) 9.01 (s, 1H), 10.5 (s, 1H).

A 2N aqueous sodium hydroxide solution (2.21 ml) was added to a portion (0.5 g) of the material so obtained in a mixture of methanol (20 ml) and water (5 ml) and the resultant mixture was stirred at ambient temperature for 16 hours. The mixture was evaporated and the residue was dissolved in water and extracted with ethyl acetate The aqueous phase was acidified to pH2 by the addition of dilute hydrochloric acid solution. The resultant precipitate was isolated and washed with diethyl ether. There was thus obtained 4-chloro-3-(6-quinolylcarbonylamino)benzoic acid hydrochloride salt as a solid (0.329 g); NMR Spectrum: (DMSOd$_6$) 7.64-7.68 (m, 1H), 7.7 (d, 1H), 7.83 (d, 1H),8.14-8.19 (m, 2H), 8.29 (d, 1H), 8.57 (d, 1H) 8.7 (s, 1H) 9.03 (s, 1H).

Oxalyl chloride (0.048 ml) was added dropwise to a stirred solution of a portion (0.181 g) of the acid so obtained in a mixture of methylene chloride (20 ml) and DMF (a few drops) which had been cooled to 0° C. The mixture was allowed to warm to ambient temperature and was stirred for 4 hours. The solvent was evaporated to give 4-chloro-3-(6-quinolylcarbonylamino)benzoyl chloride which was used without further purification.

EXAMPLE 14

3-(6-chloropyrid-3-ylcarbonylamino)-N-(3-dimethylaminophenyl)-4-methylbenzamide

Using an analogous procedure to that described in Example 1, 6-chloropyrid-3-ylcarbonyl chloride was reacted with 3-amino-N-(3-dimethylaminophenyl)-4-methylbenzamide to give the title compound; Mass Spectrum: M+H$^+$ 409 and 411.

EXAMPLE 15

N-(3-dimethylaminophenyl)-4-methyl-3-(2-naphthoylamino)benzamide

Using an analogous procedure to that described in Example 1, 2-naphthoyl chloride was reacted with 3-amino-N-(3-dimethylaminophenyl)-4-methylbenzamide to give the title compound; Mass Spectrum: M+H$^+$ 424.

EXAMPLE 16

3-(3-benzyloxybenzamido)-4-methyl-N-(3-morpholinophenyl)benzamide

Oxalyl chloride (1.24 ml) was added to a mixture of 3-benzyloxybenzoic acid (2.736 g), DMF (1 ml) and methylene chloride which had been cooled to 0° C. and the resultant mixture was stirred at ambient temperature for 4 hours. The mixture was evaporated and a solution of the residue in methylene chloride (60 ml) was added slowly to a stirred mixture of 3-amino-4-methyl-N-(3-morpholinophenyl)benzamide (3.11 g), pyridine (1.69 ml) and methylene chloride (60 ml). The resultant mixture was stirred at ambient temperature for 12 hours. The mixture was washed in turn with water and with a saturated aqueous sodium bicarbonate solution, dried over magnesium sulphate and evaporated. The residue was stirred under diethyl ether (200 ml) for 12 hours and the resultant solid was isolated. There was thus obtained the title compound (4.5 g); NMR Spectrum: (DMSOd$_6$) 2.26 (s, 3H), 3.07 (t, 4H), 3.72 (t, 4H), 5.19 (s, 2H), 6.66 (d, 1H), 7.3 (m, 11H), 7.6 (t, 2H), 7.78 (d, 1H), 7.95 (s, 1H), 10.0 (d, 2H); Mass Spectrum: M+H$^+$ 522.

The 3-amino-4-methyl-N-(3-morpholinophenyl)benzamide used as a starting material was prepared as follows:

A mixture of 3-fluoronitrobenzene (13.2 g), morpholine (45 ml) and DMSO (156 ml) was stirred and heated at 100° C. for 4 days. The mixture was cooled and poured into water. The resultant solid was isolated and dried under vacuum. There was thus obtained 3-morpholinonitrobenzene (14.69 g); NMR Spectrum: (CDCl$_3$) 3.25 (t, 4H), 3.9 (t, 4H), 7.15-7.2 (m, 1H), 7.4 (t, 1H), 7.65-7.75 (m, 2H).

Ammonium formate (22.2 g) was added to a mixture of the material so obtained, 10% palladium-on-carbon (2.1 g) and methanol (250 ml) and the resultant mixture was stirred at ambient temperature for 1 hour. The mixture was evaporated and the residue was partitioned between ethyl acetate and water. The organic phase was dried over magnesium sulphate and evaporated. The solid so obtained was washed with isohexane. There was thus obtained 3-morpholinoaniline (9.9 g); NMR Spectrum: (CDCl$_3$) 3.04 (t, 4H), 3.68 (t, 4H), 3.5 (br m, 2H), 6.17 (m, 2H), 6.24 (m, 1H), 6.98 (t, 1H).

Triethylamine (20 ml) was added to a mixture of 3-morpholinoaniline (9.9 g), 4-methyl-3-nitrobenzoyl chloride (8.92 ml) and methylene chloride (400 ml) and the resultant mixture was stirred at ambient temperature for 68 hours. The mixture was evaporated. Methylene chloride and a saturated aqueous sodium bicarbonate solution were added and the resultant precipitate was isolated, washed with diethyl ether and dried under vacuum. There was thus obtained 4-methyl-3-nitro-N-(3-morpholinophenyl)benzamide (18.24 g); NMR Spectrum: (DMSOd$_6$) 2.6 (s, 3H), 3.0-3.1 (m, 4H), 3.7-3.8 (m, 4H), 6.7-6.75 (m, 1H), 7.2 (t, 1H), 7.25-7.3 (m, 1H), 7.4 (s, 1H), 7.65 (d, 1H), 8.15-8.25 (m, 1H), 8.55 (s, 1H), 10.3-10.33 (s, 1H); Mass Spectrum: M+H$^+$ 342.

Ammonium formate (16.8 g) was added to a mixture of the material so obtained, 10% palladium-on-carbon (1.6 g) and methanol (200 ml) which had been cooled in an ice-bath. The resultant mixture was stirred at ambient temperature for 1.5 hours. The mixture was filtered and the filtrate was evaporated. The residue was dissolved in methylene chloride and dried over magnesium sulphate. The solution was evaporated to give the required starting material (7.34 g); NMR Spectrum: (DMSOd$_6$) 3.0-3.1 (m, 7H), 3.7-3.8 (m, 4H), 5.0 (s, 2H), 6.6-6.7 (m, 1H), 7.05 (s, 2H), 7.1-7.2 (m, 2H), 7.25-7.3 (m, 1H), 7.35-7.4 (m, 1H), 9.8 (s, 1H); Mass Spectrum: M+H$^+$ 312.

EXAMPLE 17

3-(3-hydroxybenzamido)-4-methyl-N-(3-morpholinophenyl)benzamide

A mixture of 3-(3-benzyloxybenzamido)-4-methyl-N-(3-morpholinophenyl)benzamide (4.49 g), 10% palladium-on-carbon (0.5 g) and ethyl acetate was stirred under an atmosphere of hydrogen gas for 12 hours. The resultant mixture was filtered through diatomaceous earth and the separated solids were washed with warm DMF (200 ml). The combined filtrates were concentrated to a volume of about 20 ml and water (50 ml) was added. The resultant solid was dried under vacuum at 55° C. There was thus obtained the title compound as a solid (2.99 g); NMR Spectrum: (DMSOd$_6$) 2.25 (s, 3H), 3.07 (t, 4H), 3.72 (t, 4H), 6.67 (m, 1H), 6.97 (m, 1H), 7.18 (t, 1H), 7.36 (m, 6H), 7.78 (m, 1H), 7.92 (s, 1H), 9.68 (s, 1H), 9.89 (s, H), 10.01 (s, 1H); Mass Spectrum: M+H$^+$ 432.

EXAMPLE 18

3-[3-(1-tert-butoxycarbonylpyrrolidin-3-yloxy)benzamido]-4-methyl-N-(3-morpholinophenyl)benzamide 1-(3-Dimethylaminopropyl)-3-ethylcarbodiimide hydrochloride (0.23 g) was added to a stirred mixture of 3-(1-tert-butoxycarbonylpyrrolidin-3-yloxy)benzoic acid (0.307 g), 3-amino-4-methyl-N-(3-morpholinophenyl)benzamide (0.312 g), 1-hydroxybenztriazole (0.202 g) and DMF (5 ml) which had been cooled to 0° C. The resultant reaction mixture was stirred at ambient temperature for 40 hours. The mixture was partitioned between ethyl acetate and water. The organic phase was washed with water and with a saturated aqueous sodium bicarbonate solution, dried over magnesium sulphate and evaporated. The residue was purified by column chromatography on silica gel using a 3:1 mixture of isohexane and ethyl acetate as eluent. There was thus obtained the title compound as a solid (0.31 g); NMR Spectrum: (DMSOd$_6$) 1.38 (s, 9H), 2.12 (m, 2H), 2.27 (s, 3H), 3 08 (t, 4H), 3.37 (m, 3H), 3.57 (m, 1H), 3.74 (t, 4H), 5.05 (m, 1H), 6.67 (d, 1H), 7.17 (m, 2H), 7.3 (d, 1H), 7.42 (m, 3H), 7.52 (s, 1H), 7.57 (d, 1H), 7.78 (d, 1H), 7.93 (s, 1H), 10.0 (s, 1H), 10.01 (s, 1H); Mass Spectrum: M+H$^+$ 601.

The 3-(1-tert-butoxycarbonylpyrrolidin-3-yloxy)benzoic acid used as a starting material was obtained as follows:

Using an analogous procedure to that described in the first paragraph of the portion of Example 25 which is concerned with the preparation of starting materials, N-tert-butoxycarbonyl-3-hydroxypyrrolidine (J. Amer. Chem. Soc., 1982, 104, 5852-5853) was reacted with ethyl 3-hydroxybenzoate. The product so obtained was hydrolysed with sodium hydroxide using an analogous procedure to that described in the second paragraph of the portion of Example 25 which is concerned with the preparation of starting materials. There was thus obtained the required starting material; NMR Spectrum: (DMSOd$_6$) 1.38 (s, 9H), 2.06 (m, 2H), 3.1 (m, 3H), 3.55 (m, 1H), 5.03 (broad s, 1H), 7.18 (m, 1H), 7.38 (m, 2H), 7.52 (d, 1H); Mass Spectrum: M+H$^+$ 308.

EXAMPLE 19

4-methyl-N-(3-morpholinophenyl)-3-(3-pyrrolidin-3-yloxybenzamido)benzamide

Trifluoroacetic acid (0.6 ml) was added to a stirred solution of 3-[3-(1-tert-butoxycarbonylpyrrolidin-3-yloxy)benzamido]-4-methyl-N-(3-morpholinophenyl)benzamide (0.3 g) in methylene chloride (6 ml) which had been cooled to 0° C. The reaction mixture was stirred at ambient temperature for 3 hours. The mixture was evaporated and the residue was triturated under diethyl ether to give the title compound, as its trifluoroacetate salt. The solid so obtained was dissolved in water (15 ml) and basified by the addition of potassium carbonate. The resultant precipitate was collected, washed with water and dried under vacuum to give the title compound (0.18 g); NMR Spectrum: (DMSOd$_6$) 1.76 (m, 1H), 2.02 (m, 1H), 2.23 (s, 3H), 2.83 (m, 2H), 3.06 (m, 5H), 3.55 (m, 1H), 3.76 (t, 4H), 4.98 (m, 1H), 6.62 (d, 1H), 7.12 (m, 2H), 7.31 (d, 1H), 7.4 (m, 3H), 7.52 (m, 2H), 7.78 (d,. 1H), 7.99 (s, 1H), 10.07 (s, 1H), 10.08 (s, 1H); Mass Spectrum: M+H$^+$ 501.

EXAMPLE 20

4-methyl-N-(3-morpholinophenyl)-3-(3-piperidin-4-yloxybenzamido)benzamide

Using an analogous procedure to that described in Example 18, 3-(1-tert-butoxycarbonylpiperidin-4-yloxy)benzoic acid was reacted with 3-amino-4-methyl-N-(3-morpholinophenyl)benzamide to give 3-[3-(1-tert-butoxycarbonylpiperidin-4-yloxy)benzamido]-4-methyl-N-(3-morpholinophenyl)benzamide in 42% yield; NMR Spectrum: (DMSOd$_6$) 1.38 (s, 9H), 1.54 (m, 2H), 1.91 (m, 2H), 2.27 (s, 3H), 3.06 (t, 4H), 3.2 (m, 2H), 3.64 (m, 2H), 3.72 (t, 4H), 5.01 (m, 1H), 6.66 (m, 1H), 7.18 (m, 2H), 7.28 (d, 1H), 7.4 (m, 3H), 7.56 (m, 2H), 7.77 (m, 1H), 7.92 (s, 1H), 9.98 (s, 1H), 10.01 (s, 1H).

The product so obtained was treated with trifluoroacetic acid using an analogous procedure to that described in Example 19. There was thus obtained the title compound in 81% yield; NMR Spectrum: (DMSOd$_6$) 1.45 (m, 2H), 1.91 (m, 2H), 2.27 (s, 3H), 2.58 (m, 2H), 2.93 (m, 2H), 3.05 (t, 4H), 3.71 (t, 4H), 4.46 (m, 1H), 6.67 (m, 1H), 7.16 (m, 2H), 7.25 (d, 1H), 7.4 (m, 3H), 7.52 (m, 2H), 7.78 (m, 1H), 7.92 (s, 1H), 9.98 (s, 1H), 10.02 (s, 1H); Mass Spectrum: M+H+ 515.

The 3-(1-tert-butoxycarbonylpiperidin-4-yloxy)benzoic acid used as a starting material was obtained as follows:

N-tert-Butoxycarbonyl-4-hydroxypiperidine was obtained from a commercial source, for example from Neosystem, F67100, Strasbourg, France, or was prepared by the following procedure. A solution of di-tert-butyl dicarbonate (53.9 g) in methylene chloride (100 ml) was added dropwise to a stirred mixture of 4-hydroxypiperidine (25 g), triethylamine (50 ml) and methylene chloride (250 ml) which had been cooled to 0° C. The resultant mixture was allowed to warm to ambient temperature and was stirred for 18 hours. The mixture was evaporated and the residue was purified by chromatography on silica a 2:1 mixture of isohexane and ethyl acetate as eluent. The oil so obtained was dried under vacuum at 60° C. to give N-tert-butoxycarbonyl-4-hydroxypiperidine as a white solid (49.1 g); NMR Spectrum: (DMSOd$_6$) 1.39 (s, 9H), 1.55 (m, 2H), 1.78 (m, 2H), 2.95 (m, 2H), 3.76 (m, 2H).

Diethyl azodicarboxylate (1.95 ml) was added dropwise over 5 minutes to a stirred mixture of N-tert-butoxycarbonyl-4-hydroxypiperidine (2 g), ethyl 3-hydroxybenzoate (1.66 g), triphenylphosphine (3.2 g) and THF (40 ml) which had been cooled to 0° C. The mixture was stirred at ambient temperature for 40 hours. The solvent was evaporated and the residue was triturated under a 9:1 mixture (40 ml) of isohexane and ethyl acetate. The mixture was filtered and the filtrate was evaporated. The residue was purified by column chromatography on silica using a 9:1 mixture (40 ml) of isohexane and ethyl acetate as eluent. There was thus obtained ethyl 3-(1-tert-butoxycarbonylpiperidin-4-yloxy)benzoate as an oil (1.82 g); NMR Spectrum: (CDCl$_3$) 1.41 (t, 3H), 1.46 (s, 9H), 1.93 (m, 2H), 3.38 (m, 2H), 3.7 (m, 2H), 4.36 (q, 2H), 4.52 (m, 1H), 7.1 (m, 1H), 7.35 (t, 3H), 7.58 (s, 1H), 7.62 (d, 1H).

Sodium hydroxide solution (10M; 1.0 ml) was added to a solution in ethanol (10 ml) of the ester so obtained and the mixture was stirred at ambient temperature for 18 hours. The mixture was evaporated and the residue was dissolved in water (5 ml). A 1M aqueous hydrochloric acid solution (10 ml) and glacial acetic acid (1 ml) were added in turn and the mixture was extracted with methylene chloride. The organic phase was dried over magnesium sulphate and evaporated to give the required starting material as a colourless solid (1.32 g), m.p. 148-150° C.; Mass Spectrum: M+H+ 322.

EXAMPLE 21

3-(3-acetoxybenzamido)-4-chloro-N-(3-fluoro-5-morpholinophenyl)benzamide

Oxalyl chloride (0.7 ml) was added to a stirred mixture of 3-acetoxybenzoic acid (1.242 g), DMF (1 ml) and methylene chloride (40 ml) and the solution was stirred at ambient temperature for 2 hours. The mixture was evaporated and a solution of 3-amino-4-chloro-N-(3-fluoro-5-morpholinophenyl) benzamide (2 g) and pyridine (10 ml) was added to the residue. The resultant mixture was stirred and heated to 100° C. for 18 hours. The mixture was cooled to ambient temperature and washed in turn with an aqueous acetic acid solution, with water and with a saturated aqueous sodium bicarbonate solution, dried over magnesium sulphate and evaporated. The residue was purified by column chromatography on silica gel using a 49:1 mixture of methylene chloride and methanol as eluent. There was thus obtained the title compound (1.3 g); NMR Spectrum: (DMSOd$_6$) 2.3 (s, 3H), 3.15 (t, 4H), 3.7 (t, 4H), 6.55 (d, 1H), 7.18 (m, 2H), 7.38 (m, 1H), 7.6 (t, 1H), 7.72 (m, 2H), 7.89 (m, 2H), 8.16 (s, 1H), 10.3 (d, 2H); Mass Spectrum: M+H+ 512.

The 3-amino-4-chloro-N-(3-fluoro-5-morpholinophenyl) benzamide used as a starting material was prepared as follows:

A mixture of 3,5-difluoronitrobenzene (31.1 g) and morpholine (85.2 g) was stirred and heated at 100° C. for 66 hours. The mixture was evaporated and the residue was purified by column chromatography on silica gel using a 4:1 mixture of isohexane and ethyl acetate as eluent. There was thus obtained 3-fluoro-5-morpholinonitrobenzene (33.3 g); NMR Spectrum: (DMSOd$_6$) 3.2-3.3 (m, 4H), 3.6-3.8 (m, 4H), 7.25 (m, 1H), 7.37 (m, 1H), 7.5 (m, 1H).

A mixture of the material so obtained, 10% palladium-on-carbon (3.3 g) and ethanol (1400 ml) was stirred under an atmosphere pressure of hydrogen gas for 16 hours. The mixture was filtered and the filtrate was evaporated to give 3-fluoro-5-morpholinoaniline (27.5 g); NMR Spectrum: (DMSOd$_6$) 2.9-3.05 (m, 4H), 3.6-3.7 (m, 4H), 5.15 (s, 2H), 5.75-5.9 30 (m, 3H).

A solution of 4-chloro-3-nitrobenzoyl chloride (41.2 g) in methylene chloride (120 ml) was added to a mixture of 3-fluoro-5-morpholinoaniline (27 g), triethylamine (52.6 ml) and methylene chloride (600 ml) which had been cooled in an ice-bath. The resultant mixture was stirred at ambient temperature for 16 hours. The mixture was evaporated. Methylene chloride and a saturated aqueous sodium bicarbonate solution were added and the resultant precipitate was isolated, washed with diethyl ether and dried under vacuum. There was thus obtained 4-chloro-3-nitro-N-(3-fluoro-5-morpholinophenyl)benzamide (36.1 g); NMR Spectrum: (DMSOd$_6$) 3.05-3.15 (m, 4H), 3.7-3.75 (m, 4H), 6.5-6.6 (m, 1H), 7.1-7.2 (m, 2H), 7.95 (d, 1H), 8.2-8.3 (m, 1H), 8.6 (s, 1H).

A mixture of the material so obtained, iron powder(50.6 g), glacial acetic acid (19 ml), water(95 ml) and ethanol (600 ml) was stirred and heated to reflux for 6 hours. The mixture was cooled to ambient temperature and water was added. The mixture was carefully basified to pH9 by the addition of a saturated aqueous sodium bicarbonate solution and extracted with ethyl acetate. The organic phase was dried over magnesium sulphate and evaporated to give the required starting material (24.3 g); NMR Spectrum: (DMSOd$_6$) 3.0-3.1 (m, 4H), 3.7-3.75 (m, 4H), 5.6 (s, 1H), 6.45-6.55 (m, 1H), 7.0-7.2 (m, 3H), 7.3-7.35 (m, 2H), 10.09 (br s, 1H); Mass Spectrum: M+H+ 350.

EXAMPLE 22

4-chloro-N-(3-fluoro-5-morpholinophenyl)-3-(3-hydroxybenzamido)benzamide

Sodium methoxide (95%, 0.26 g) was added to a stirred solution of 3-(3-acetoxybenzamido)-4-chloro-N-(3-fluoro-5-morpholinophenyl)benzamide (1.23 g) in methanol (75 ml) which had been cooled to 0° C. The resultant solution was stirred at ambient temperature for three hours. The mixture was concentrated by evaporation to a volume of about 15 ml and water (20 ml) was added. The solution was acidified to pH3 by the addition of 1N aqueous hydrochloric acid solution. The precipitate so formed was isolated and dried under vacuum. There was thus obtained the title compound (0.86 g); NMR Spectrum: (DMSOd$_6$) 2.47 (s, 3H), 3.08 (t, 4H), 3.7 (t, 4H), 6.53 (d, 1H), 6.98 (m, 1H), 7.14 (s, 1H), 7.19 (d, 1H), 7.33 (m, 1H), 7.42 (d, 1H), 7.70 (d, 1H), 7.84 (m, 1H), 8.15 (d, 1H), 9.75 (s, 1H), 10.08 (s, 1H), 10.29 (s, 1H); Mass Spectrum: M+H+ 470.

EXAMPLE 23

3-[2-amino-5-(4-methylpiperazin-1-yl)benzamido]-4-chloro-N-(3-fluoro-5-morpholinophenyl)benzamide Iron powder (0.726 g) was added to a stirred suspension of 4-chloro-N-(3-fluoro-5-morpholinophenyl)-3-[5-(4-methylpiperazin-1-yl)-2-nitrobenzamido]benzamide (0.76 g), water (2 ml), acetic acid (0.5 ml) and ethanol (15 ml) and the resultant mixture was stirred and heated to reflux for 1 hour. The mixture was cooled to ambient temperature. Water (80 ml) was added and the mixture was basified by the addition of sodium carbonate. The resultant mixture was filtered through diatomaceous earth and the separated solids were washed in turn with methylene chloride and methanol. The combined filtrates were evaporated and the residue was triturated under ethyl acetate. The mixture was filtered and the filtrate was evaporated to give the title compound (0.385 g); Mass Spectrum: M+H$^+$ 567.

The 4-chloro-N-(3-fluoro-5-morpholinophenyl)-3-[5-(4-methylpiperazin-1-yl)-2-nitrobenzamido]benzamide used as a starting material was prepared as follows:

Oxalyl chloride (1.05 ml) was added dropwise to a stirred mixture of 5-chloro-2-nitrobenzoic acid (2.08 g), methylene chloride (100 ml) and DMF (a few drops) which had been cooled to 0° C. The mixture was allowed to warm to ambient temperature and was stirred for four hours. The mixture was evaporated and the residue was dissolved in methylene chloride (10 ml) and added dropwise to a stirred mixture of 3-amino-4-chloro-N-(3-fluoro-5-morpholinophenyl)benzamide (3.0 g) and pyridine (40 ml). The resultant mixture was heated at 80° C. for 16 hours. The solvent was evaporated and the residue was dissolved in methylene chloride (50 ml) and water (50 ml) and stirred for one hour. The resultant solid was filtered, washed with water and diethyl ether and dried under vacuum at 40° C. There was thus obtained 4-chloro-3-(5-chloro-2-nitrobenzamido)-N-(3-fluoro-5-morpholinophenyl)benzamide (1.07 g); NMR Spectrum: (DMSOd$_6$) 3.09-3.14 (m, 4H), 3.69-3.74 (m, 4H), 6.58 (d, 1H), 7.15-7.2 (m, 2H), 7.71 (d, 1H), 7.82-7.92 (m, 3H), 8.2 (d, 1H), 8.29 (s, 1H), 10.37 (s, 1H), 10.61 (s, 1H); Mass Spectrum: M+H$^+$ 533 and 535.

A portion (0.8 g) of the material so obtained was dissolved in 1-methylpiperazine (3 ml) and the mixture was stirred and heated to 100° C. for 16 hours. The mixture was cooled and poured into water. The resultant solid was isolated, washed in turn with water and diethyl ether and dried under vacuum at 40° C. There was thus obtained the required starting material (0.803 g); NMR Spectrum: (DMSOd$_6$) 2.21 (s, 3H), 2.4-2.45 (m, 4H), 3.08-3.13 (m, 4H), 3.46-3.5 (m, 4H), 3.69-3.74 (m, 4H), 6.58 (d, 1H), 6.84 (s, 1H), 7.0-7.2 (m, 4H), 7.68 (d, 1H), 7.80 (d, 1H), 8.04 (d, 1H), 8.36 (s, 1H); Mass Spectrum: M+H$^+$ 597.

EXAMPLE 24

4-chloro-3-[5-(3-dimethylaminopropylamino)-2-nitrobenzamido]-N-(3-fluoro-5-morpholinophenyl)benzamide Using an analogous procedure to that described in the second paragraph of the portion of Example 23 which is concerned with the preparation of starting materials, 4-chloro-3-(5-chloro-2-nitrobenzamido)-N-(3-fluoro-5-morpholinophenyl)benzamide was reacted with 3-dimethylaminopropylamine to give the title compound in 76% yield; NMR Spectrum: (DMSOd$_6$) 1.62-1.74 (m, 2H), 2.12 (s, 6H), 2.27 (t, 2H), 3.08-3.13 (m, 4H), 3.18-3.22 (m, 2H), 3.69-3.74 (m, 4H), 6.58 (d, 1H), 6.67 (m, 2H), 7.15-7.2 (m, 2H), 7.42 (t, 1H), 7.69 (d, 1H), 7.68 (d, 1H), 7.82 (d, 1H), 8.04 (d, 1H), 8.26 (s, 1H), 10.32 (s, 1H); Mass Spectrum: M+H$^+$ 599.

EXAMPLE 25

3-[2-amino-5-(3-dimethylaminopropylamino)benzamido]-4-chloro-N-(3-fluoro-5-morpholinophenyl)benzamide Using an analogous procedure to that described in Example 23, 4-chloro-3-[5-(3-dimethylaminopropylamino)-2-nitrobenzamido]-N-(3-fluoro-5-morpholinophenyl)benzamide was reduced to give the title compound; NMR Spectrum: (DMSOd$_6$) 1.62-1.78 (m, 2H), 2.15 (s, 6H), 2.33 (t, 2H), 2.99 (t, 2H), 3.09-3.13 (m, 4H), 3.69-3.74 (m, 4H), 6.56 (d, 1H), 6.66 (s, 2H), 6.94 (s, 1H), 7.15-7.22 (m, 3H), 7.68 (d, 1H), 7.78 (d, 1H), 8.32 (s, 1H), 10.29 (s, 1H); Mass Spectrum: M+H$^+$ 569.

EXAMPLE 26

3-{2-amino-5-[N-(3-methylaminopropyl)-N-methylamino]benzamido}-4-chloro-N-(3-fluoro-5-morpholinophenyl)benzamide Using an analogous procedure to that described in Example 23, 4-chloro-N-(3-fluoro-5-morpholinophenyl)-3-{5-[N-(3-methylaminopropyl)-N-methylamino]-2-nitrobenzamido}benzamide was reduced to give the title compound; Mass Spectrum: M+H$^+$ 569 and 571.

The starting material was prepared by the reaction of 4-chloro-3-(5-chloro-2-nitrobenzamido)-N-(3-fluoro-5-morpholinophenyl)benzamide with N-(3-methylaminopropyl)-N-methylamine using an analogous procedure to that described in the second paragraph of the portion of Example 23 which is concerned with the preparation of starting materials; NMR Spectrum: (DMSOd$_6$) 1.62-1.74 (m, 2H), 2.25 (s, 3H), 2.46-2.49 (m, 2H), 3.07 (s, 3H), 3.12 (t, 2H), 3.55 (t, 2H), 3.69-3.74 (m, 4H), 6.58 (d, 1H), 6.79 (s, 1H), 6.86 (d, 1H), 7.16-7.2 (m, 2H), 7.69 (d, 1H), 7.82 (d, 1H), 8.12 (s, 1H); Mass Spectrum: M+H$^+$ 599.

EXAMPLE 27

3-{2-amino-5-[N-(3-dimethylaminopropyl)-N-methylamino]benzamido}-4-chloro-N-(3-fluoro-5-morpholinophenyl)benzamide Using an analogous procedure to that described in Example 23, 4-chloro-N-(3-fluoro-5-morpholinophenyl)-3-{5-[N-(3-dimethylaminopropyl)-N-methylamino]-2-nitrobenzamido}benzamide was reduced to give the title compound; NMR Spectrum: (DMSOd$_6$) 1.54-1.62 (m, 2H), 2.1 (s, 6H), 2.18-2.22 (m, 2H), 2.77 (s, 3H), 3.09-3.16 (m, 4H), 3.18-3.22 (m, 2H), 3.7-3.74 (m, 4H), 6.57 (d, 1H), 6.7 (d, 1H), 6.84 (d, 1H), 7.08-7.24 (m, 3H), 7.7 (d, 1H), 7.8 (d, 1H), 8.27 (s, 1H); Mass Spectrum: M+H$^+$ 583.

The starting material was prepared by the reaction of 4-chloro-3-(5-chloro 2-nitrobenzamido)-N-(3-fluoro-5-morpholinophenyl)benzamide with N-(3-dimethylaminopropyl)-N-methylamine using an analogous procedure to that described in the second paragraph of the portion of Example 23 which is concerned with the preparation of starting materials; NMR Spectrum: (DMSOd$_4$) 1.62-1.74 (in, 2H), 2.12 (s, 6H), 2.21 (t, 2H), 3.08 (s, 3H), 3.1-3.13 (m, 4H), 3.52 (t, 2H), 3.71-3.74 (m, 4H), 6.68 (d, 1H), 6.78 (s, 1H), 6.84 (d, 1H), 7.16-7.20 (m, 2H), 7.68 (d, 1H), 7.82 (d, 1H), 8.04 (d, 1H), 8.31 (s, 1H); Mass Spectrum: M+H$^+$ 613 and 615.

EXAMPLE 28

Using an analogous procedure to that described in Example 1 or 2, the appropriate benzoyl chloride (prepared by reaction of the corresponding benzoic acid with oxalyl chloride using an analogous procedure to that described in the first part of the portion of Example 1 which is concerned with the preparation of starting materials) was reacted with the appropriate aniline to give the compounds described in Table II.

ylnitrobenzene (24 g); NMR Spectrum: (DMSOd$_6$) 1.93-1.98 (m, 4H), 3.25-3.3 (m, 4H), 6.72-6.76 (m, 1H), 7.07-7.15 (m, 2H).

A mixture of the material so obtained, 10% palladium-on-carbon (3 g) and methanol (500 ml) was stirred under an atmosphere pressure of hydrogen gas until uptake of hydrogen ceased. The mixture was filtered and the filtrate was evaporated. The residue was purified by column chromatography on silica gel using a 10:3 mixture of isohexane and ethyl acetate as eluent. There was thus obtained 3-fluoro-5-pyrrolidin-1-ylaniline (14.8 g); NMR Spectrum: (DMSOd$_6$) 1.87-1.92 (m, 4H), 3.09-3.14 (m, 4H), 5.04 (s, 2H), 5.47-5.62 (m, 3H).

TABLE II

| No. | (R$^1$)$_m$ | R$^3$ | R | Method | Note |
|---|---|---|---|---|---|
| 1 | 2,4-dimethoxy | methyl | 3-dimethylamino | Ex. 2 | (a) |
| 2 | 3,4-diethoxy | methyl | 3-dimethylamino | Ex. 1 | (b) |
| 3 | 4-(2-ethoxyethoxy) | methyl | 3-dimethylamino | Ex. 1 | (c) |
| 4 | 3,4-dimethoxy | methyl | 3-morpholino | Ex. 1 | (d) |
| 5 | 3,4,5-trimethoxy | methyl | 3-morpholino | Ex. 1 | (e) |
| 6 | 3-chloromethyl | methyl | 3-morpholino | Ex. 1 | (f) |
| 7 | 4-chloromethyl | methyl | 3-morpholino | Ex. 1 | (g) |
| 8 | 3-chloromethyl | chloro | 3-fluoro-5-morpholino | Ex. 1 | (h) |
| 9 | 4-chloromethyl | chloro | 3-fluoro-5-morpholino | Ex. 1 | (i) |
| 10 | 3-chloromethyl | methyl | 3-fluoro-5-pyrrolidin-1-yl | Ex. 1 | (j) |
| 11 | 4-chloromethyl | methyl | 3-fluoro-5-pyrrolidin-1-yl | Ex. 1 | (k) |

Notes (a) The product was purified by column chromatography on an ion exchange column (isolute SCX column from International Sorbent Technology Limited, Hengoed, Mid-Glamorgan, UK) using a 99:1 mixture of methanol and a saturated aqueous ammonium hydroxide solution as eluent and gave the following data: NMR Spectrum: (DMSOd$_6$) 2.4(s, 3H), 2.98(s, 6H), 3.89(s, 3H), 4.07(s, 3H), 6.52(d, 1H), 6.56(s, 1H), 6.69(d, 1H), 6.94(d, 1H), 7.12(m, 2H), 7.33(d, 1H), 7.7(d, 1H), 7.96(br s, 1H), 8.29(d, 1H), 8.81(s, 1H), 9.83 (br s, 1H); Mass Spectrum: M + H$^+$ 434.

(b) The product gave the following data: Mass Spectrum: M + H$^+$ 462.

(c) The reaction product was triturated under diethyl ether and the solid so obtained was dried under vacuum at 40° C. The resultant product gave the following data: NMR Spectrum: (DMSOd$_6$) 1.12(t, 3H), 2.28(s, 3H), 2.87(s, 6H), 3.5(m, 2H), 3.71(m, 2H), 7.21(d, 1H), 4.20(m, 2H), 6.43(d, 1H), 7.12(m, 5H); 7.4(d, 1H), 7.9(d, 1H); 7.95(m, 3H), 9.84(br s, 1H), 10.05(br s, 1H); Mass Spectrum: M + H$^+$ 462.

(d) The product gave the following data: NMR Spectrum: (DMSOd$_6$)2.3(s, 3H), 3.05-3.1(m, 4H), 3.7-3.75(m, 4H), 3.85(s, 6H), 6.65-6.7(m, 1H), 7.05-7.2(m, 2H), 7.25-7.3(m, 1H), 7.35-7.45(m, 2H), 7.55-7.6(m, 1H), 7.6-7.7(m, 1H), 7.75-7.8(m, 1H), 7.95(s, 1H), 9.9(s, 1H), 10.0-10.02(s, 1H); Mass Spectrum: M + H$^+$ 476.

(e) The product gave the following data: NMR Spectrum: (DMSOd$_6$)2.3(s, 3H), 3.05-3.1(m, 4H), 3.7-3.75(m, 7H), 3.85(s, 6H), 6.65-6.75(m,1H), 7.17(t, 1H), 7.3-7.5(m, 5H), 7.75-7.85(m, 1H), 7.85(s, 1H), 10.0(s,1H), 10.01-10.03(s, 1H); Mass Spectrum: M + H$^+$ 506.

(f) The product gave the following data: NMR Spectrum: (CDCl$_3$)2.4(s, 3H), 3.1-3.2(m, 4H), 3.7-3.9(m, 4H), 4.65(s, 2H), 6.65-6.75(m, 1H), 7.0-7.05(m, 1H), 7.25(t, 1H), 7.35(d, 1H), 7.45-7.75(m, 4H), 7.95(s, 2H), 8.15-8.2(m, 1H), 8.3(s, 1H); Mass Spectrum: M + H$^+$ 464.

(g) The product gave the following data: Mass Spectrum: M + H$^+$ 464.

(h) The reaction mixture was evaporated and the residue was triturated under water. The solid so obtained was washed with one equivalent of dilute aqueous hydrochloric acid and dried under vacuum at 40° C. The resultant product gave the following data: NMR Spectrum: (DMSOd$_6$)3.11(m, 4H), 3.72(m, 4H), 4.86(s, 2H), 6.54(d, 1H), 7.14(s, 1H), 7.19(d, 1H), 7.56(t, 1H), 7.71(m, 2H), 7.87(d, 1H), 7.97(d, 1H), 8.06(s, 1H), 8.14(s, 1H), 10.3(br s, 2H); Mass Spectrum: M + H$^+$ 502.

(i) The reaction mixture was evaporated and the residue was triturated under water. The solid so obtained was washed with one equivalent of dilute aqueous hydrochloric acid and dried under vacuum at 40° C. The resultant product gave the following data: NMR Spectrum: (DMSOd$_6$)3.11(m, 4H), 3.72(m, 4H), 4.84(s, 2H), 6.54(d, 1H), 7.15(s, 1H), 7.2(d, 1H), 7.6(d, 2H), 7.72(d 1H), 7.87(d, 1H), 8.0(d, 2H), 8.15(s, 1H), 10.26(s, 1H), 10.31(s, 1H); Mass Spectrum: M + H$^+$ 502.

(j) The product gave the following data: NMR Spectrum: (DMSOd$_6$)1.94(m, 4H), 2.31(s, 3H), 3.2(m, 4H), 4.86(s, 2H), 6.06(d, 1H), 6.8(s, 1H), 7.02(d, 1H), 7.43(d, 1H), 7.55(t, 1H), 7.67(d, 1H), 7.79(d, 1H), 7.94(d, 1H), 7.97(d, 1H), 8.05(s, 1H), 10.1(m, 2H); Mass Spectrum: M + H$^+$ 466.

The 3-amino-N-(3-fluoro-5-pyrrolidin-1-ylphenyl)-4-methylbenzamide used as a starting material was prepared as follows A mixture of 3,5-difluoronitrobenzene (20 g) and pyrrolidine (63 ml) was stirred and heated at 100° C. for 4 hours. The mixture was cooled to ambient temperature and poured into water (100 ml). The resultant solid was isolated, washed in turn with water and with diethyl ether and dried under vacuum. There was thus obtained 3-fluoro-5-pyrrolidin-1-

4-Methyl-3-nitrobenzoyl chloride (14.5 ml) was added to a mixture of 3-fluoro-5-pyrrolidin-1-ylaniline (14.8 g), triethylamine (25.2 ml) and methylene chloride (300 ml) and the resultant mixture was stirred at ambient temperature for 18 hours. Water (200 ml) was added and the resultant solid was isolated, washed in turn with water and with diethyl ether and dried under vacuum. There was thus obtained 4-methyl-N-(3-fluoro-5-pyrrolidin-1-yl)-3-nitrobenzamide (19.3 g); NMR Spectrum: (DMSOd$_6$) 1.92-1.97 (m, 4H), 2.58 (s, 3H), 3.18-3.23 (m, 4H), 6.09 (d, 1H), 6.77 (s, 1H), 7.99 (d, 1H), 7.66 (d, 1H), 8.16 (d, 1H) 8.53 (s, 1H), 10.33 (s, 1H).

A mixture of the material so obtained, 10% palladium-on-carbon (2 g) and methanol (300 ml) was stirred under an atmosphere pressure of hydrogen gas until uptake of hydrogen ceased. The mixture was filtered and the filtrate was evaporated. The residue was triturated under a mixture of diethyl ether and ethyl acetate. The resultant solid was isolated, washed in turn with water and with diethyl ether and dried under vacuum. There was thus obtained the required starting material (14.4 g); NMR Spectrum: (DMSOd$_6$) 1.91-1.97 (m, 4H), 2.1 (s, 3H), 3.14-3.21 (m, 4H), 5.03 (s, 2H), 6.02 (d, 1H), 6.8 (s, 1H), 6.98-7.06 (m, 3H), 7.13 (s, 1H), 9.87 (s, 1H); Mass Spectrum: M+H$^+$ 314.

(k) The product gave the following data: NMR Spectrum: (DMSOd$_6$) 1.95 (m, 4H), 2.31 (s, 3H), 3.21 (m, 4H), 4.85 (s, 2H), 6.06 (d, 1H), 6.81 (s, 1H), 7.02 (d, 1H), 7.42 (d, 1H), 7.6 (d, 2H), 7.79 (d, 1H), 7.99 (m, 3H), 10.06 (s, 1H), 10.1 (s, 1H); Mass Spectrum: M+H$^+$ 466.

EXAMPLE 29

Using an analogous procedure to that described in Example 5, an appropriate amino-substituted alkyl chloride was reacted with the appropriate phenol to give the compounds described in Table III.

TABLE III

| No. | (R$^1$)$_m$ | R$^3$ | R | Note |
|---|---|---|---|---|
| 1 | 3-(2-diethylaminoethoxy) | methyl | 3-morpholino | (a) |
| 2 | 3-(3-diethylaminopropoxy) | methyl | 3-morpholino | (b) |
| 3 | 3-(2-diisopropylaminoethoxy) | methyl | 3-morpholino | (c) |
| 4 | 3-(2-pyrrolidin-1-ylethoxy) | methyl | 3-morpholino | (d) |
| 5 | 3-(2-piperidinoethoxy) | methyl | 3-morpholino | (e) |
| 6 | 3-(3-piperidinopropoxy) | methyl | 3-morpholino | (f) |
| 7 | 3-(N-methylpiperidin-3-ylmethoxy) | methyl | 3-morpholino | (g) |
| 8 | 3-(2-methylthiazol-4-ylmethoxy) | methyl | 3-morpholino | (h) |
| 9 | 3-(2-diethylaminoethoxy) | chloro | 3-fluoro-5-morpholino | (i) |
| 10 | 3-(2-piperidinoethoxy) | chloro | 3-fluoro-5-morpholino | (j) |
| 11 | 3-[2-(N-methylpyrrolidin-2-yl)ethoxy] | chloro | 3-fluoro-5-morpholino | (k) |
| 12 | 3-(N-methylhomopiperidin-4-yloxy) | chloro | 3-fluoro-5-morpholino | (l) |

Notes (a) The reactants were 2-diethylaminoethyl chloride and 3-(3-hydroxybenzamido)-4-methyl-N-(3-morpholinophenyl)benzamide. The product gave the following data: NMR Spectrum: (DMSOd$_6$) 0.97(t, 6H), 2.27(s, 3H), 2.55(m, 4H), 2.8(t, 2H), 3.08(t, 4H), 3.72(t, 4H), 4.07(t, 2H), 6.68(m, 1H), 7.17(m, 2H), 7.29(d, 1H), 7.4(m, 3H), 7.56(m, 2H), 7.78(m, 1H), 7.92(s, 1H), 10.0(s, 1H), 10.02(s, 1H); Mass Spectrum: M + H$^+$ 531.
(b) The product gave the following data: NMR Spectrum: (DMSOd$_6$) 0.92(t, 6H), 1.92(m, 2H), 2.27(s, 3H), 2.47(m, 6H), 3.06(t, 4H), 3.72(t, 4H), 4.04(t, 2H), 6.67(m, 1H), 7.17(m, 2H), 7.28(m, 1H), 7.41(m, 3H), 7.55(m, 2H), 7.78(m, 1H), 7.92(s, 1H), 10.0(s, 1H), 10.02(s, 1H); Mass Spectrum: M + H$^+$ 545.
(c) The product gave the following data: NMR Spectrum: (DMSOd$_6$) 0.99(m, 12H), 2.27(s, 3H), 2.78(m, 2H), 3.04(m, 6H), 3.74(br s, 4H), 3.95(t, 2H), 6.68(d, 1H), 7.15(m, 2H), 7.28(m, 1H), 7.4(m, 3H), 7.55(m, 2H), 7.79(d, 1H), 7.92(s, 1H), 10.0(s, 1H), 10.01(s, 1H); Mass Spectrum: M + H$^+$ 559.
(d) The product gave the following data: NMR Spectrum: (DMSOd$_6$) 1.64(m, 4H), 2.28(s, 3H), 2.5(m, 4H), 2.81(t, 3H), 3.05(t, 4H), 3.73(t, 4H), 4.16(t, 2H), 6.66(m, 1H), 7.17(m, 2H), 7.28(d, 1H), 7.4(m, 3H), 7.57(m, 2H), 7.79(m, 1H), 7.93(s, 1H), 10.0(s, 1H), 10.02(s, 1H); Mass Spectrum: M + H$^+$ 529.
(e) The product gave the following data: NMR Spectrum: (DMSOd$_6$) 1.36(m, 2H), 1.49(m, 4H), 2.17(s, 3H), 2.43(t, 4H), 2.64(t, 2H), 3.06(t, 4H), 3.73(t, 4H), 4.12(t, 2H), 6.66(m, 1H), 7.16(m, 2H), 7.28(d, 1H), 7.4(m, 3H), 7.56(m, 2H), 7.78(m, 1H), 7.91(s, 1H), 10.0(s, 1H), 10.02(s, 1H); Mass Spectrum: M + H$^+$ 543.
(f) The product gave the following data: NMR Spectrum: (DMSOd$_6$) 1.36(m, 2H), 1.46(m, 4H), 1.84(m, 2H), 2.34(br m, 9H), 3.05(t, 4H), 3.72(t, 4H), 4.06(t, 2H), 6.67(m, 1H), 7.16(m, 2H), 7.29(d, 1H), 7.41(m, 3H), 7.55(m, 2H), 7.78(d, 1H), 7.92(s, 1H), 10.0(s, 1H), 10.02(s, 1H); Mass Spectrum: M + H$^+$ 557.
(g) The product gave the following data: NMR Spectrum: (DMSOd$_6$) 1.09(m, 1H), 1.7(br m, 6H), 2.16(s, 3H), 2.28(s, 3H), 2.41(m, 1H), 2.81(d, 1H), 3.06(t, 4H), 3.72(t, 4H), 3.92(m, 2H), 6.67(d, 1H), 7.17(m, 2H), 7.3(d, 1H), 7.41(m, 3H), 7.55(m, 2H), 7.79(d, 1H), 7.93(s, 1H), 10.0(s, 1H), 10.02(s, 1H); Mass Spectrum: M + H$^+$ 543.
(h) The product gave the following data: NMR Spectrum: (DMSOd$_6$) 2.27(s, 3H), 2.63(s, 3H), 3.05(t, 4H), 3.71(t, 4H), 5.19(s, 2H), 6.66(m, 1H), 7.17(t, 1H), 7.24(m, 2H), 7.41(m, 3H), 7.59(m, 3H), 7.94(s, 1H), 10.0(s, 1H), 10.02(s, 1H); Mass Spectrum: M + H$^+$ 543.
(i) The reactants were 2-diethylaminoethyl chloride and 4-chloro-N-(3-fluoro-5-morpholinophenyl)-3-(3-hydroxybenzamido)benzamide. The product gave the following data: NMR Spectrum: (DMSOd$_6$) 0.96(t, 6H), 2.55(m, 4H), 2.79(t, 2H), 3.09(t, 4H), 3.7(t, 4H), 4.08(t, 2H), 6.53(d, 1H), 7.18(m, 3H), 7.43(t, 1H), 7.57(m, 2H), 7.71(d, 1H), 7.83(m, 1H), 8.15(d, 1H), 10.19(s, 1H), 10.29(s, 1H); Mass Spectrum: M + H$^+$ 569.
(j) The product gave the following data: NMR Spectrum: (DMSOd$_6$) 1.35(d, 2H), 1.48(m, 4H), 2.42(m, 4H), 2.65(t, 2H), 3.1(t, 4H), 3.7(t, 4H), 4.13(t, 2H), 6.52(d, 1H), 7.18(m, 3H), 7.43(t, 1H), 7.55(m, 2H), 7.7(d, 1H), 7.84(m, 1H), 8.15(d, 1H), 10.18(s, 1H), 10.29(s, 1H); Mass Spectrum: M + H$^+$ 581.
(k) The reactants were 2-(N-methylpyrrolidin-2-yl)ethyl chloride and 4-chloro-N-(3-fluoro-5-morpholinophenyl)-3-(3-hydroxybenzamido)benzamide. The reaction product was purified by column chromatography on silica gel using increasingly polar mixtures of methylene chloride and methanol as eluent. The product gave the following data: NMR Spectrum: (DMSOd$_6$) 1.5(br m, 4H), 1.9(m, 1H), 2.05(m, 3H), 2.22(s, 3H), 2.93(m, 1H), 3.09(t, 4H), 3.71(t, 4H), 4.08(t, 2H), 6.54(dm, 1H), 7.18(m, 2H), 7.42(t, 1H), 7.55(m, 2H), 7.7(d, 1H), 7.86(d, 1H), 8.12(d, 1H), 10.19(s, 1H), 10.29(s, 1H); Mass Spectrum: M + H$^+$ 581.
(l) As for Example 29(11), the reactants were 2-(N-methylpyrrolidin-2-yl)ethyl chloride and 4-chloro-N-(3-fluoro-5-morpholinophenyl)-3-(3-hydroxybenzamido)benzamide and the reaction product was purified by column chromatography on silica gel using increasingly polar mixtures of methylene chloride and methanol as eluent. The compound of Example 29(11) was eluted first. On further elution the isomeric compound of Example 29(12) was eluted. This product gave the following data: NMR Spectrum: (DMSOd$_6$) 1.57(m, 1H), 1.78(br m, 3H), 2.04(m, 2H), 2.23(s, 3H), 2.6(br m, 4H), 3.1(t, 3H), 3.71(t, 4H), 4.66(t, 1H), 6.53(m, 1H), 7.11(m, 2H), 7.2(d, 1H), 7.42(t, 1H), 7.5(m, 1H), 7.7(d, 1H), 7.85(m, 1H), 8.13(d, 1H), 10.17(s, 1H), 10.29(s, 1H); Mass Spectrum: M + H$^+$ 581.

EXAMPLE 30

4-methyl-3-[3-(4-methylpiperazin-1-ylmethyl)benzamido]-N-(3-morpholinophenyl)benzamide N-Methylpiperazine (0.036 g) was added to a mixture of 3-(3-chloromethylbenzamido)-4-methyl-N-(3-morpholinophenyl)benzamide (0.15 g), potassium carbonate (0.09 g) and acetone (5 ml) and the resultant mixture was stirred and heated to 60° C. for 16 hours. The mixture was evaporated and the residue was partitioned between methylene chloride and a saturated aqueous sodium bicarbonate solution. The organic phase was dried over magnesium sulphate and evaporated. The residue was purified by column chromatography on silica gel using methanol as eluent. The product so obtained was dissolved in ethyl acetate and precipitated by the addition of isohexane. There was thus obtained the title compound (0.071 g); NMR Spectrum: (DMSOd$_6$) 2.1 (s, 3H), 2.3 (s, 3H), 2.2-2.4 (m, 8H), 3.1 (t, 4H), 3.55 (s, 2H), 3.75 (t, 4H), 6.65-6.7 (m, 1H), 7.18 (t, 1H), 7.3-7.35 (m, 1H), 7.38-7.55 (m, 4H), 7.78-7.8 (m, 1H), 7.85-7.9 (m, 2H), 7.95 (s, 1H); Mass Spectrum: M+H$^+$ 528.

EXAMPLE 31

Using an analogous procedure to that described in Example 30, the appropriate chloromethyl-substituted benzamide was reacted with the appropriate amine to give the compounds described in Table IV.

TABLE IV

| No. | (R$^1$)$_m$ | R$^3$ | R | Note |
|---|---|---|---|---|
| 1 | 3-(4-methylhomopiperazin-1-ylmethyl) | methyl | 3-morpholino | (a) |
| 2 | 3-diethylaminomethyl | methyl | 3-morpholino | (b) |
| 3 | 3-(2-morpholinoethylaminomethyl) | methyl | 3-morpholino | (c) |
| 4 | 4-diethylaminomethyl | methyl | 3-morpholino | (d) |
| 5 | 4-(4-methylpiperazin-1-ylmethyl) | methyl | 3-morpholino | (e) |
| 6 | 4-(4-methylhomopiperazin-1-ylmethyl) | methyl | 3-morpholino | (f) |
| 7 | 4-(2-morpholinoethylaminomethyl) | methyl | 3 -morpholino | (g) |
| 8 | 3-morpholinomethyl | methyl | 3-fluoro-5-pyrrolidin-1-yl | (h) |
| 9 | 3-piperazin-1-ylmethyl | methyl | 3-fluoro-5-pyrrolidin-1-yl | (i) |
| 10 | 3-(4-methylpiperazin-1-ylmethyl) | methyl | 3-fluoro-5-pyrrolidin-1-yl | (j) |
| 11 | 3-(4-isopropylpiperazin-1-ylmethyl) | methyl | 3-fluoro-5-pyrrolidin-l-yl | (k) |
| 12 | 3-(4-methylhomopiperazin-1-ylmethyl) | methyl | 3-fluoro-5-pyrrolidin-1-yl | (l) |
| 13 | 3-(3-hydroxypyrrolidin-1-ylmethyl) | methyl | 3-fluoro-5-pyrrolidin-1-yl | (m) |
| 14 | 3-[2-(N-dimethylaminoethyl)-N-methylaminomethyl] | methyl | 3-fluoro-5-pyrrolidin-1-yl | (n) |
| 15 | 3-(3-dimethylamino-2,2-dimethylpropylaminomethyl) | methyl | 3-fluoro-5-pyrrolidin-1-yl | (o) |
| 16 | 3-[3-(N-dimethylaminopropyl)-N-methylaminomethyl] | methyl | 3-fluoro-5-pyrrolidin-1-yl | (p) |
| 17 | 3-(2-methoxyethylaminomethyl) | methyl | 3-fluoro-5-pyrroLidin-1-yl | (q) |
| 18 | 3-(3-morpholinopropylaminomethyl) | methyl | 3-fluoro-5-pyrrolidm-1-yl | (r) |
| 19 | 3-(N-butyl-N-methylaminomethyl) | methyl | 3-fluoro-5-pyrrolidin-1-yl | (s) |
| 20 | 4-morpholinomethyl | methyl | 3-fluoro-5-pyrrolidin-1-yl | (t) |
| 21 | 4-(4-methylpiperazin-1-ylmethyl) | methyl | 3-fluoro-5-pyrrolidin-1-yl | (u) |
| 22 | 4-(4-isopropylpiperazin-1-ylmethyl) | methyl | 3-fluoro-5-pyrrolidin-1-yl | (v) |
| 23 | 4-(4-methylhomopiperazin-1-ylmethyl) | methyl | 3-fluoro-5-pyrrolidin-1-yl | (w) |
| 24 | 4-(3-hydroxypyrrolidin-1-ylmethyl) | methyl | 3-fluoro-5-pyrrolidin-1-yl | (x) |
| 25 | 4-[2-(N-dimethylaminoethyl)-N-methylaminomethyl] | methyl | 3-fluoro-5-pyrrolidin-1-yl | (y) |
| 26 | 4-(3-dimethylamino-2,2-dimethylpropylaminomethyl) | methyl | 3-fluoro-5-pyrrolidin-1-yl | (z) |
| 27 | 4-[3-(N-dimethylaminopropyl)-N-methylaminomethyl] | methyl | 3-fluoro-5-pyrrolidin-1-yl | (aa) |
| 28 | 4-(2-methoxyethylaminomethyl) | methyl | 3-fluoro-5-pyrrolidin-1-yl | (bb) |
| 29 | 4-(3-morpholinopropylaminomethyl) | methyl | 3-fluoro-5-pyrrolidin-1-yl | (cc) |
| 30 | 4-diethylaminomethyl | methyl | 3-fluoro-5-pyrrolidin-1-yl | (dd) |
| 31 | 4-(N-butyl-N-methylaminomethyl) | methyl | 3-fluoro-5-pyrrolidin-1-yl | (ee) |
| 32 | 3-morpholinomethyl | chloro | 3-fluoro-5-morpholino | (ff) |
| 33 | 3-piperazin-1-ylmethyl | chloro | 3-fluoro-5-morpholino | (gg) |
| 34 | 3-(4-methylpiperazin-1-ylmethyl) | chloro | 3-fluoro-5-morpholino | (hh) |
| 35 | 3-(4-isopropylpiperazin-1-ylmethyl) | chloro | 3-fluoro-5-morpholino | (ii) |
| 36 | 3-(4-methylhomopiperazin-1-ylmethyl) | chloro | 3-fluoro-5-morpholino | (jj) |
| 37 | 3-(3-hydroxypyrrolidin-1-ylmethyl) | chloro | 3-fluoro-5-morpholino | (kk) |
| 38 | 3-[2-(N-dimethylaminoethyl)-N-methylaminomethyl] | chloro | 3-fluoro-5-morpholino | (ll) |
| 39 | 3-(3-dimethylamino-2,2-dimethylpropylaminomethyl) | chloro | 3-fluoro-5-morpholino | (mm) |
| 40 | 3-[3-(N-dimethylaminopropyl)-N-methylaminomethyl] | chloro | 3-fluoro-5-morpholino | (nn) |
| 41 | 3-(2-methoxyethylaminomethyl) | chloro | 3-fluoro-5-morpholino | (oo) |
| 42 | 3-(3-morpholinopropylaminomethyl) | chloro | 3-fluoro-5-morpholino | (pp) |
| 43 | 3-(N-butyl-N-methylaminomethyl) | chloro | 3-fluoro-5-morpholmo | (qq) |
| 44 | 4-morpholinomethyl | chloro | 3-fluoro-5-morpholino | (rr) |
| 45 | 4-(4-methylpiperazin-1-ylmethyl) | chloro | 3-fluoro-5-morpholino | (ss) |
| 46 | 4-(4-methylhomopiperazin-1-ylmethyl) | chloro | 3-fluoro-5-morpholino | (tt) |
| 47 | 4-(3-hydroxypyrrolidin-1-ylmethyl) | chloro | 3-fluoro-5-morpholino | (uu) |
| 48 | 4-[2-(N-dimethylaminoethyl)-N-methylaminomethyl] | chloro | 3-fluoro-5-morpholino | (vv) |

TABLE IV-continued

| No. | $(R^1)_m$ | $R^3$ | R | Note |
|---|---|---|---|---|
| 49 | 4-(3-dimethylamino-2,2-dimethylpropylaminomethyl) | chloro | 3-fluoro-5-morpholino | (ww) |
| 50 | 4-[3-(N-dimethylaminopropyl)-N-methylaminomethyl] | chloro | 3-fluoro-5-morpholino | (xx) |
| 51 | 4-(2-methoxyethylaminomethyl) | chloro | 3-fluoro-5-morpholino | (yy) |
| 52 | 4-(3-morpholinopropylaminomethyl) | chloro | 3-fluoro-5-morpholino | (zz) |
| 53 | 4-diethylaminomethyl | chloro | 3-fluoro-5-morpholino | (aaa) |
| 54 | 4-(N-butyl-N-methylaminomethyl) | chloro | 3-fluoro-5-morpholino | (bbb) |

Notes (a) The product gave the following data: NMR Spectrum: (CDCl$_3$)1.8-1.9(m, 2H), 2.37(s, 3H), 2.4(s, 3H), 2.6-2.8(m, 8H), 3.2(t, 4H), 3.75(s, 1H), 3.85(t, 4H), 6.65-6.75(m, 1H), 7.0-7.05(m, 1H), 7.22(t, 1H), 7.35(d, 1H), 7.45-7.5(m, 2H), 7.55-7.6(m, 1H), 7.7-7.75(m, 1H), 7.75-7.8(m, 1H), 7.85-7.95(m, 2H), 8.07(s, 1H), 8.45(s, 1H); Mass Spectrum: M + H$^+$ 542.
(b) The product gave the following data: NMR Spectrum: M + H$^+$ 501.
(c) The product gave the following data: NMR Spectrum: (DMSOd$_6$)2.25-2.4(m, 9H), 2.55-2.65(m, 2H), 3.05-3.15(m, 4H), 3.5-3.6(m, 4H), 3.7-3.8(m, 6H), 6.65-6.75(m, 1H), 7.18(t, 1H), 7.3-7.35(m, 1H), 7.4-7.6(m, 4H), 7.75-7.8(m, 1H), 7.8-7.9(m, 1H), 7.95(s, 2H), 10.0-10.04(br d, 2H); Mass Spectrum: M + H$^+$ 558.
(d) The product gave the following data: NMR Spectrum: (DMSOd$_6$)0.9-1.0(m, 6H), 2.3(s, 3H), 2.4-2.6(m, 4H), 3.0-3.1(m, 4H), 3.5-3.7(m, 2H), 3.7-3.8(m, 4H), 6.65-6.75(m, 1H), 7.2(t, 1H), 7.25-7.3(m, 1H), 7.35-7.55(m, 4H), 7.75-7.8(m, 1H), 7.9-8.0(m, 3H), 10.0(s, 1H), 10.02(br s, 1H); Mass Spectrum: M + H$^+$ 501.
(e) The product gave the following data: NMR Spectrum: (DMSOd$_6$)2.1(s, 3H), 2.2-2.45(m, 11H), 3.05(t, 4H), 3.55(s, 2H), 3.75(t, 4H), 6.65-6.75(m, 1H), 7.15(t, 1H), 7.28-7.32(m, 1H), 7.35-7.48(m, 4H), 7.75-7.8(m, 1H), 7.95-8.0(m, 3H), 10.0(s, 1H), 10.03(s, 1H); Mass Spectrum: M + H$^+$ 528.
(f) The product gave the following data: NMR Spectrum: (DMSOd$_6$)1.65-1.75(m, 2H), 2.25(s, 3H), 2.3(s, 3H), 2.5-2.7(m, 8H), 3.05-3.15(m, 4H), 3.68(s, 2H), 3.7-3.8(m, 4H), 6.65-6.75(m, 1H), 7.17(t, 1H), 7.30-7.35(m, 1H), 7.4-7.5(m, 4H), 7.75-7.8(m, 1H), 7.9-8.0(m, 3H), 10.03(br s, 1H); Mass Spectrum: M + H$^+$ 542.
(g) The product gave the following data: NMR Spectrum: (DMSOd$_6$)2.25-2.4(m, 9H), 2.58(t, 2H), 3.05(t, 4H), 3.55(t, 4H), 3.72(t, 4H), 3.75(s, 2H), 6.65-6.75(m, 1H), 7.17(t, 1H), 7.25-7.3(m, 1H), 7.35-7.5(m, 4H), 7.75-7.8(m, 1H), 7.9-8.0(m, 3H), 10.0(s, 1H), 10.03(br s, 1H); Mass Spectrum: M + H$^+$ 558.
(h) The product gave the following data: NMR Spectrum: M + H$^+$ 517.
(i) The product gave the following data: NMR Spectrum: M + H$^+$ 516.
(j) The product gave the following data: NMR Spectrum: M + H$^+$ 530.
(k) The product gave the following data: NMR Spectrum: M + H$^+$ 558.
(l) The product gave the following data: NMR Spectrum: M + H$^+$ 544.
(m) The product gave the following data: NMR Spectrum: M + H$^+$ 517.
(n) The product gave the following data: NMR Spectrum: M + H$^+$ 532.
(o) The product gave the following data: NMR Spectrum: M + H$^+$ 560.
(p) The product gave the following data: NMR Spectrum: M + H$^+$ 546.
(q) The product gave the following data: NMR Spectrum: M + H$^+$ 505.
(r) The product gave the following data: NMR Spectrum: M + H$^+$ 574.
(s) The product gave the following data: NMR Spectrum: M + H$^+$ 517.
(t) The product gave the following data: NMR Spectrum: M + H$^+$ 517.
(u) The product gave the following data: NMR Spectrum: M + H$^+$ 530.
(v) The product gave the following data: NMR Spectrum: M + H$^+$ 558.
(w) The product gave the following data: NMR Spectrum: M + H$^+$ 544.
(x) The product gave the following data: NMR Spectrum: M + H$^+$ 517.
(y) The product gave the following data: NMR Spectrum: M + H$^+$ 532.
(z) The product gave the following data: NMR Spectrum: M + H$^+$ 560.
(aa) The product gave the following data: NMR Spectrum: M + H$^+$ 546.
(bb) The product gave the following data: NMR Spectrum: M + H$^+$ 505.
(cc) The product gave the following data: NMR Spectrum: M + H$^+$ 574.
(dd) Diethylammonium chloride was used as the source of the amine. An additional equivalent of potassium carbonate was added to neutralise the ammonium salt. The product gave the following data: NMR Spectrum: M + H$^+$ 503.
(ee) The product gave the following data: NMR Spectrum: M + H$^+$ 517.
(ff) The product gave the following data: NMR Spectrum: (DMSOd$_6$)2.37(m, 4H), 3.11(m, 4H), 3.54(s, 2H), 3.57(m, 4H), 3.72(m, 4H), 6.54(d, 1H), 7.13(s, 1H), 7.2(d, 1H), 7.5(m, 2H), 7.72(d, 1H), 7.85(m, 3H), 8.14(s, 1H), 10.21(s, 1H), 10.29(s, 1H); Mass Spectrum: M + H$^+$ 553.
(gg) The product gave the following data: NMR Spectrum: (DMSOd$_6$)2.3(m, 4H), 2.68(m, 4H), 3.11(m, 4H), 3.5(s, 2H), 3.72(m, 4H), 6.54(d, 1H), 7.13(s, 1H), 7.19(d, 1H), 7.5(m, 2H), 7.72(d, 1H), 7.87(m, 3H), 8.15(s, 1H), 10.2(s, 1H)10.29(s, 1H); Mass Spectrum: M + H$^+$ 552.
(hh) The product gave the following data: NMR Spectrum: M + H$^+$ 566.
(ii) The product gave the following data: NMR Spectrum: M + H$^+$ 594.
(jj) The product gave the following data: NMR Spectrum: M + H$^+$ 580.
(kk) The product gave the following data: NMR Spectrum: M + H$^+$ 553.
(ll) The product gave the following data: NMR Spectrum: M + H$^+$ 568.
(mm) The product gave the following data: NMR Spectrum: M + H$^+$ 596.
(nn) The product gave the following data: NMR Spectrum: M + H$^+$ 582.
(oo) The product gave the following data: NMR Spectrum: M + H$^+$ 541.
(pp) The product gave the following data: NMR Spectrum: M + H$^+$ 610.
(qq) The product gave the following data: NMR Spectrum: M + H$^+$ 553.
(rr) The product gave the following data: NMR Spectrum: (DMSOd$_6$)2.37(m, 4H), 3.11(m, 4H), 3.54(s, 2H), 3.58(m, 4H), 3.72(m, 4H), 6.54(d, 1H), 7.14(s, 1H), 7.19(d, 1H), 7.47(d, 2H), 7.72(d, 1H), 7.85(d, 1H), 7.96(d, 2H), 8.14(s, 1H), 10.16(s, 1H), 10.29(s, 1H); Mass Spectrum: M + H$^+$ 553.
(ss) The product gave the following data: NMR Spectrum: M + H$^+$ 566.
(tt) The product gave the following data: NMR Spectrum: M + H$^+$ 580.
(uu) The product gave the following data: NMR Spectrum: M + H$^+$ 553.
(vv) The product gave the following data: NMR Spectrum: M + H$^+$ 568.
(ww) The product gave the following data: NMR Spectrum: M + H$^+$ 596.

TABLE IV-continued

| No. | $(R^1)_m$ | $R^3$ | R | Note |
|---|---|---|---|---|

(xx) The product gave the following data: NMR Spectrum: M + H⁺ 582.
(yy) The product gave the following data: NMR Spectrum: M + H⁺ 541.
(zz) The product gave the following data: NMR Spectrum: M + H⁺ 610.
(aaa) Diethylammonium chloride was used as the source of the amine. An additional equivalent of potassium carbonate was added to neutralise the ammonium salt. The product gave the following data: NMR Spectrum: (DMSOd₆)0.98(t, 6H), 2.46(peak obscured by solvent), 3.11(m, 4H), 3.6(s, 2H), 3.72(m, 4H), 6.54(d, 1H), 7.14(s, 1H), 7.20(d, 1H), 7.47(d, 2H), 7.72(d, 1H), 7.85(d, 1H), 7.95(d, 2H), 8.15(s, 1H), 10.14(s, 1H), 10.29(s, 1H); Mass Spectrum: M + H⁺ 539.
(bbb) The product gave the following data: NMR Spectrum: M + H⁺ 553.

EXAMPLE 32

4-methyl-N-(3-morpholinophenyl)-3-(6-quinolylcarbonylamino)benzamide

Using an analogous procedure to that described in Example 1, 6-quinolylcarbonyl chloride was reacted with 3-amino-4-methyl-N-(3-morpholinophenyl)benzamide to give the title compound; NMR Spectrum: (DMSOd₆) 2.35 (s, 3H), 3.0-3.1 (m, 4H), 3.65-3.75 (m, 4H), 6.65-6.7 (m, 1H), 7.17 (t, 1H), 7.3-7.35 (m, 1H), 7.38-7.48 (m, 2H), 7.6-7.7 (m, 1H), 7.8-7.85 (m, 1H), 8.0 (s, 1H), 8.1-8.15 (m, 1H), 8.3-8.35 (m, 1H), 8.5-8.55 (m, 1H), 8.7 (s, 1H), 8.98-9.02 (m, 1H), 10.0-10.1 (br s, 1H), 10.25-10.35 (br s, 1H); Mass Spectrum: M+H⁺ 467.

EXAMPLE 33

4-chloro-3-(6-chloropyrid-3-ylcarbonylamino)-N-(3-fluoro-5-morpholinophenyl)benzamide A mixture of 6-chloropyrid-3-ylcarbonyl chloride (1.96 g), 3-amino-4-chloro-N-(3-fluoro-5-morpholinophenyl)benzamide (3 g) and pyridine (20 ml) was stirred and heated to 100° C. for 4 hours. The mixture was cooled to ambient temperature. Water and diethyl ether were added. The resultant precipitate was washed with a saturated aqueous sodium bicarbonate solution and with methanol. There was thus obtained the title compound (3.8 g); NMR Spectrum: (DMSOd₆) 3.1 (t, 4H), 3.75 (t, 4H), 6.52 (d, 1H), 7.1 (s, 1H), 7.2 (d, 1H), 7.6-7.7 (m, 2H), 7.7-7.8 (m, 1H), 8.2 (d, 1H), 8.35-8.4 (m, 1H), 8.97 (d, 1H), 10.2-10.32 (br S, 1H); Mass Spectrum: M+H⁺ 489.

EXAMPLE 34

3-(6-chloropyrid-3-ylcarbonylamino)-4-methyl-N-(3-morpholinophenyl)benzamide

Using an analogous procedure to that described in Example 33, 6-chloropyrid-3-ylcarbonyl chloride was reacted with 3-amino-4-methyl-N-(3-morpholinophenyl)benzamide to give the title compound; NMR Spectrum: (DMSOd₆) 2.3 (s, 3H), 3.05 (t, 4H), 3.75 (t, 4H), 6.65-6.75 (m, 1H), 7.18 (t, 1H), 7.25-7.3 (m, 1H), 7.3-7.5 (m, 2H), 7.7 (d, 1H), 7.75-7.85 (m, 1H), 7.97 (s, 1H), 8.35-8.45 (m, 1H), 9.0 (d, 1H), 10.0-10.04 (s, 1H), 10.26-10.29 (s, 1H); Mass Spectrum: M+H⁺ 451.

EXAMPLE 35

4-chloro-N-(3-fluoro-5-morpholinophenyl)-3-[6-(4-methylpiperazin-1-yl)pyrid-3-ylcarbonylamino]benzamide A mixture of 4-chloro-3-(6-chloropyrid-3-ylcarbonylamino)-N-(3-fluoro-5-morpholinophenyl)benzamide (0.2 g) and N-methylpiperazine (1.5 g) was stirred and heated to 110° C. for 20 hours. The mixture was cooled to ambient temperature. Water was added and the mixture was stirred at ambient temperature for 30 minutes. The resultant precipitate was isolated, washed with water and dried. There was thus obtained the title compound (0.18 g); Mass Spectrum: M+H⁺ 553.

EXAMPLE 36

Using an analogous procedure to that described in Example 35, the appropriate chloropyridine was reacted with the appropriate amine to give the compounds described in Table V.

TABLE V

| No. | $R^1$ | $R^3$ | R | Note |
|---|---|---|---|---|
| 1 | 2-dimethylaminoethylamino | methyl | 3-morpholino | (a) |
| 2 | N-(2-methylaminoethyl)-N-methylamino | methyl | 3-morpholino | (b) |
| 3 | N-(2-dimethylaminoethyl)-N-methylamino | methyl | 3-morpholino | (c) |

TABLE V-continued

[Chemical structure: pyridine-CONH-phenyl(R³)-CONH-phenyl-R]

| No. | R¹ | R³ | R | Note |
|---|---|---|---|---|
| 4 | 2-amino-2-methylpropylamino | methyl | 3-morpholino | (d) |
| 5 | 3-aminopropylamino | methyl | 3-morpholino | (e) |
| 6 | N-(3-dimethylaminopropyl)-N-methylamino | methyl | 3-morpholino | (f) |
| 7 | 3-morpholinopropylamino | methyl | 3-morpholino | (g) |
| 8 | 4-aminobutylamino | methyl | 3-morpholino | (h) |
| 9 | 4-methylpiperazin-1-yl | methyl | 3-morpholino | (i) |
| 10 | homopiperazin-1-yl | methyl | 3-morpholino | (j) |
| 11 | 2-dimethylaminoethylamino | chloro | 3-fluoro-5-morpholino | (k) |
| 12 | N-(2-methylaminoethyl)-N-methylamino | chloro | 3-fluoro-5-morpholino | (l) |
| 13 | N-(2-dimethylaminoethyl)-N-methylamino | chloro | 3-fluoro-5-morpholino | (m) |
| 14 | 2-amino-2-methylpropylamino | chloro | 3-fluoro-5-morpholino | (n) |
| 15 | 3-dimethylaminopropylamino | chloro | 3-fluoro-5-morpholino | (o) |
| 16 | N-(3-methylaminopropyl)-N-methylamino | chloro | 3-fluoro-5-morpholino | (p) |
| 17 | N-(3-dimethylaminopropyl)-N-methylamino | chloro | 3-fluoro-5-morpholino | (q) |
| 18 | 3-morpholinopropylamino | chloro | 3-fluoro-5-morpholino | (r) |
| 19 | 4-dimethylaminobutylamino | chloro | 3-fluoro-5-morpholino | (s) |
| 20 | homopiperazin-1-yl | chloro | 3-fluoro-5-morpholino | (t) |

Notes
(a) The product gave the following data: Mass Spectrum: M + H⁺ 503.
(b) The product gave the following data: Mass Spectrum: M + H⁺ 503.
(c) The product gave the following data: Mass Spectrum: M + H⁺ 517.
(d) The product gave the following data: Mass Spectrum: M + H⁺ 503.
(e) The product gave the following data: Mass Spectrum: M + H⁺ 489.
(f) The product gave the following data: Mass Spectrum: M + H⁺ 531.
(g) The product gave the following data: Mass Spectrum: M + H⁺ 559.
(h) The product gave the following data: Mass Spectrum: M + H⁺ 503.
(i) The product gave the following data: Mass Spectrum: M + H⁺ 515.
(j) The product gave the following data: Mass Spectrum: M + H⁺ 515.
(k) The product gave the following data: Mass Spectrum: M + H⁺ 541.
(l) The product gave the following data: Mass Spectrum: M + H⁺ 541.
(m) The product gave the following data: Mass Spectrum: M + H⁺ 555.
(n) The product gave the following data: Mass Spectrum: M + H⁺ 541.
(o) The product gave the following data: Mass Spectrum: M + H⁺ 555.
(p) The product gave the following data: Mass Spectrum: M + H⁺ 555.
(q) The product gave the following data: Mass Spectrum: M + H⁺ 569.
(r) The product gave the following data: Mass Spectrum: M + H⁺ 597.
(s) The product gave the following data: Mass Spectrum: M + H⁺ 569.
(t) The product gave the following data: Mass Spectrum: M + H⁺ 553.

EXAMPLE 37

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph•Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph•Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph•Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph•Eur | 488.5 |
| Magnesium | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

-continued

| (f) Injection II | (10 mg/ml) | |
|---|---|---|
| Compound X | 1.0% | w/v |
| Sodium phosphate BP | 3.6% | w/v |
| 0.1 M Sodium hydroxide solution | 15.0% | v/v |
| Water for injection to 100% | | |

| (g) Injection III | (1 mg/ml, buffered to pH6) | |
|---|---|---|
| Compound X | 0.1% | w/v |
| Sodium phosphate BP | 2.26% | w/v |
| Citric acid | 0.38% | w/v |
| Polyethylene glycol 400 | 3.5% | w/v |
| Water for injection to 100% | | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml | |
|---|---|---|
| Compound X | 40 | mg |
| Ethanol | 300 | μl |
| Water | 300 | μl |
| 1-Dodecylazacycloheptan-2-one | 50 | μl |
| Propylene glycol | to 1 | ml |

Note
The above formulations may be obtained by conventional procedures well known in the pharmaceutical art.
The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

The invention claimed is:
1. An amide derivative of the Formula I

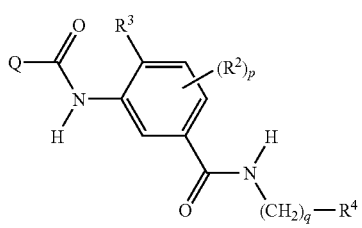

wherein
R³ is (1-6C)alkyl or halogeno;
Q is a 5- or 6-membered monocyclic heteroaryl ring of a 9- or 10-membered bicyclic heteroaryl ring with up to 5 ring heteroatoms selected from oxygen, nitrogen and sulphur, which optionally bears 1, 2, 3 or 4 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-3C)alkylenedioxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alklyamino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl- (1-6C)alkylamino, heteroarylcarbonylamino, heteroarylsulphonylamino, N-heteroarylsulphamoyl, heteroaryl-(2-6C)alkanoylamino, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl and heterocyclyl-(2-6C)alkanoylamino, and wherein any of the substituents on Q defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl;

and wherein any aryl, heteroaryl or heterocyclyl group in a substituent on Q may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl;

$R^2$ is hydroxy, halogeno, trifluoromethyl, cyano, mercapto, nitro, amino, carboxy, (1-6C)alkoxycarbonyl, (1-6C)alkyl, (2-6C)alkenyl, (2-6C)alkynyl, (1-6C)alkoxy, (1-6C)alkylamino or di-[(1-6C)alkyl]amino;

p is 0, 1 or 2;

q is 0, 1, 2, 3 or 4; and $R^4$ is aryl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, cycloalkyl, heteroaryl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl or heteroaryl-(2-6C)alkanoylamino, heterocyclyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl or heterocyclyl-(2-6C)alkanoylamino and $R^4$ optionally bears 1, 2, 3 or 4 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-3C)alkylenedioxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alklyamino, N-(1-6C)alklyamino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl and heterocyclyl-(2-6C)alkanoylamino, and wherein any of the substituents on $R^4$ defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl;

and wherein any aryl, heteroaryl or heterocyclyl group in a substituent on $R^4$ may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]

amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl;

or a pharmaceutically-acceptable salt or in-vivo-cleavable ester thereof.

2. An amide derivative of the Formula I according to claim 1 wherein Q is substituted by a basic substituent selected from the substituents for Q defined in claim 1 and $R^4$ is a phenyl or heteroaryl group as defined in claim 1 which also bears a basic substituent selected from the substituents for $R^4$ defined in claim 1.

3. An amide derivative of the Formula I according to claim 1 selected from:
N-(3-dimethylaminophenyl)-4-methyl-3-(6-quinolylcarbonylamino)benzamide, 4-chloro-N-(3-dimethylaminophenyl)-3-(6-quinolylcarbonylamino)benzamide, and
3-[6-(2-amino-2-methylpropylamino)pyrid-3-ylcarbonylamino]-4-chloro-N-(3-fluoro-5-morpholinophenyl)benzamide;

or a pharmaceutically-acceptable salt thereof.

4. An amide derivative of the Formula I according to claim 1 wherein
$R^3$ is methyl, ethyl, chloro or bromo;
Q is furyl, thienyl, oxazolyl, isoxazolyl, imidazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, quinolyl, isoquinolyl, quinazolinyl, quinoxalinyl or naphthyridinyl which optionally bears 1 or 2 substituents selected from hydroxy, fluoro, chloro, trifluoromethyl, cyano, methyl, ethyl, methoxy and ethoxy;
p is 0;
q is 0; and
$R^4$ is phenyl which bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, acetyl, propionyl, chloromethyl, methoxymethyl, 2-methoxyethyl, methylaminomethyl, ethylaminomethyl, dimethylaminomethyl, diethylaminomethyl, 2-chloroethoxy, 3-chloropropoxy, 2-hydroxyethoxy, 3-hydroxypropoxy, 2-methoxyethoxy, 2-ethoxyethoxy, 3-methoxypropoxy, 3-ethoxypropoxy, cyanomethoxy, carboxymethoxy, methoxycarbonylmethoxy, ethoxycarbonylmethoxy, tert-butoxycarbonylmethoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-chloroethylamino, 2-hydroxyethylamino, 2-methoxyethylamino, 2-ethoxyethylamino, 2-aminoethylamino, 2-methylaminoethylamino, 2-ethylaminoethylamino, 2-dimethylaminoethylamino, 2-diethylaminoethylamino, N-(2-chloroethyl)-N-methylamino, N-(2-hydroxyethyl)-N-methylamino, N-(2-methoxyethyl)-N-methylamino, N-(2-ethoxyethyl)-N-methylamino, N-(2-aminoethyl)-N-methylamino, N-(2-methylaminoethyl)-N-methylamino, N-(2-dimethylaminoethyl)-N-methylamino, N-(3-aminopropyl)-N-methylamino, N-(3-methylaminopropyl)-N-methylamino, N-(3-ethylaminopropyl)-N-methylamino, N-(3-dimethylaminopropyl)-N-methylamino, N-(3-diethylaminopropyl)-N-methylamino, phenyl, benzyl, benzyloxy, 2-pyridylmethoxy, 2-(imidazol-1-yl)ethoxy, 3-(imidazol-1-yl)propoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

5. An amide derivative of the Formula I according to claim 1 wherein
$R^3$ is methyl or chloro;
Q is 3-isoxazolyl, 3-pyridyl or 6-quinolyl which optionally bears a substituent selected from chloro and methyl;
p is 0;
q is 0; and
$R^4$ is phenyl which bears a dimethylamino substituent;
or a pharmaceutically-acceptable salt thereof.

6. An amide derivative of the Formula I according to claim 1 wherein
$R^3$ is methyl or chloro;
Q is 3-pyridyl or 4-pyridyl which bears a substituent selected from 2-aminoethylamino, 3-aminopropylamino, 2-amino-2-methylpropylamino, 4-aminobutylamino, 2-methylaminoethylamino, 2-ethylaminoethylamino, 3-methylaminopropylamino, 4-methylaminobutylamino, 2-dimethylaminoethylamino, 2-diethylaminoethylamino, 3-dimethylaminopropylamino, 4-dimethylaminobutylamino, N-(2-ethylaminoethyl)-N-methylamino, N-(3-methylaminopropyl)-N-methylamino, N-(4-ethylaminobutyl)-N-methylamino, N-(2-dimethylaminoethyl)-N-methylamino, N-(3-dimethylaminopropyl)-N-methylamino, N-(4-dimethylaminobutyl)-N-methylamino, pyrrolidin-1-yl, 3-hydroxypyrrolidin-1-yl, morpholino, piperidino, homopiperidino, piperazin-1-yl, homopiperazin-1-yl, 4-methylpiperazin-1-yl, 4-ethylpiperazin-1-yl, 4-(2-hydroxyethyl)piperazin-1-yl, 4-methylhomopiperazin-1-yl, 3-morpholinopropylamino or 2-(1-methylpyrrolidin-2-yl)ethylamino;
p is 0;
q is 0; and
$R^4$ is phenyl which is substituted at the 3-position with a substituent selected from dimethylamino, diethylamino, pyrrolidin-1-yl, piperidino, morpholino, piperazin-1-yl, homopiperazin-1-yl, 4-methylpiperazin-1-yl and 4-methylhomopiperazin-1-yl and $R^4$ is optionally substituted with a further substituent selected from fluoro, chloro, cyano, methyl and trifluoromethyl;
or a pharmaceutically-acceptable salt thereof.

7. A process for the preparation of an amide derivative of the Formula I, or a pharmaceutically-acceptable salt or in-vivo-cleavable ester thereof, according to claim 1 which comprises:—
(a) reacting a benzoic acid of the Formula II, or a reactive derivative thereof,

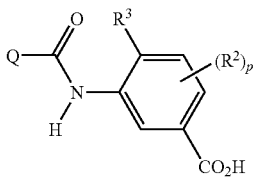

with an amine of the Formula III

under standard amide bond forming conditions, wherein variable groups are as defined in claim 1 and wherein any functional group is protected if necessary, and:
(i) removing any protecting groups; and
(ii) optionally forming a pharmaceutically-acceptable salt or in-vivo-cleavable ester;
(b) reacting an acid of the Formula IV, or an activated derivative thereof,

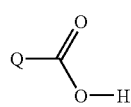

with an aniline of the Formula VI

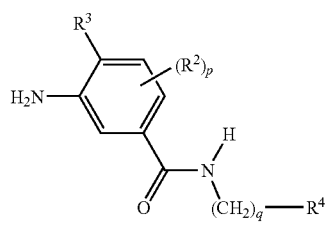

under standard amide bond forming conditions as defined hereinbefore, wherein variable groups are as defined in claim 1 and wherein any functional group is protected, if necessary, and:
(i) removing any protecting groups;
(ii) optionally forming a pharmaceutically-acceptable salt or in-vivo-cleavable ester;
(c) for the preparation of a compound of the Formula I wherein a substituent on Q or $R^4$ is (1-6C)alkoxy or substituted (1-6C)alkoxy, (1-6C)alkylthio, (1-6C)alkylamino, di-[(1-6C)alkyl]amino or substituted (1-6C)alkylamino or heterocyclyloxy, the alkylation, conveniently in the presence of a suitable base, of an amide derivative of the Formula I wherein a substituent on Q or $R^4$ is hydroxy, mercapto or amino as appropriate;
(d) for the preparation of a compound of the Formula I wherein a substituent on Q or $R^4$ is (1-6C)alkanoylamino or substituted (2-6C)alkanoylamino, the acylation of a compound of the Formula I wherein a substituent on Q or $R^4$ is amino;
(e) for the preparation of a compound of the Formula I wherein a substituent on Q or $R^4$ is (1-6C)alkanesulphonylamino, the reaction of a compound of the Formula I wherein a substituent on Q or $R^4$ is amino with a (1-6C)alkanesulphonic acid, or an activated derivative thereof;
(f) for the preparation of a compound of the Formula I wherein a substituent on Q or $R^4$ is carboxy, carboxy-(1-6C)alkyl, carboxy-(1-6C)alkoxy, carboxy-(1-6C)alkylamino, N-(1-6C)alkyl-carboxy-(1-6C)alkylamino or carboxy-(2-6C)alkanoylamino, the cleavage of a compound of the Formula I wherein a substituent on Q or $R^4$ is (1-6C)alkoxycarbonyl, (1-6C)alkoxycarbonyl-(1-6C)alkyl, (1-6C)alkoxycarbonyl-(1-6C)alkoxy, (1-6C)alkoxycarbonyl-(1-6C)alkylamino, N-(1-6C)alkyl-(1-6C)alkoxycarbonyl-(1-6C)alkylamino or (1-6C)alkoxycarbonyl-(2-6C)alkanoylamino as appropriate;
(g) for the preparation of a compound of the Formula I wherein a substituent on Q or $R^4$ is amino-(1-6C)alkyl, heterocyclyl-(1-6C)alkyl, (1-6C)alkylamino-(1-6C)alkyl, di-[(1-6C)alkyl]amino-(1-6C)alkyl, substituted (2-6C)alkylamino-(1-6C)alkyl or substituted N-(1-6C)alkyl-(2-6C)alkylamino-(1-6C)alkyl, the reaction of a compound of the Formula I wherein a substituent on Q or $R^4$ is a group of the formula -(1-6C)alkylene-Z wherein Z is a displaceable group with an appropriate amine or heterocyclyl compound;
(h) for the preparation of a compound of the Formula I wherein a substituent on Q or $R^4$ is amino, heterocyclyl, (1-6C)alkylamino, di-[(1-6C)alkyl]amino, substituted (1-6C)alkylamino, substituted N-(1-6C)alkyl-(1-6C)alkylamino, substituted (2-6C)alkylamino or substituted N-(1-6C)alkyl-(2-6C)alkylamino, the reaction of a compound of the Formula I wherein a substituent on Q or $R^4$ is a displaceable group Z with an appropriate amine or heterocyclyl compound;
(i) for the preparation of a compound of the Formula I wherein a substituent on Q or $R^4$ is N-(1-6C)alkyl-(1-6C)alkanesulphonylamino, the alkylation, conveniently in the presence of a suitable base, of an amide derivative of the Formula I wherein a substituent on Q or $R^4$ is (1-6C)alkanesulphonylamino;
(j) for the preparation of a compound of the Formula I wherein a substituent on Q or $R^4$ is a hydroxy-heterocyclyl-(1-6C)alkoxy group, a hydroxy-(1-6C)alkylamino-(2-6C)alkoxy group or a hydroxy-di-[(1-6C)alkyl]amino-(2-6C)alkoxy group, the reaction of a compound of the Formula I wherein a substituent on Q or $R^4$ is a epoxy-substituted (1-6C)alkoxy group with a heterocyclyl compound or an appropriate amine; or
(k) for the preparation of a compound of the Formula I wherein $R^2$ or a substituent on Q or $R^4$ is an amino group, the reduction of a compound of the Formula I wherein $R^2$ or a substituent on Q or $R^4$ is a nitro group.

8. A pharmaceutical composition which comprises an amide derivative of the Formula I, or a pharmaceutically-acceptable salt or in-vivo-cleavable ester thereof, according to any one of claims 1, 2, 3, 4, 5 and 6 in association with a pharmaceutically-acceptable diluent or carrier.

* * * * *